United States Patent
Shimizu et al.

(10) Patent No.: US 8,829,040 B2
(45) Date of Patent: *Sep. 9, 2014

(54) (AZA)INDOLE DERIVATIVE AND USE THEREOF FOR MEDICAL PURPOSES

(71) Applicant: Kissei Pharmaceutical Co., Ltd., Matsumoto (JP)

(72) Inventors: Kazuo Shimizu, Azumino (JP); Yasushi Takigawa, Azumino (JP); Hideki Fujikura, Azumino (JP); Masato Iizuka, Azumino (JP); Masahiro Hiratochi, Azumino (JP); Norihiko Kikuchi, Azumino (JP)

(73) Assignee: Kissei Pharmaceutical Co., Ltd., Matsumoto-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/193,911

(22) Filed: Feb. 28, 2014

(65) Prior Publication Data

US 2014/0179932 A1  Jun. 26, 2014

Related U.S. Application Data

(60) Continuation of application No. 13/895,634, filed on May 16, 2013, which is a continuation of application No. 13/116,389, filed on May 26, 2011, now Pat. No. 8,466,152, which is a division of application No. 12/595,476, filed as application No. PCT/JP2008/057089 on Apr. 10, 2008, now Pat. No. 8,003,647.

(30) Foreign Application Priority Data

Apr. 11, 2007 (JP) ................ 2007-104096

(51) Int. Cl.
*A61K 31/404* (2006.01)
*C07D 209/30* (2006.01)
*C07D 209/42* (2006.01)

(52) U.S. Cl.
CPC ........... *C07D 209/42* (2013.01); *C07D 209/30* (2013.01)
USPC ............. 514/415; 548/503; 548/509

(58) Field of Classification Search
CPC ................ C07D 209/30; C07D 209/42
USPC ................... 548/503, 509; 514/415
See application file for complete search history.

(56) References Cited

U.S. PATENT DOCUMENTS

| | | | |
|---|---|---|---|
| 3,491,114 A | 1/1970 | Suh | |
| 5,696,143 A | 12/1997 | Talley et al. | |
| 6,015,829 A | 1/2000 | Ishibuchi et al. | |
| 6,107,301 A | 8/2000 | Aldrich et al. | |
| 2009/0306396 A1 | 12/2009 | Toyoshima et al. | |

FOREIGN PATENT DOCUMENTS

| | | |
|---|---|---|
| EP | 1932833 A1 | 6/2008 |
| JP | 2000-001431 A | 1/2000 |
| JP | 3220987 B2 | 10/2001 |
| WO | 96-09293 A1 | 3/1996 |
| WO | 2007-043400 A1 | 4/2007 |
| WO | 2007-043401 A1 | 4/2007 |

OTHER PUBLICATIONS

International Search Report of PCT/JP2008/057089, Mailing Date of Jun. 17, 2008.

Toyoshima, T. et al., Preparation of nitrogenated heterocyclic compounds as xanthine oxidase inhibitors and pharmaceutical compositions comprising the same (Document No. 146:421993, HCAPLUS) retrieved on Sep. 27, 2010.

Toyoshima, T. et al., Preparation of nitrogenated aromatic heterocyclic compounds as xanthine oxidase inhibitors and pharmaceutical composition comprising the same (Document No. 146:441792, HCAPLUS) retrieved on Sep. 27, 2010, 192pp (Related to WO2007043400 and US2007/0306396).

(Continued)

*Primary Examiner* — Shawquia Young
(74) *Attorney, Agent, or Firm* — Westerman, Hattori, Daniels & Adrian, LLP

(57) ABSTRACT

The present invention provides compounds useful as agents for the prevention or treatment of a disease associated with abnormal serum uric acid level which has a uricosuric activity or the like. The present invention relates to (aza)indole derivatives represented by the following general formula (I) having xanthine oxidase inhibitory activities and useful as agents for the prevention or treatment of a disease associated with abnormality of serum uric acid level, prodrugs thereof, or salts thereof. In the formula (I), T represents nitro or cyano and the like; ring J represents aryl or heteroaryl and the like; Q represents carboxy or 5-tetazolyl and the like; Y represents H, OH, $NH_2$, halogen, nitro, alkyl, alkoxy and the like; $X^1$, $X^2$ and $X^3$ independently represent $CR^2$ or N; $R^1$ and $R^2$ independently represent halogen, cyano, haloalkyl, A-D-E-G, —N(-D-E-G)$_2$ and the like, in the formula, A represents a single bond, O, S and the like; D and G independently represent optionally substituted alkylene, cycloalkylene, heterocycloalkylene, arylene, heteroarylene and the like; E represents a single bond, O, S, COO, $SO_2$ and the like.

(I)

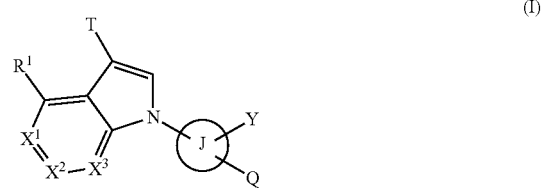

4 Claims, No Drawings

(56) References Cited

OTHER PUBLICATIONS

Gout [online] retrieved on Sep. 27, 2010 from internet. URL; http://www.nlm.nih.gov/medlineplus/ency/article/000422.htm.

European Search Report dated Apr. 28, 2011, issued in corresponding European patent Application No. 08740190.7.

Keitaro Senga etal., "Synthesis and Xanthine Oxidase Inhibotory Activity of 4.6-Disubstituted 1-p-Chlorophenylpyrazolo[3,4-d]pyrimidines", Journal of Heterocyclic, vol. 6, 1982, pp. 1565-1567.

(AZA)INDOLE DERIVATIVE AND USE THEREOF FOR MEDICAL PURPOSES

This application is a continuation of U.S. application Ser. No. 13/895,634, filed May 16, 2013, which is a continuation of U.S. application Ser. No. 13/116,389, filed May 26, 2011, which is a divisional of U.S. application Ser. No. 12/595,476, filed Oct. 9, 2009, now issued as U.S. Pat. No. 8,003,647, which is a National Stage of International Application No. PCT/JP2008/057089, filed Apr. 10, 2008, which claims priority to Japanese priority application No. 2007-104096 filed Nov. 4, 2007, which are all hereby incorporated by reference.

TECHNICAL FIELD

The present invention relates to (aza)indole derivatives useful as medicaments.

More particularly, the present invention relates to (aza)indole derivatives having xanthine oxidase inhibitory activities and useful as agents for the prevention or treatment of a disease associated with abnormality of serum uric acid level, prodrugs thereof, or pharmaceutically acceptable salts thereof.

BACKGROUND ART

Uric acid is the final product of purine metabolism in human. In many mammals, unlike human, uric acid is further broken down by urate oxidase (uricase) in the liver into allantoin, which is excreted through the kidney. In human, main pathway of uric acid excretion is the kidney, wherein approximately two thirds of uric acid is excreted in urine. The remaining is excreted in feces. When an excessive production or decreased excretion of uric acid occurs, that causes hyperuricemia. Hyperuricemia is classified into a uric acid overproduction type, a uric acid underexcretion type and a mixed type thereof. This classification of hyperuricemia is clinically important. Aiming for reducing adverse effects of therapeutic agents, therapeutic agents are chosen according to each class (for example, see Non-patent reference 1).

In hyperuricemia with a uric acid overproduction type, urinary excretion of uric acid increases, and when the urinary excretion of uric acid further increases by using of a uricosuric drug, the complication of urinary calculi is possibly developed. Therefore, in principle, allopurinol, a uric acid production inhibitor (or sometimes called a uric acid synthesis inhibitor, hereinafter referred to as "a uric acid production inhibitor"), is used in a uric acid overproduction type.

Uric acid is produced from purine bodies, which are derived from diet and synthesized endogenously, finally by oxidizing xanthine by xanthine oxidase. Allopurinol is developed as a xanthine oxidase inhibitor and an only uric acid production inhibitor used in medical practice. While allopurinol, however, is reported being effective in hyperuricemia and various diseases caused by the same, severe adverse effects such as poisoning syndrome (hypersensitivity angiitis), Stevens-Johnson syndrome, exfoliative dermatitis, anaplastic anemia, liver dysfunction and the like have been also reported (for example, see Non-patent reference 2). As one of the causes, it has been pointed out that allopurinol has a nucleic acid-like structure and inhibits a pathway of pyrimidine metabolism (for example, see Non-patent reference 3).

On the other hand, in hyperuricemia with a uric acid underexcretion type, uric acid excretion decreases. It has been reported that when allopurinol, which is metabolized into oxypurinol to be excreted through the kidney by the same mechanism to uric acid, is used, the excretion of oxypurinol also decreases and that increases the incidence of liver disorders (for example, see Non-patent reference 4). Therefore, in principle, uricosuric drugs such as probenecid, benzbromarone and the like are used in a uric acid underexcretion type. These uricosuric drugs, however, also exert adverse effects such as gastrointestinal disorders, urinary calculi or the like. Particularly, benzbromarone is known as possibly causing fluminant hepatitis in the case of idiosyncratic patients (for example, see Non-patent reference 5).

Thus, it is said that both of the existing uric acid production inhibitor and uricosuric drug have usage restrictions in patients or severe adverse effects. Therefore, the development of an easy-to-use agent for the treatment of hyperuricemia has been desired.

Uric acid is eliminated mainly by the kidney, and the urate dynamics in the kidney has been investigated so far in some experiments using brush-border membrane vesicles (BBMV) prepared from the renal cortex (for example, see Non-patent references 6 and 7). It has been known that in human, uric acid is passed through the kidney glomerulus freely, and there are mechanisms of reabsorption and secretion of uric acid in the proximal tubule (for example, see Non-patent reference 8).

In recent years, the gene (SLC22A12) encoding the human kidney urate transporter has been identified (for example, see Non-patent reference 9). The transporter encoded by this gene (urate transporter 1, hereinafter referred to as "URAT1") is a 12-transmembrane type molecule belonging to OAT family. URAT1 mRNA was specifically expressed in the kidney, and localization of URAT1 in apical side of the proximal tubule was observed on the human kidney tissue section. In an experiment using *xenopus* oocyte expression system, uptake of uric acid through URAT1 was shown. Furthermore, it was shown that the uptake of uric acid is transported by exchange with organic anions such as lactic acid, pyrazinecarboxylic acid (PZA), nicotinic acid and the like, and the uric acid uptake through URAT1 is inhibited by uricosuric drugs, probenecid and benzbromarone. Thus, as expected by the experiment using membrane vesicles, it was strongly suggested that URAT1 is a urate/anion exchanger. That is, it was shown that URAT1 is a transporter that plays an important role in uric acid reabsorption in the kidney (for example, see Non-patent reference 9).

In addition, the relation between URAT1 and diseases became clear. Idiopathic renal hypouricemia is a disease wherein uric acid excretion is increased due to abnormal urate dynamics in the kidney and the serum uric acid level becomes low. It is known that the disease is often associated with urinary calculi or acute renal failure after exercise. URAT1 was identified as a causative gene of the renal hypouricemia (for example, see Non-patent reference 9). These things also strongly suggest that URAT1 is responsible for controlling the blood uric acid level.

Therefore, a substance having a URAT1 inhibitory activity is useful as an agent for the treatment and prevention of diseases associated with high blood uric acid levels, that is, hyperuricemia, gouty tophus, gouty arthritis, renal disorder associated with hypeuricemia, urinary calculi or the like.

In the treatment of hyperuricemia, it was reported that a combination of allopurinol of a uric acid production inhibitor and an agent having a uricosuric activity lowered the serum uric acid level more strongly than the single use of allopurinol (for example, see Non-patent references 10 and 11). Therefore, when treatment with a single existing agent can not exert effect enough, a higher therapeutic effect can be expected by a combination use of a uric acid production inhibitor and a uricosuric agent. Furthermore, for hyperuricemia with the uric acid underexcretion type, it is considered that since urinary excretion of uric acid can be decreased by lowering blood uric acid level, the risk of urinary calculi caused by the monotherapy with a uricosuric agent can be reduced. In addition, for hyperuricemia with the mixed type, high therapeutic effect is expected. Thus, an agent having both an inhibitory activity of uric acid production and a uricosuric activity is expected to become an extremely useful agent for the prevention or treatment of hyperuricemia or the like.

As a compound having both xanthine oxidase inhibitory activity and URAT1 inhibitory activity, morin, a natural product, is known (see Non-patent reference 12). In addition, as a compound having a uricosuric activity, biaryl or diaryl ether compounds are known (see Patent reference 1).

It was reported that 1-phenylindole derivatives have a stem cell differentiation inhibitory effect (see Patent references 2 to 4). It was also reported that a 1-pyrimidine-indole derivative has a sodium channel inhibitory effect (see Patent reference 5). However, an (aza)indole derivative of the present invention has a different structure from the compounds described in the above references, and anything is neither described nor suggested about that it has a xanthine oxidase inhibitory activity or is useful for the prevention or treatment of a disease associated with abnormal serum uric acid level such as gout, hyperuricemia or the like.

Patent reference 1: Tokkai 2000-001431 (JPA2000-001431)
Patent reference 2: The international publication 2005/007838 pamphlet
Patent reference 3: Tokkai 2006-180763 (JPA2006-180763)
Patent reference 4: Tokkai 2006-204292 (JPA2006-204292)
Patent reference 5: The international publication 2005/003099 pamphlet
Non-patent reference 1: Atsuo Taniguchi and 1 person, *Modern Physician,* 2004, Vol. 24, No. 8, pp. 1309-1312
Non-patent reference 2: Kazuhide Ogino and 2 persons, *Nihon Rinsho* (Japan Clinical), 2003, Vol. 61, Extra edition 1, pp. 197-201
Non-patent reference 3: Hideki Horiuchi and 6 persons, *Life Science,* 2000, Vol. 66, No. 21, pp. 2051-2070
Non-patent reference 4: Hisashi Yamanaka and 2 persons, *Konyosankessyo to Tsufu* (Hyperuricemia and gout), issued by Medical Review Co., 1994, Vol. 2, No. 1, pp. 103-111
Non-patent reference 5: edited by *Konyosankessyo, tsufu no Chiryo guideline sakuseiiinkai* (The Committee establishing a guideline for the treatment of hyperuricemia and gout), The guideline for the treatment of hyperuricemia and gout, Edition 1, issued by Nihon *tsuhu kakusan taisya gakkai* (Japanese society of gout and nucleic acid metabolism), 2002, pp. 32-33
Non-patent reference 6: Francoise Roch-Ramel and 2 persons, Am. J. Physiol., 1994, Vol. 266 (Renal Fluid Electrolyte Physiol., Vol. 35), F797-F805
Non-patent reference 7: Francoise Roch-Ramel and 2 persons, J. Pharmacol. Exp. Ther., 1997, Vol. 280, pp. 839-845
Non-patent reference 8: Hiroaki Kimura and 3 persons, *Nihon rinsyo* (Japan Clinical), 2003, Vol. 61, Extra Edition 1, pp. 119-123
Non-patent reference 9: Atsushi Enomoto and 18 persons, Nature, 2002, Vol. 417, pp. 447-452
Non-patent reference 10: S Takahashi and 5 persons, Ann. Rheum. Dis., 2003, Vol. 62, pp. 572-575
Non-patent reference 11: M. D. Feher and 4 persons, Rheumatology, 2003, Vol. 42, pp. 321-325
Non-patent reference 12: Zhifeng Yu and 2 persons, J. Pharmacol. Exp. Ther., 2006, Vol. 316, pp. 169-175

DISCLOSURE OF THE INVENTION

Problem that the Invention Aims to Solve

The present invention is to provide an agent which has an inhibitory activity of uric acid production for the prevention or treatment of a disease associated with abnormal serum uric acid level.

Means to Solve the Problem

The present inventors have earnestly to solve the above problem. As a result, it was found that (aza)indole derivatives represented by the following general formula (I) exert an excellent xanthine oxidase inhibitory activity and extremely lower serum uric acid levels, and therefore, they can be an agent for the prevention or treatment of a disease associated with abnormal serum uric acid level, thereby forming the basis of the present invention.

That is, the present invention relates to:

[1] an (aza)indole derivative represented by the general formula:

[Chem. 1]

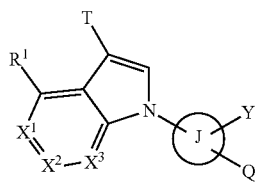

(I)

wherein T represents nitro, cyano or trifluoromethyl;
ring J represents an aryl ring or a heteroaryl ring;
Q represents carboxy, lower alkoxycarbonyl, carbamoyl, mono(di)(lower alkyl)carbamoyl, sulfo, sulfamoyl or 5-tetrazolyl;
Y represents a hydrogen atom, hydroxyl, amino, a halogen atom, nitro, optionally substituted lower alkyl or optionally substituted lower alkoxy with the proviso that two or more Y optionally exist on ring J and these Y are optionally the same or different from each other;
$X^1$, $X^2$ and $X^3$ independently represent $CR^2$ or N with the proviso that all of $X^1$, $X^2$ and $X^3$ do not represent N at the same time, and when two or more $R^2$ exist, these $R^2$ are optionally the same or different from each other; and
$R^1$ and $R^2$ independently represent a halogen atom, cyano, perfluoro(lower alkyl), $-A^A$, $-A-D-E-G$ or $-N(-D-E-G)_2$ with the proviso that two (-D-E-G) are optionally different from each other;
in the formula, $A^A$ represents a hydrogen atom, hydroxy, thiol, $-CHO$, carboxy, $-CONHR^3$, $-NHR^3$, $-N(R^3)CHO$, $-N(R^3)CONHR^4$ or $-SO_2NHR^3$;
A represents a single bond, $-O-$, $-S-$, $-CO-$, $-COO-$, $-CON(R^3)-$, $-SO_2-$, $-SO_2N(R^3)-$, $-N(R^3)-$, $-N(R^3)CO-$, $-N(R^3)COO-$, $-N(R^3)SO_2-$ or $-N(R^3)CONR^4-$ wherein $R^3$ and $R^4$ independently represent a hydrogen atom or lower alkyl;
D represents optionally substituted lower alkylene, optionally substituted lower alkenylene, optionally substituted lower alkynylene, optionally substituted cycloalkylene, optionally substituted heterocycloalkylene, optionally substituted arylene or optionally substituted heteroarylene with the proviso that D is optionally further substituted by -E-G;

E represents a single bond, —O—, —N($R^5$)—, —S—, —CO—, —COO—, —CON($R^5$)—, —SO$_2$—, —SO$_2$N($R^5$)—, —N($R^5$)CO—, —N($R^5$)COO—, —N(R)SO$_2$— or —N($R^5$)CON($R^6$)— with the proviso that $R^5$ and $R^6$ independently represent a hydrogen atom or lower alkyl; and G represents a hydrogen atom, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, optionally substituted cycloalkyl(lower alkyl), optionally substituted heterocycloalkyl(lower alkyl), optionally substituted aryl(lower alkyl) or optionally substituted heteroaryl(lower alkyl) with the proviso that when G is a hydrogen atom, E is a single bond, —O—, —N($R^5$)—, —S—, —COO—, —CON($R^5$)—, —N($R^5$)CO—, —N($R^5$)CON($R^6$)— or —SO$_2$N($R^5$)—, or G optionally bind together with $R^5$ and $R^6$ to form a ring, or with the proviso that when $R^1$ and $R^2$ or two $R^2$ bound to the neighboring atoms exist, these $R^1$ and $R^2$ or two $R^2$ optionally bind together to form a ring; respectively, or a prodrug thereof, or a pharmaceutically acceptable salt thereof;

[2] an (aza)indole derivative as described in the above [1], wherein $X^1$, $X^2$ and $X^3$ independently represent $CR^2$ with the proviso that when two or more $R^2$ exist, these $R^2$ are optionally the same or different from each other, or a prodrug thereof, or a pharmaceutically acceptable salt thereof;

[3] an (aza)indole derivative as described in the above [1] or [2], wherein T represents cyano, or a prodrug thereof, or a pharmaceutically acceptable salt thereof;

[4] an (aza)indole derivative as described in any one of the above [1] to [3], wherein Q represents carboxy, or a prodrug thereof, or a pharmaceutically acceptable salt thereof;

[5] an (aza)indole derivative as described in any one of the above [1] to [4], wherein Y represents a hydrogen atom, hydroxy or a halogen atom, or a prodrug thereof or a pharmaceutically acceptable salt thereof;

[6] an (aza)indole derivative as described in the above [5], wherein Y represents hydroxy, or a prodrug thereof, or a pharmaceutically acceptable salt thereof;

[7] an (aza)indole derivative as described in any one of the above [1] to [6], wherein ring J represents a benzene ring, or a prodrug thereof, or a pharmaceutically acceptable salt thereof;

[8] an (aza)indole derivative as described in the above [4], wherein the group represented by the general formula:

[Chem. 2]

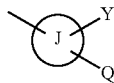

(II)

is a group represented by the following general formula (IIa):

[Chem. 3]

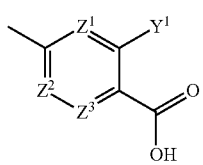

(IIa)

in the formula, $Z^1$, $Z^2$ and $Z^3$ independently represent $CR^7$ or N; and $Y^1$ and $R^7$ independently represent a hydrogen atom, hydroxy, amino, a halogen atom, lower alkyl or lower alkoxy with the proviso that when two or more $R^7$ exist, these $R^7$ are optionally the same or different from each other, or a prodrug thereof, or a pharmaceutically acceptable salt thereof;

[9] an (aza)indole derivative as described in the above [8], wherein $Z^1$ and $Z^3$ represent CH, and $Z^2$ represent $CR^8$ or N; and $Y^1$ and $R^8$ independently represent a hydrogen atom, hydroxy or a halogen atom, or a prodrug thereof, or a pharmaceutically acceptable salt thereof;

[10] an (aza)indole derivative as described in any one of the above [4] to [6], wherein ring J represents a 5-membered heteroaryl ring having 1 to 3 different or the same hetero atoms selected from the group consisting of an oxygen atom, a nitrogen atom and a sulfur atom in the ring with the proviso that an oxygen atom and a sulfur atom do not exist next to each other; and Y represents a hydrogen atom, hydroxy, amino, a halogen atom, optionally substituted lower alkyl or optionally substituted lower alkoxy with the proviso that two or more Y optionally exits on ring J and these J are optionally the same or different from each other, or a prodrug thereof, or a pharmaceutically acceptable salt thereof;

[11] an (aza)indole derivative as described in the above [10], wherein the group represented by the general formula:

[Chem. 4]

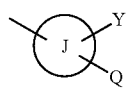

(II)

is a group represented by the following general formula (IIb):

[Chem. 5]

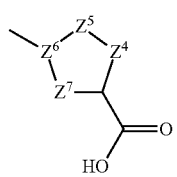

(IIb)

in the formula, $Z^4$, $Z^5$ and $Z^7$ represent an oxygen atom, a nitrogen atom, a sulfur atom with the proviso that both of $Z^4$ and $Z^5$ are not atoms selected from an oxygen atom and a sulfur atom at the same time, or $CR^9$ in which $R^9$ represents a hydrogen atom, hydroxy, amino, a halogen atom, lower alkyl or lower alkoxy with the proviso that when two or more $R^9$ exist, these $R^9$ are optionally the same or different from each other; $Z^6$ represents a carbon atom; and $Z^4$, $Z^5$, $Z^6$ and $Z^7$ bind together with the carbon atom bound by a carboxy group to form a 5-membered heteroaryl ring, or a prodrug thereof, or a pharmaceutically acceptable salt thereof;

[12] an (aza)indole derivative as described in the above [4], wherein the group represented by the general formula:

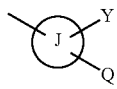

is a group represented by the following general formula (IId):

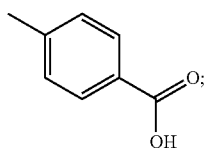

$R^1$ represents a hydrogen atom; $X^1$ represents $CR^{10}$ wherein $R^{10}$ represents lower alkyl or —O-(lower alkyl)-; $X^2$ represents $CR^{11}$ wherein $R^{11}$ represents a halogen atom or lower alkyl; and $X^3$ represents CH; or a prodrug thereof, or a pharmaceutically acceptable salt thereof;

[13] an (aza)indole derivative as described in the above [12], wherein $R^{10}$ represents methyl or methoxy; and $R^{11}$ represents a fluorine atom, a chlorine atom or methyl; or a prodrug thereof, or a pharmaceutically acceptable salt thereof, an (aza)indole derivative as described in the above [12], or a prodrug thereof, or a pharmaceutically acceptable salt thereof;

[14] a xanthine oxidase inhibitor comprising as an active ingredient an (aza)indole derivative as described in any one of the above [1] to [13], or a prodrug thereof; or a pharmaceutically acceptable salt thereof;

[15] a pharmaceutical composition comprising as an active ingredient an (aza)indole derivative as described in any one of the above [1] to [13], or a prodrug thereof, or a pharmaceutically acceptable salt thereof;

[16] a pharmaceutical composition as described in the above [15], which is an agent for the prevention or treatment of a disease selected from the group consisting of hyperuricemia, gouty tophus, gouty arthritis, renal disorder associated with hyperuricemia and urinary calculi;

[17] a pharmaceutical composition as described in the above [16], which is an agent for the prevention or treatment of hyperuricemia;

[18] a pharmaceutical composition as described in the above [15], which is an agent for lowering serum uric acid level;

[19] a pharmaceutical composition as described in the above [15], which is a uric acid production inhibitor;

[20] a pharmaceutical composition as described in any one of the above [15] to [19] which comprises a further combination with at least one drug selected from the group consisting of colchicines, a non-steroid anti-inflammatory drug, a steroid and a urine alkalizer as an active ingredient; and the like.

In the (aza)indole derivatives represented by the above general formula (I) of the present invention, each term has the following meaning.

The term "halogen atom" means a fluorine atom, a chlorine atom, a bromine atom or an iodine atom.

The term "lower" means a straight-chained or a branched hydrocarbon group having 6 or less carbon atoms. For example, as lower alkyl, methyl, ethyl, propyl, isopropyl, butyl, isobutyl, sec-butyl, tert-butyl, pentyl, isopentyl, neopentyl, tert-pentyl, hexyl and the like can be illustrated, as lower alkenyl, vinyl, allyl, 1-propenyl, isopropenyl, 1-butenyl, 2-butenyl, 2-methylallyl and the like can be illustrated, and as lower alkynyl, ethynyl, 2-propynyl and the like can be illustrated. As lower alkylene, methylene, methylmethylene, dimethylmethylene, ethylene, 1-methylethylene, 2-methylethylene, propane-1,3-diyl, 1-methylpropane-1,3-diyl, 1,1-dimethylpropane-1,3-diyl, 2-methylpropane-1,3-diyl, 2,2-dimethylpropane-1,3-diyl, 3-methylpropane-1,3-diyl, 3,3-dimethylpropane-1,3-diyl, butane-1,4-diyl, 1-methylbutane-1,4-diyl, 1,1-dimethylbutane-1,4-diyl, 2,2-dimethylbutane-1,4-diyl, 3,3-dimethylbutane-1,4-diyl, 4-methylbutane-1,4-diyl, 4,4-dimethylbutane-1,4-diyl, pentane-1,5-diyl, 1-methylpentane-1,5-diyl, 2-methylpentane-1,5-diyl, 3-methylpentane-1,5-diyl, 4-methylpentane-1,5-diyl, 5-methylpentane-1,5-diyl, hexane-1,5-diyl and the like can be illustrated, as lower alkenylene, vinylene, propene-1,3-diyl, 1-butene-1,4-diyl, 2-butene-1,4-diyl, 1,3-butadiene-1,4-diyl, 1-pentene-1,5-diyl, 2-pentene-1,5-diyl, 1,3-pentadiene-1,5-diyl, 1-hexene-1,6-diyl, 2-hexene-1,6-diyl, 3-hexene-1,6-diyl, 1,3-hexadiene-1,6-diyl, 1,3,5-hexatriene-1,6-diyl and the like can be illustrated, and as lower alkynylene, ethylene, 2-propynylene and the like can be illustrated. As lower alkoxy, methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy and the like can be illustrated, and as lower alkoxycarbonyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl and the like can be illustrated.

The term "perfluoro(lower alkyl)" means the above lower alkyl which is substituted by a fluorine atom, and methyl substituted by 1 to 3 fluorine atoms or ethyl substituted by 1 to 5 fluorine atoms is preferable.

The term "cycloalkyl" means cyclopropyl, cyclobutyl, cyclopentyl, cyclohexyl, cycloheptyl or cyclooctyl, and the term "cycloalkylene" means a divalent group derived from the above cycloalkyl.

The term "heterocycloalkyl" means a 3 to 8-membered aliphatic monocyclic hydrocarbon group having any 1 or 2 hetero atoms selected from the group consisting of an oxygen atom, a sulfur atom and a nitrogen atom in the ring and optionally having 1 or 2 oxo groups such as aziridino, azetidino, morpholino, 2-morpholinyl, thiomorpholino, 1-pyrrolidinyl, piperidino, 4-piperidinyl, 1-piperazinyl, 1-pyrrolyl, tetrahydrofuranyl, tetrahydropyranyl and the like, or a 5 to 6-membered aliphatic monocyclic hydrocarbon group defined above which is fused with a benzene ring, for example, 1,3-dioxoisoindolin-2-yl and the like, and the term "heterocycloalkylene" means a divalent group derived from the above heterocycloalkyl.

The term "aryl" means phenyl or naphthyl, and the term "arylene" means a divalent group derived from the above aryl.

The term "cycloalkyl(lower alkyl)" means the above lower alkyl substituted by the above cycloalkyl, the term "heterocycloalkyl(lower alkyl)" means the above lower alkyl substituted by the above heterocycloalkyl, the term "aryl(lower alkyl)" means the above lower alkyl substituted by the above aryl, the term "heteroaryl(lower alkyl)" means the above lower alkyl substituted by the above heteroaryl. A substituent of optionally substituted cycloalkyl(lower alkyl) may be on either cycloalkyl or lower alkyl. It is similar about optionally substituted heterocycloalkyl(lower alkyl), optionally substituted aryl(lower alkyl), and optionally substituted heteroaryl (lower alkyl).

The term "heteroaryl" means a 5 or 6-membered aromatic heterocyclic group having any 1 to 4 hetero atoms selected from the group consisting of an oxygen atom, a sulfur atom and a nitrogen atom in the ring, which is derived from thiazole, oxazole, isothiazole, isoxazole, pyridine, pyrimidine, pyrazine, pyridazine, pyrrole, furan, thiophene, imidazole, pyrazole, oxadiazole, thiadiazole, triazole, tetrazole, furazan or the like, or a 5 or 6-membered aromatic heterocyclic group fused with a 6-membered ring having any 1 to 4 hetero atoms selected from the group consisting of an oxygen atom, a sulfur atom and a nitrogen atom, which is derived from indole, isoindole, benzofuran, isobenzofuran, benzothiophene, benzoxazole, benzothiazole, benzoisoxazole, benzoisothiazole, indazole, benzimidazole, quinoline, isoquinoline, phthalazine, quinoxaline, quinazoline, sinoline, indolizine, naphthyridine, pteridine or the like, and the term "heteroarylene" means a divalent group derived from the above heteroaryl.

The term "optionally substituted" means which may have the same or different 1 to 3 substituents.

As a substituent of optionally substituted lower alkyl, optionally substituted lower alkenyl, optionally substituted lower alkynyl, optionally substituted cycloalkyl or optionally substituted heterocycloalkyl, for example, a fluorine atom, perfluoro (lower alkyl), —$OW^1$, —$SW^1$, carboxy, sulfo, lower alkyl, lower alkylsulfonyl, lower alkoxycarbonyl, —$OCOW^2$, —$N(W^2)COW^3$, —$OCOOW^4$, —$N(W^2)COOW^4$, —$NHC(=NH)$—$NW^2W^3$, —$NW^2W^3$, —$CONW^2W^3$, —$N(W^5)CONW^6W_7$, —$N(W^2)SO_2W_5$, —$SO_2NW^2W^3$, —$SO_2W_4$; aryl which may have any 1 to 3 groups selected from the group consisting of a halogen atom, hydroxy, lower alkyl, lower alkoxy and trifluoromethyl; and heteroaryl which may have any 1 to 3 groups selected from the group consisting of a halogen atom, hydroxy, lower alkyl, lower alkoxy and trifluoromethyl can be illustrated. As a substituent of optionally substituted lower alkyl in Y, a fluorine atom, perfluoro(lower alkyl), lower alkyl, a hydroxyl group and lower alkoxy can be preferably illustrated.

As a substituent of optionally substituted lower alkoxy, a fluorine atom, perfluoro(lower alkyl), lower alkyl, hydroxyl group and lower alkoxy can be preferably illustrated.

As a substituent of optionally substituted aryl and optionally substituted heteroaryl, for example, a halogen atom, perfluoro(lower alkyl), cyano, nitro, —$OW^8$, —$SW^8$, carboxy, lower alkyl, lower alkylsulfonyl, lower alkoxycarbonyl, —$OCOW^2$, —$N(W^2)COW^3$, —$OCOOW^4$, —$N(W^2)COOW^4$, —$NHC(=NH)$—$W^2W_3$, —$NW^2W_3$, —$CONW^2W_3$, —$N(W^5)CONW^6W^7$, —$N(W^2)SO_2W^5$, —$SO_2NW^2W^3$, —$SO_2W^4$; aryl which may have any 1 to 3 groups selected from the group consisting of a halogen atom, hydroxy, lower alkyl, lower alkoxy and trifluoromethyl; and heteroaryl which may have any 1 to 3 groups selected from the group consisting of a halogen atom, hydroxy, lower alkyl, lower alkoxy and trifluoromethyl, can be illustrated.

In the above, $W^1$ represents a hydrogen atom, lower alkyl, perfluoro(lower alkyl); aryl which may have any 1 to 3 groups selected from the group consisting of a halogen atom, hydroxy, alkyl, lower alkoxy and trifluoromethyl; aryl(lower alkyl); or lower alkyl having 2 to 6 carbon atoms which has a group selected from the group consisting of amino, mono(di) (lower alkyl)amino and lower alkylsulfonamide, with the proviso that the oxygen or sulfur atom bound to $W^1$ and a nitrogen atom in $W^1$ bind to different carbon atoms;

$W^2$, $W^3$, $W^5$, $W^6$ and $W^7$ independently represent a hydrogen atom, lower alkyl, aryl(lower alkyl), or $W^2$ and $W^3$, and $W^5$ and $W^6$, or $W^6$ and $W^7$ may form an alicyclic amino with the binding nitrogen atom;

$W^4$ represents lower alkyl, or $W^2$ and $W^4$ may form an alicyclic amino with the binding nitrogen atom;

and $W^8$ represents a hydrogen atom, lower alkyl, perfluoro (lower alkyl); aryl which may have any 1 to 3 groups selected from the group consisting of a halogen atom, hydroxy, alkyl, lower alkoxy and trifluoromethyl; aryl(lower alkyl); or lower alkyl having 2 to 6 carbon atoms which has a group selected from the group consisting of amino, mono(di)(lower alkyl) amino and lower alkylsulfonamide, with the proviso that the oxygen or sulfur atom bound to $W^8$ and a nitrogen atom in $W^8$ bind to different carbon atoms and when two —$OW^8$ exist on neighboring carbon atoms in an aryl ring, these $W^8$ may bind together to form a methylene chain which may be substituted by 1 or 2 fluorine atoms or an ethylene chain which may be substituted by 1 to 4 fluorine atoms, respectively.

The term "mono(di)(lower alkyl)amino" means amino mono- or di-substituted by the above lower alkyl, and the term "mono(di)(lower alkyl)carbamoyl" means carbamoyl mono- or di-substituted by the above lower alkyl. The two lower alkyl groups in a di-substituted group may be different from each other.

The term "alicyclic amino" means 3 to 8-membered cyclic amino optionally having a hetero atom selected from the group consisting of an oxygen atom, a sulfur atom and a nitrogen atom other than a nitrogen atom at the binding position in the ring, such as aziridino, azetidino, morpholino, thiomorpholino, 1-pyrrolidinyl, piperidino, 1-piperazinyl, 1-pyrrolyl and the like, optionally having 1 or 2 oxo groups and optionally having 1 or 2 double bonds in the ring, for example, 2-oxo-1-pyrrolidinyl and the like.

A ring G and either of $R^5$ and $R^6$, or $R^1$ and $R^2$, or two $R^2$ optionally bind together to form represents optionally substituted cycloalkyl or optionally substituted heterocycloalkyl, each of which may have 1 to 3 oxo groups on the ring and 1 or 2 double bonds in the ring, respectively.

In the formula (I), as $R^1$, a halogen atom, cyano, a hydrogen atom, hydroxy, —O-(optionally substituted lower alkyl), optionally substituted lower alkyl, optionally substituted aryl or the like is preferable, a halogen atom, a hydrogen atom, hydroxy, lower alkoxy, lower alkyl or the like is more preferable. In $X^1$ or $X^2$, as $CR^2$, a halogen atom, cyano, trifluoromethyl, a hydrogen atom, hydroxy, carboxy, mono(di)lower alkyl)amino, optionally substituted lower alkyl, optionally substituted lower alkenyl, cycloalkyl, cycloalkyl(lower alkoxy), optionally substituted aryl, optionally substituted heteroaryl, —O-(optionally substituted lower alkyl), —CO-(optionally substituted heterocycloalkyl), —$CON(R^3)$-(optionally substituted lower alkyl), —$N(R^3)SO_2$— (lower alkyl), —O-(lower alkylene)-N($R^5$)COO-(optionally substituted lower alkyl) wherein $R^3$ and $R^5$ have the same meanings as defined in the above [1] or the like is preferable, a halogen atom, a hydrogen atom, hydroxy, lower alkyl, lower alkoxy or the like is more preferable; and in $X^3$, a halogen atom, a hydrogen atom, lower alkyl or the like is preferable, and a halogen atom or a hydrogen atom is more preferable.

In the (aza)indole derivatives represented by the general formula (I), in case that the group represented by the above formula (II) is a group represented by the following formula (II) wherein $Q^C$ represents carboxy or 5-tetrazoyl; $X^1$ and $X^2$ independently represent $CR^2$; and among $R^1$ and two $R^2$, any two of them represent a hydrogen atom, and the other represents a hydrogen atom, lower alkyl, perfluoro(lower alkyl), a halogen atom, cyano or lower alkoxy, as Y, hydroxy, amino, a halogen atom, nitro, optionally substituted lower alkyl or optionally substituted lower alkoxy is preferable with the proviso that two or more Y optionally exits on ring J and these Y are optionally different from each other, and hydroxy or amino is more preferable.

[Chem. 8]

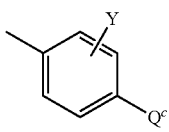

(IIc)

A preferable compound among the (aza)indole derivatives represented by the above general formula (I) of the present invention also has a URAT1 inhibitory activity. Accordingly, such a compound can exert an uricosuric effect in addition to an uric acid synthesis inhibitory effect, and show a superior lowering effect of serum uric acid level. As a compound which also has a URAT1 inhibitory activity, for example, an indole derivative represented by the following general formula (IA) can be illustrated.

[Chem. 9]

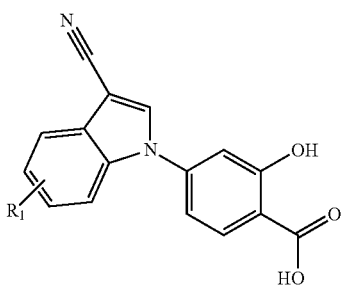

(IA)

In the formula, $R^1$ have the same meaning as defined above.

In other aspect, as a preferable compound which also has a URAT1 inhibitory activity and exerts excellent pharmacokinetic, for example, an indole derivative represented by the following general formula (IB) can be illustrated.

[Chem. 10]

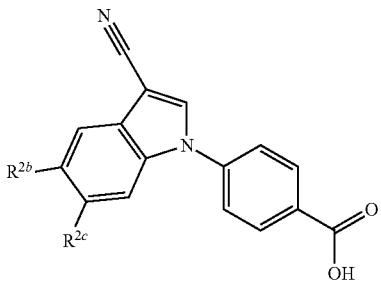

(IB)

In the formula, $R^{2b}$ represents lower alkyl or lower alkoxy, and methyl or methoxy is preferable. $R^{2c}$ represents a halogen atom or lower alkyl, and a fluorine atom, a chlorine atom or methyl is preferable.

The (aza)indole derivatives represented by the above general formula (I) of the present invention can be prepared, for example, by a method described below or a similar method thereto, or a method described in literatures or a similar method thereto and the like. In addition, when a protective group is necessary, operations of introduction and deprotection can be conducted optionally in combination according to a general method.

[Chem. 11]

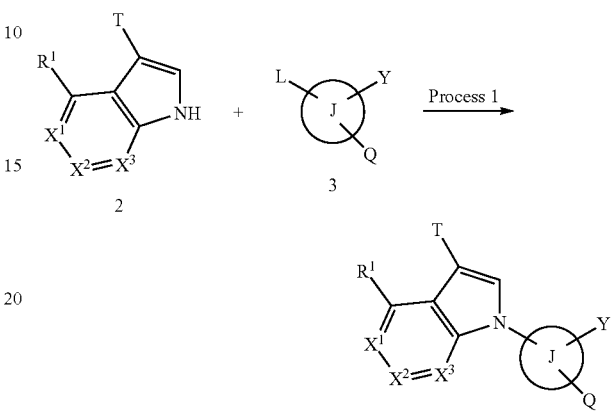

In the formula, L represents a halogen atom and T, ring J, Q, Y, $X^1$ to $X^3$ and $R^1$ have the same meanings as defined above.

Process 1

An (aza)indole derivative represented by the above general formula (I) of the present invention can be prepared by conducting a coupling reaction of Compound (2) and Compound (3) in an inert solvent or without any solvent in the presence of a base and optionally removing a protective group. As the inert solvent, N,N-dimethylformamide, tetrahydrofuran, N-methylpyrolidone, 1,2-dimethoxyethane, dimethylsulfoxide, 1,2-diethoxyethane, 1,4-dioxane, a mixed solvent thereof and the like can be illustrated. As the base, sodium hydride, potassium carbonate, cesium carbonate, sodium hydroxide, potassium hydroxide, sodium methoxide and the like can be illustrated. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

An (aza)indole derivative represented by the above general formula (I) of the present invention can be also prepared by conducting a coupling reaction of Compound (2) and Compound (3) in an inert solvent in the presence of a base, a catalytic amount of copper iodide and a ligand and optionally removing a protective group. As the inert solvent, N,N-dimethylformamide, tetrahydrofuran, N-methylpyrrolidinone, 1,2-dimethoxyethane, dimethylsulfoxide, a mixed solvent thereof and the like can be illustrated. As the base, potassium phosphate, potassium carbonate, cesium carbonate and the like can be illustrated. As the ligand, N,N-dimethylethylenediamine, (1R,2R)-(−)-N,N'-dimethylcyclohexane-1,2-diamine, (1S,2S)-(+)-N,N'-dimethylcyclohexane-1,2-diamine, proline, N,N-dimethylaminoglycine and the like can be illustrated. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted by using a pressure-resistant reaction container.

The above reaction can be also conducted by a method described in the following literature (a).

(a) Hui Zhang; Qian Cai; and Dawei Ma, J. Org. Chem., Vol. 70, No. 13, 2005, 5173.

[Chem. 12]

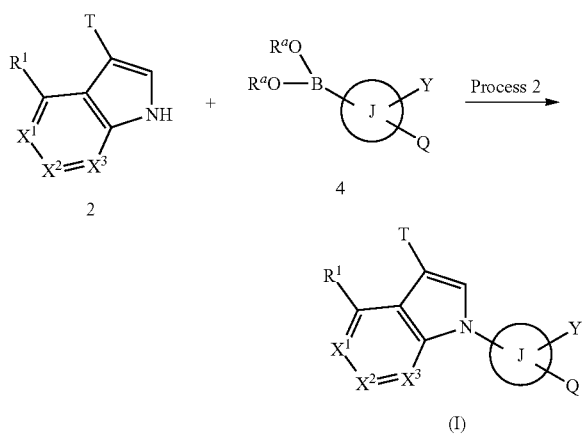

In the formula, $R^a$ represents a hydrogen atom or lower alkyl with the proviso that two $R^a$ may be different and both $R^a$ may bind together to form a ring, and T, ring J, Q, Y, $X^1$ to $X^3$ and $R^1$ have the same meanings as defined above.

Process 2

An (aza)indole derivative represented by the above general formula (I) of the present invention can be also prepared by conducting a coupling reaction of Compound (2) and Compound (4) in an inert solvent in the presence of a base and a catalytic amount of copper acetate and optionally removing a protective group. As the inert solvent, dichloromethane, 1,2-dichloroethane, N,N-dimethylformamide, tetrahydrofuran, N-methylpyrolidone, 1,2-dimethoxyethane, a mixed solvent thereof and the like can be illustrated. As the base, triethylamine, N,N-diisopropylethylamine, pyridine, 2,6-lutidine and the like can be illustrated. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

Among the (aza)indole derivatives represented by the above general formula (I) of the present invention, Compound (Ia) wherein Q represents carboxy can be also prepared, for example, by Synthetic method 2.

[Synthetic Method 2]

[Chem. 13]

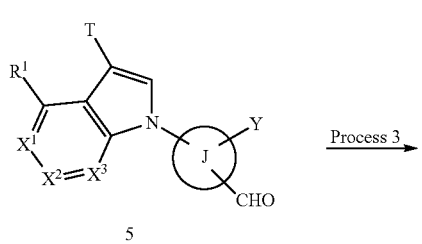

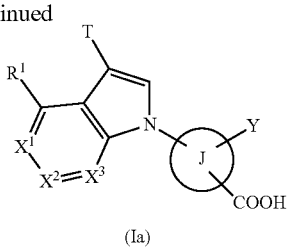

In the formula, T, ring J, Y, $X^1$ to $X^3$ and $R^1$ have the same meanings as defined above.

Process 3

An (aza)indole derivative (Ia) of the present invention can be also prepared by allowing Aldehyde compound (5) to react with an oxidant in an inert solvent in the presence or absence of a base. As the inert solvent, dichloromethane, 1,4-dioxane, acetonitrile, acetone, hexane, cyclohexane, t-butanol, water, a mixed solvent thereof and the like can be illustrated. As the base, sodium hydroxide, potassium hydroxide, lithium hydroxide and the like can be illustrated. As the oxidant, potassium permanganate, barium permanganate, silver oxide and the like can be illustrated. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

Among the (aza)indole derivatives represented by the above general formula (I) of the present invention, Compound (Ib) wherein T represents cyano can be also prepared, for example, by Synthetic method 3.

[Synthetic Method 3]

[Chem. 14]

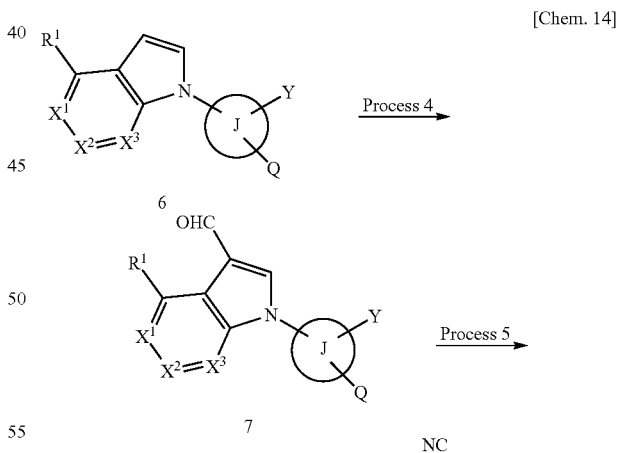

In the formula, ring J, Q, Y, $X^1$ to $X^3$ and $R^1$ have the same meanings as defined above.

Process 4

Aldehyde compound (7) can be prepared by subjecting Compound (6) to formylation in an inert solvent in the presence of N,N-dimethylformamide and phosphoryl chloride. As the inert solvent, N,N-dimethylformamide, acetonitrile, benzene, toluene, chlorobenzene, dichloromethane, 1,2-dichloroethane, chloroform, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 5

An (aza)indole derivative (Ib) of the present invention can be also prepared by subjecting Aldehyde compound (7) to cyanation using hydroxylamine or a hydrochloride salt thereof in an inert solvent in the presence or absence of a base in the presence or absence of a condensation agent. As the inert solvent, N,N-dimethylformamide, acetonitrile, benzene, toluene, chlorobenzene, dichloromethane, 1,2-dichloroethane, chloroform, N-methylpyrrolidone a mixed solvent thereof and the like can be illustrated. As the base, triethylamine, N,N-diisopropylethylamine, pyridine, 2,6-lutidine, 1,8-diazabicyclo[5,4,0]-7-undecene, potassium carbonate, sodium carbonate and the like can be illustrated. As the condensation agent, acetic anhydride, thionyl chloride, phosphoric chloride, N,N'-dicyclohexylcarbodiimide, N,N'-carbonyldiimidazole and the like can be illustrated. The reaction temperature is usually at 0° C. to reflux temperature, and the reaction time is usually from 30 minutes to 7 days, varying based on a used starting material, solvent and reaction temperature or the like.

The above cyanation reaction may be also conducted by allowing Aldehyde compound (7) and hydroxylamine or a hydrochloride salt thereof to react with sodium formate in a formic acid solvent. The reaction temperature is usually at 0° C. to reflux temperature, and the reaction time is usually from 30 minutes to 7 days, varying based on a used starting material, solvent and reaction temperature or the like.

Among the (aza)indole derivatives represented by the above general formula (I) of the present invention, Compound (Ic) wherein $R^1$ or $R^2$ represents A-D-E-G with the proviso that A represents —O—, —S— or —N($R^3$)—, or —N(-D-E-G)$_2$, with the proviso that D represents lower alkylene, and E, G and $R^3$ have the same meanings as defined in the above can be also prepared, for example, by Synthetic method 4. In Synthetic method 4, as an example, it is described using an example wherein $R^1$ represents —O-$D^4$-E-G in which $D^4$ represents lower alkylene; $X^1$ to $X^3$ represent CH.

[Synthetic Method 4]

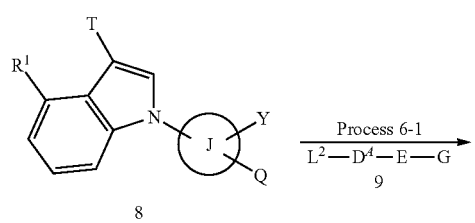

[Chem. 15]

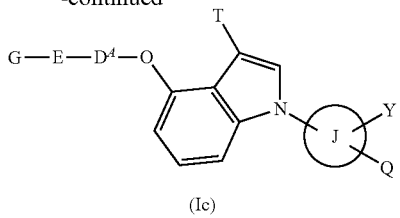

(Ic)

In the formula, $L^2$ represents a halogen atom, methansulfonyloxy, p-toluenesulfonyloxy or trifluoromethansulfonyloxy, and $D^4$, E, G, T, ring J, Q and Y have the same meanings as defined above.

Process 6-1

An (aza)indole derivative (Ic) of the present invention can be also prepared by alkylating Hydroxyindole compound (8) using Compound (9) in an inert solvent in the presence of a base and optionally in the presence of a phase transfer catalyst. As the inert solvent, diethyl ether, tetrahydrofuran, 1,4-dioxane, 1,2-dimethoxyethane, N,N-dimethylformamide, dimethylsulfoxide, N-methylpyrrolidone, benzene, toluene, dichloromethane, a mixed solvent thereof and the like can be illustrated. As the base, inorganic base of sodium carbonate, potassium carbonate, cesium carbonate, sodium hydride and the like, and organic base of triethylamine, N,N-diisopropylethylamine, pyridine, 2,6-lutidine, 1,8-diazabicyclo[5,4,0]-7-undecene and the like can be illustrated. As the phase transfer catalyst, tetra-n-butylammonium chloride, tetra-n-butylammonium bromide, 18-crown-6 and the like can be illustrated. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

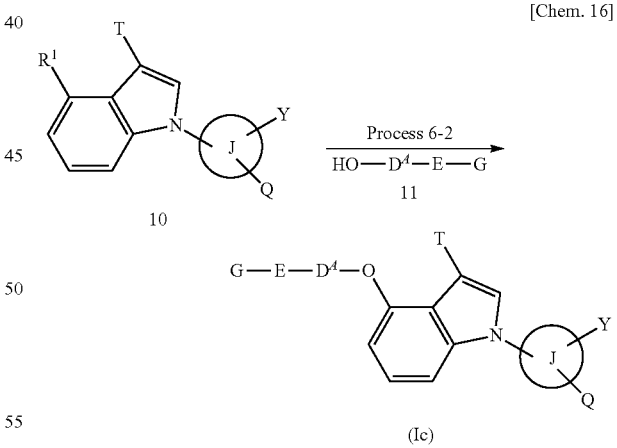

[Chem. 16]

In the formula, $D^4$, E, (3 T, ring J, Q and Y have the same meanings as defined above.

Process 6-2

An (aza)indole derivative (Ic) of the present invention can be also prepared by alkylating Compound (10) using Hydroxy compound (11) in an inert solvent in the presence of a condensation agent and a phosphorous compound. As the inert solvent, diethyl ether, tetrahydrofuran, 1,4-dioxane, 1,2-dimethoxyethane, N,N-dimethylformamide, dimethylsulfoxide, N-methylpyrrolidone, benzene, toluene, dichloromethane, a mixed solvent thereof and the like can be illustrated. As the condensation agent, ethyl azodicarboxylate, isopropyl azodicarboxylate, 1,1'-(azodicarbonyl)dipiperidine and the like can be illustrated. As the phosphorous compound, triphenylphosphine and the like can be illustrated. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

Among the (aza)indole derivatives represented by the above general formula (I) of the present invention, Compound (Id) wherein $R^1$ or $R^2$ represents -A-D-E-G with the proviso that A represents a single bond and D represents optionally substituted alkenylene with the proviso that a double bond exists next to A, optionally substituted arylene or optionally substituted heteroarylene, and E and G have the same meanings as defined above can be also prepared, for example, by Synthetic method 5. In Synthetic method 5, as an example, it is described using an example wherein $R^1$ represents -$A^B$-$D^B$-E-G wherein $A^B$ represents a single bond, $D^B$ represent optionally substituted alkenylene, optionally substituted arylene or optionally substituted heteroarylene; and $X^1$ to $X^3$ represent CH.

[Synthetic Method 5]

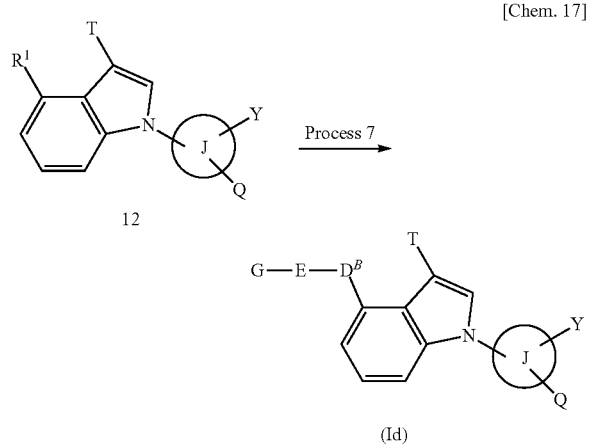

[Chem. 17]

In the formula, $L^4$ represents a halogen atom or trifluoromethansulfonyl, $D^B$ represents optionally substituted lower alkenylene, optionally substituted arylene or optionally substituted heteroarylene, and E, Q, T, ring J, Q and Y have the same meanings as defined above.

Process 7 [Method 1]

An (aza)indole derivative (Id) of the present invention can be also prepared by conducting Suzuki-Miyaura coupling of Compound (12) using the corresponding arylboronic acid reagent or a heteroarylboronic acid reagent in an inert solvent in the presence of a base and a palladium catalyst. As the inert solvent, benzene, toluene, xylene, diethyl ether, tetrahydrofuran, 1,4-dioxane, 1,2-dimethoxyethane, dichloromethane, 1,2-dichloroethane, chloroform, methanol, ethanol, 2-propanol, butanol, N,N-dimethylformamide, N-methylpyrolidone, dimethylsulfoxide, water, a mixed solvent thereof and the like can be illustrated. As the base, sodium carbonate, potassium carbonate, sodium hydroxide, potassium hydroxide, sodium ethoxide, sodium methoxide, potassium fluoride, cesium fluoride, triethylamine, N,N-diisopropyl-ethylamine, pyridine, 2,6-lutidine, 1,8-diazabicyclo[5,4,0]-7-undecene and the like can be illustrated. As the palladium catalyst, tetrakis(triphenylphosphine) palladium, dichlorobis(triphenylphosphine)palladium, [1,1'-bis(diphenylphosphino)ferrocene]-dichloropalladium and the like can be illustrated. The reaction temperature is usually at 0° C. to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

Process 7 [Method 2]

An (aza)indole derivative (Id) of the present invention can be also prepared by conducting Mizorogi-Heck reaction of Compound (12) using the corresponding alkene in an inert solvent in the presence of a base and a palladium catalyst. As the inert solvent, benzene, toluene, xylene, diethyl ether, tetrahydrofuran, 1,4-dioxane, 1,2-dimethoxyethane, dichloromethane, 1,2-dichloroethane, chloroform, methanol, ethanol, 2-propanol, butanol, N,N-dimethylformamide, N-methylpyrolidone, dimethylsulfoxide, water, a mixed solvent thereof and the like can be illustrated. As the base, triethylamine, N,N-diisopropylethylamine, pyridine, 2,6-lutidine, 1,8-diazabicyclo[5,4,0]-7-undecene and the like can be illustrated. As the palladium catalyst, palladium acetate, palladium chloride, tetrakis(triphenylphosphine) palladium, dichlorobis(triphenylphosphine)palladium, [1,1'-bis(diphenylphosphino)ferrocene]-dichloropalladium and the like can be illustrated. In addition, the present reaction can be also conducted using a ligand depending on the kind of a palladium catalyst, and as the ligand, triphenylphosphine, tri-o-tolylphosphine, tri-t-butylphosphonium tetrafluoroborate and the like can be illustrated. The reaction temperature is usually at 0° C. to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

The arylation or hetero arylation reaction of Process 7 (Method 1) can be also conducted, for example, by a method described in the following literatures (b) to (f).

(b) Anderson, K. W.; Buchwald, S. L. Angew Chem, Int Ed. 2005, 44 (38), 6173-6177.

(c) Appukkuttan, P.; Van Der Eycken, E. et al. Synlett 2005, (1), 127-133.

(d) Wang, W.; Xiong, C et al. Tetrahedron Lett. 2001, 42 (44), 7717-7719.

(e) Yang, Y.; Martin, A. R. Synth Commun 1992, 22 (12), 1757-1762.

(f) Billingsley, K. L.; Anderson, K. W.; Buchwald, S. L. Angew Chem, Int Ed 2006, 45 (21), 3484-3488.

The alkenylation reaction of Process 7 (Method 2) can be also conducted, for example, by a method described in the following literatures (g) to (i).

(g) Hassner, A.; Loew, D. et al. J Org. Chem. 1984, 49 (14), 2546.

(h) Leclerc, J.-P.; Andre, M. et al. J Org. Chem. 2006, 71 (4), 1711-1714.

(i) Harrison, C.-A.; Jackson, P. M. et al. J Chem Soc, Perkin Trans 1, 1995, (9), 1131-1136.

Among the raw materials (2) used in the above processes, Compound (2a) wherein T represents cyano can be commercially available, or prepared by a known method or a similar method thereto and the like. In addition, it can be prepared by the following method, a similar method thereto or the like.

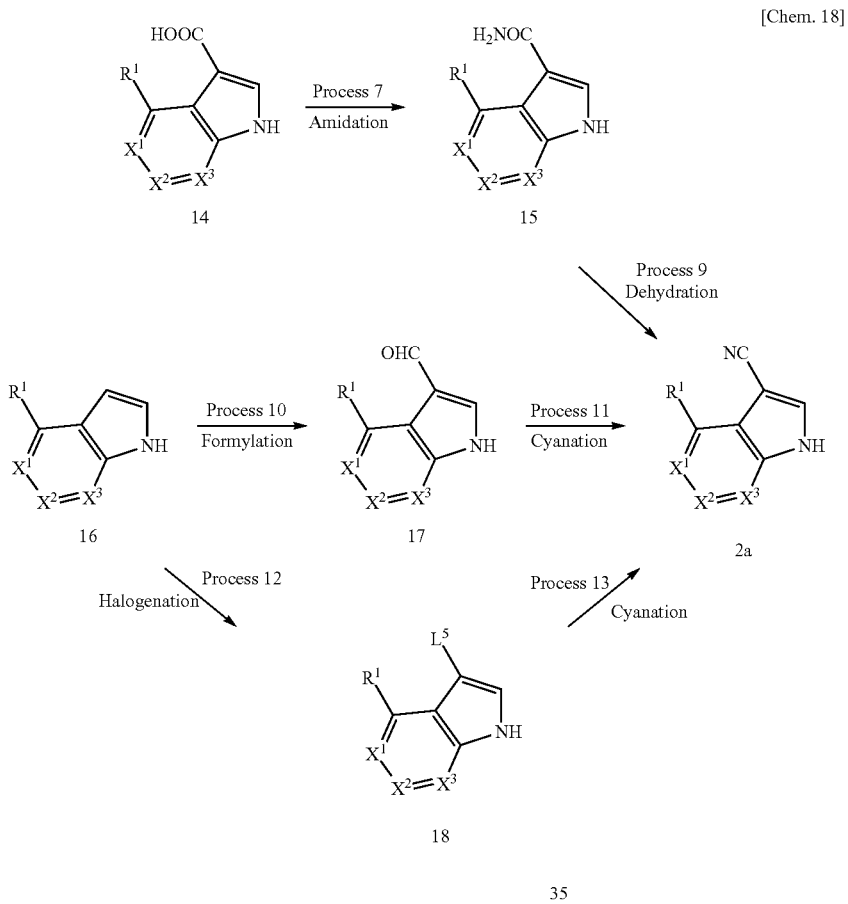

[Chem. 18]

In the formula, $L^5$ represents a halogen atom, $X^1$ to $X^3$ and $R^1$ have the same meanings as defined above.

Process 8

Amide compound (15) can be prepared by subjecting Carboxylic acid compound (14) and ammonia to amidation optionally using an additive such as 1-hydroxybenzotriazole or the like in an inert solvent in the presence or absence of a condensing agent in the presence or absence of a base. As the inert solvent, tetrahydrofuran, 1,4-dioxane, 1,2-dimethoxyethane, benzene, toluene, xylene, dichloromethane, 1,2-dichloroethane, chloroform, a mixed solvent thereof and the like can be illustrated. As the condensing agent, acetic anhydride, thionyl chloride, oxalyl chloride, N,N'-carbonyldiimidazole, N,N'-dicyclohexylcarbodiimide, diisopropylcarbodiimide, N-ethyl-N'-3-dimethylaminopropylcarbodiimide and hydrochloride salt thereof, diphenylphosphorylazide and the like can be illustrated. As the base, triethylamine, N,N-diisopropylethylamine, pyridine, 2,6-lutidine, 1,8-diazabicyclo-[5,4,0]-7-undecene and the like can be illustrated. The reaction temperature is usually at 0° C. to reflux temperature, and the reaction time is usually from 30 minutes to 7 days, varying based on a used starting material, solvent and reaction temperature or the like.

Process 9

Nitrile compound (2a) can be also prepared by dehydrating Amide compound (15) in an inert solvent in the presence of a dehydrating agent. As the inert solvent, tetrahydrofuran, 1,4-dioxane, 1,2-dimethoxyethane, N,N-dimethylformamide, acetonitrile, benzene, toluene, xylene, dichloromethane, 1,2-dichloroethane, chloroform, a mixed solvent thereof and the like can be illustrated. As the dehydrating agent, acetic anhydride, thionyl chloride, phosphoryl chloride, methanesulfonylimidazole, p-toluenesulfonylchloride, N,N'-dicyclohexylcarbodiimide, diphosphorus pentoxide, triphosgene and the like can be illustrated. The reaction temperature is usually at 0° C. to reflux temperature, and the reaction time is usually from 30 minutes to 7 days, varying based on a used starting material, solvent and reaction temperature or the like.

Process 10

Aldehyde compound (17) can be also prepared by subjecting Compound (16) to formylation by a method similar to that as described in the above Process 4.

Process 11

Nitrile compound (2a) can be also prepared by subjecting Aldehyde compound (17) to cyanation by a method similar to that as described in the above Process 5.

Process 12

Halogeno compound (18) can be prepared by subjecting Compound (16) to halogenation in an inert solvent in the presence of a halogenating agent. As the inert solvent, tetrahydrofuran, 1,4-dioxane, acetic acid, dichloromethane, 1,2-dichloroethane, chloroform, a mixed solvent thereof and the like can be illustrated. As the halogenating agent, bromine, N-bromosuccinimide, pyridinium bromideperbromide, iodine and the like can be illustrated. The reaction temperature is usually at 0° C. to reflux temperature, and the reaction time is usually from 30 minutes to 7 days, varying based on a used starting material, solvent and reaction temperature or the like.

Process 13

Nitrile compound (2a) can be also prepared by subjecting Halogeno compound (18) to cyanation in an inert solvent in the presence of a cyanation reagent, a base and a palladium catalyst. As the inert solvent, benzene, toluene, xylene, diethyl ether, tetrahydrofuran, 1,4-dioxane, 1,2-dimethoxyethane, dichloromethane, 1,2-dichloroethane, chloroform, methanol, ethanol, 2-propanol, butanol, N,N-dimethylformamide, N-methylpyrolidone, dimethylsulfoxide, water, a mixed solvent thereof and the like can be illustrated. As the cyanation reagent, sodium cyanide, potassium cyanide, copper cyanide, zinc cyanide, trimethylsilyl cyanide and the like can be illustrated. As the base, sodium carbonate, potassium carbonate, sodium hydroxide, potassium hydroxide, sodium ethoxide, sodium methoxide, potassium fluoride, cesium fluoride, triethylamine, N,N-diisopropylethylamine, pyridine, 2,6-lutidine, 1,8-diazabicyclo[5,4,0]-7-undecene and the like can be illustrated. As the palladium catalyst, tetrakis(triphenylphosphine) palladium, dichlorobis(triphenylphosphine)palladium, [1,1'-bis(diphenylphosphino)-ferrocene] dichloropalladium and the like can be illustrated. The reaction temperature is usually at 0° C. to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

The cyanation reaction of Process 13 can be also conducted, for example, by a method described in the following literature (j), a similar method thereto or the like.

(j) Sakamoto, T.; Ohsawa, K.; J Chem Soc, Perkin Trans 1 1999, (16), 2323-2326.

The raw materials (16) used in the above processes can be commercially available, or prepared, for example, by a method described in the following literatures (k) to (n), a similar method thereto or the like.

(k) Rege, Pankaj D.; Tian, Yuan; Corey, E. J. Organic Letters, 2006, 8 (14), 3117-3120.

(l) Wang, Jianji; Soundarajan, Nachimuthu; et al. Tetrahedron Letters, 2005, 46 (6), 907-910.

(m) Cacchi, Sandro; Fabrizi, Giancarlo; Parisi, Luca M. Organic Letters, 2003, 5 (21), 3843-3846.

(n) Bosco, Marcella; Dalpozzo, Renato; Bartoli, et al. Journal of the Chemical Society, Perkin Transactions 2: Physical Organic Chemistry, 1991, (5), 657-63.

In addition, it can be also prepared by a method shown in the following Synthetic method 6, a similar method thereto or the like.

[Synthetic Method 6]

[Chem. 19]

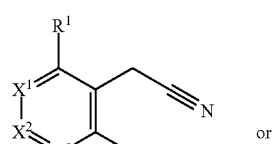

19 or

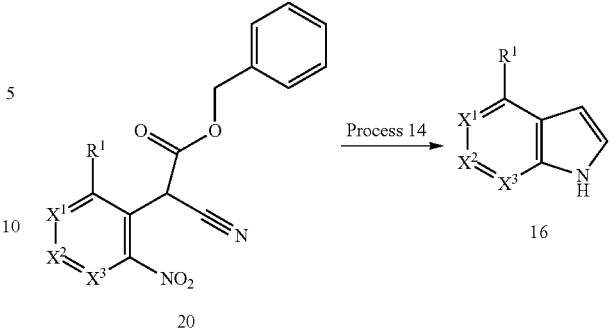

20

In the formula, $X^1$ to $X^3$ and $R^1$ have the same meanings as defined above.

Process 14

Indole compound (16) can be also prepared by allowing Nitrobenzene derivative (19) or (20) to react using a metallic catalyst under an ordinary pressure or a pressure under a hydrogen atmosphere in an inert solvent. As the inert solvent, methanol, ethanol, n-butanol, acetic acid, ethyl acetate, tetrahydrofuran, N,N-dimethylformamide, acetonitrile, water, a mixed solvent thereof and the like can be illustrated. As the metallic catalyst, palladium carbon, rhodium carbon, platinum oxide(IV) and the like can be illustrated. The reaction temperature is usually at 0° C. to reflux temperature, and the reaction time is usually from 1 hour to 7 days, varying based on a used starting material, solvent and reaction temperature or the like.

As the protective groups to be used in the present invention, various protective group generally used in organic reactions can be used. For example, as the protective groups of a hydroxyl group, in addition to a p-methoxybenzyl group, a benzyl group, a methoxymethyl group, an acetyl group, a pivaloyl group, a benzoyl group, a tert-butyldimethylsilyl group, a tert-butyldiphenylsilyl group, an allyl group and the like, when two hydroxyl groups are adjacent, an isopropylidene group, a cyclopentylidene group, a cyclohexylidene group and the like can be illustrated. As the protective groups of a thiol group, a p-methoxybenzyl group, a benzyl group, an acetyl group, a pivaloyl group, a benzoyl group, a benzyloxycarbonyl group and the like can be illustrated. As the protective groups of an amino group, a benzyloxycarbonyl group, a tert-butoxycarbonyl group, a benzyl group, a p-methoxybenzyl group, a trifluoroacetyl group, an acetyl group, a phthaloyl group and the like can be illustrated. As the protective groups of a carboxy group, a lower alkyl group, a benzyl group, a tert-butyldimethylsilyl group, an allyl group and the like can be illustrated.

A compound represented by the above general formula (I) of the present invention can be isolated or purified by conventional isolation techniques, such as fractional recrystallization, purification by chromatography, solvent extraction, solid-phase extraction and the like.

The (aza)indole derivatives represented by the above general formula (I) of the present invention can be converted into pharmaceutically acceptable salts thereof in the usual way. As such a salt, an acid additive salt with a mineral acid such as hydrochloric acid, hydrobromic acid, hydroiodic acid, sulfuric acid, nitric acid, phosphoric acid and the like, an acid additive salt with an organic acid such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like, an inorganic salt such as a sodium salt, a potassium salt, a calcium salt, a magnesium salt, a zinc salt, a lithium salt, an aluminum salt and the like, a salt with an organic amine such as N-methyl-D-glucamine, N,N'-dibenzylethylenediamine, 2-aminoethanol, tris(hydroxymethyl)aminomethane, arginine, lysine, piperadine, choline, diethylamine, 4-phenylcyclohexane and the like can be illustrated.

Of the (aza)indole derivatives represented by the above general formula (I) of the present invention, in a compound having an unsaturated bond there are two geometrical isomers, a compound of cis (Z) form and a compound of trans (E) form. In the present invention, either of the compounds can be employed, and a mixture thereof can be also employed.

Of the (aza)indole derivatives represented by the above general formula (I) of the present invention, in a compound having a chiral carbon atom, there are a compound of R form and a compound of S form for each chiral carbon. In the present invention, either of the optical isomers can be employed, and a mixture of the optical isomers thereof can be also employed.

Of the (aza)indole derivatives represented by the above general formula (I) of the present invention, there can be some tautomers, the compounds of the present invention also include these tautomers.

In the present invention, the term "prodrug" means a compound modified from a parent compound by a pharmaceutically acceptable group usually used in a prodrug, for example, which is given a property such as improvement of stability, substantivity, oral absorbability or the like, and can be expected to be converted into the parent compound within an organism (in the liver, the intestine and the like) to exert the effect. A prodrug of a compound represented by the above general formula (I) of the present invention can be prepared by introducing an appropriate group forming a prodrug into any one or more groups selected from a hydroxy group, an amino group, a carboxy group and other groups which can form a prodrug of the compound represented by the above general formula (I) using a corresponding reagent to produce a prodrug such as a halide compound or the like in the usual way, and then by suitably isolating and purifying in the usual way as occasion demands. *Gekkan-Yakuji iyakuhin tekiseisiyou no tameno rinsyou yakubutudoutai* (monthly pharmaceutical, clinical pharmacokinetics for the proper use of pharmaceutical products), 2003.3. extra number Vol 0.42, No. 4, p. 669-707, *New drug Drug delivery system* Published by CMC Co., Ltd., 2000.1.31., p. 67-173. As a group forming a prodrug used in a hydroxy group or an amino group, for example, (lower alkyl)-CO— such as acetyl, propionyl, butylyl, isobutylyl, pivaloyl and the like; aryl-CO— such as benzoyl; (lower alkyl)-O-(lower alkylene)-CO—; (lower alkyl)-OCO-(lower alkylene)-CO—; (lower alkyl)-OCO— such as methyloxycarbonyl, ethyloxycarbonyl, propyloxycarbonyl, isopropyloxycarbonyl, tert-butyloxycarbonyl and the like; (lower alkyl)-O-(lower alkylene)-OCO—; (lower alkyl)-COO-(lower alkylene) such as acetyloxymethyl, pivaloyloxymethyl, 1-(acetyloxy)ethyl, 1-(pivaloyloxy)ethyl and the like; (lower alkyl)-OCOO-(lower alkylene) such as methoxycarbonyloxymethyl, 1-(methoxycarbonyloxy)ethyl, ethoxycarbonyloxymethyl, 1-(ethoxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; cycloalkyl-OCOO-(lower alkylene) such as cyclohexyloxycarbonyloxymethyl, 1-(cyclohexyloxycarbonyl)ethyl and the like; an ester or an amide with an amino acid such as glycine and the like; and the like can be illustrated.

As a group forming a prodrug used in a carboxy group, for example, lower alkyl such as methyl, ethyl, propyl, isopropyl, butyl, tert-butyl and the like; (lower alkyl)-COO-(lower alkylene) such as pivaloyloxymethyl, acetyloxymethyl, 1-(pivaloyloxy)ethyl, 1-(acetyloxy)ethyl and the like; (lower alkyl)-OCOO-(lower alkylene) such as ethyloxycarbonyloxymethyl, 1-(ethyloxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; cycloalkyl-OCOO-(lower alkylene) such as cyclohexyloxycarbonylmethyl, 1-(cyclohexyloxycarbonyl)ethyl and the like; and the like can be illustrated.

An (aza)indole derivative represented by the general formula (I) or a prodrug thereof, or a pharmaceutically acceptable salt thereof can be sometimes obtained as a hydrate or solvate thereof in the courses of purification or preparing salts thereof. An (aza)indole derivative represented by the general formula (I) of the present invention or a prodrug thereof, or a pharmaceutically acceptable salt thereof includes a hydrate thereof or a solvate thereof with a pharmaceutically acceptable solvent. As the pharmaceutically acceptable solvents, ethanol and the like can be illustrated.

A pharmaceutical composition of the present invention is useful as an agent for the prevention or treatment of diseases associated with high blood uric acid levels such as hyperuricemia, gouty tophus, gouty arthritis, renal disorder associated with hyperuricemia, urinary calculi or the like, especially for hyperuricemia.

When a pharmaceutical composition of the present invention are employed in the practical prevention or treatment, the dosage of a compound represented by the above general formula (I) or a prodrug thereof or a pharmaceutically acceptable salt thereof as the active ingredient is appropriately decided depending on the age, sex, body weight and degree of symptoms and treatment of each patient, for example, which is approximately within the range of from 1 to 2,000 mg per day per adult human in the case of oral administration, and the daily dose can be divided into one to several doses per day and administered.

When a pharmaceutical composition of the present invention are employed in the practical prevention or treatment, various dosage forms are orally or parenterally used depending on their uses, for example, formulations for oral administration such as powders, fine granules, granules, tablets, capsules, dry syrups or the like is preferable.

These pharmaceutical compositions can be prepared optionally by admixing using an appropriate pharmaceutical additive such as excipients, disintegrators, binders, lubricants and the like, and formulating the mixture in accordance with conventional methods.

For example, powders can be formulated by, if desired, admixing well an active ingredient with appropriate excipients, lubricants and the like. For example, tablets can be formulated by tableting an active ingredient with appropriate excipients, disintegrators, binders, lubricants and the like in accordance with conventional methods, further if desired, can be suitably coated to provide film-coated tablets, sugar-coated tablets, enteric-coated tablets and the like. For example, capsules can be formulated by admixing well an active ingredient with appropriate excipients, lubricants and the like, or formulating fine granules, granules in accordance with conventional methods, and filling it in appropriate capsules. Furthermore, in the case of such an oral administration drug, it can be also formulated by conducting quick-release or sustained-release formulation depending on the preventions or the treatment methods.

A compound represented by the above general formula (I) of the present invention, or a prodrug thereof or a pharmaceutically acceptable salt thereof can be used further in combination with any other drug for the treatment of hyperuricemia or drug for the treatment of gout. As the drug for the treatment of hyperuricemia which can be used in the present invention, for example, urinary alkalizers such as sodium hydrogen carbonate, potassium citrate and sodium citrate and the like can be illustrated. In addition, as the drug for the treatment of gout, colchicine, or non-steroidal anti-inflammatory drugs such as indomethacin, naproxen, fenbufen, pranoprofen, oxaprozin, ketoprofen, etoricoxib, tenoxicam and the like and steroids and the like can be illustrated. In the present invention, an active ingredient of the present invention can be also used further in combination with at least one of these drugs, and a pharmaceutical composition comprising combination with at least one of these drugs includes any dosage forms of not only a single preparation comprising together with the active ingredient of the present invention but also a combination formulation consisting of a pharmaceutical composition comprising the active ingredient of the present invention and a separately-prepared pharmaceutical composition for simultaneous administration or administration at different dosage intervals. Furthermore, when used in combination with any drug other than the active ingredient of the present invention, the dosage of the compound of the present invention can be reduced depending on the dosage of the other drug used in combination, as the case may be, an advantageous effect more than an additive effect in the prevention or treatment of the above diseases can be obtained, or an adverse effect of the other drug used in combination can be avoided or declined.

Effect of the Invention

The (aza)indole derivatives represented by the above general formula (I) of the present invention exert an excellent xanthine oxidase inhibitory activity and suppress the production of uric acid. In addition, a preferable compound of the present invention can also exert an excellent URAT1 inhibitory activity and enhance the uric acid excretion. Therefore, the (aza)indole derivatives represented by the general formula (I) of the present invention or a prodrugs thereof, or pharmaceutically acceptable salts thereof can extremely suppress increase in serum uric acid level and are useful as an agent for the prevention or treatment of diseases associated with abnormal serum uric acid level such as hyperiuricemia or the like.

BEST MODE TO OPERATE THE INVENTION

The present invention is further illustrated in more detail by way of the following Reference Examples, Examples and Test Examples. However, the present invention is not limited thereto.

Reference Example 1

4-Fluoro-2-hydroxy-benzoic acid ethyl ester

To a solution of 4-fluoro-2-hydroxybenzoic acid (3.0 g) in ethanol (40 mL) was added thionyl chloride (5.61 mL) at 0° C., and the mixture was heated under reflux for 24 hours. The reaction mixture was concentrated under reduced pressure. This residue was poured into water, and the resulting mixture was extracted with ethyl acetate. The organic layer was washed with water and brine, and dried over anhydrous magnesium sulfate. The solvent was removed under reduced pressure to give the title compound (3.5 g).

Reference Example 2

4-Fluoro-2-methoxymethoxybenzoic acid ethyl ester

To a solution of 4-fluoro-2-hydroxybenzoic acid ethyl ester (3.5 g) in dichloromethane (30 ml) were added N,N-diisopropylethylamine (5.0 g) and (chloromethyl)methyl ether (2.3 g) at 0° C., and this reaction mixture was stirred at room temperature overnight. This reaction mixture was poured into water, and the resulting mixture was extracted with ethyl acetate. The organic layer was washed with water and brine, and dried over anhydrous magnesium sulfate. The solvent was removed under reduced pressure. The residue was purified by column chromatography on silica gel (eluent: n-hexane/ethyl acetate) to give the title compound (2.8 g).

Reference Example 3

4-Fluoro-2-methoxymethoxybenzoic acid methyl ester

To a solution of 4-fluoro-2-hydroxybenzoic acid (3.0 g) in N,N-dimethylformamide (5 mL) were added sodium hydride (60% 1.0 g) and (chloromethyl)methyl ether (2.1 g) at room temperature, and this mixture was stirred for 48 hours at the same temperature. This reaction mixture was poured into 2 mol/L hydrochloric acid and the resulting mixture was extracted with ethyl acetate. The organic layer was washed with brine, and dried over anhydrous magnesium sulfate. The solvent was removed under reduced pressure. The residue was purified by column chromatography on silica gel (eluent: n-hexane/ethyl acetate) to give the title compound (0.22 g).

Reference Example 4

5,6-Difluoro-1H-indole-3-carbaldehyde

To a solution of 5,6-difluoro-1H-indole (1.0 g) in N,N-dimethylformamide (10 mL) was added phosphoryl chloride (1.2 g) at 0° C., and this mixture was stirred at room temperature for 4 hours. To this mixture was added 2 mol/L aqueous sodium hydroxide solution (5 mL), and this resulting mixture was stirred at 70° C. for 0.5 hours. After cooling to ambient temperature, this mixture was poured into 1 mol/L hydrochloric acid and the resulting mixture was extracted with ethyl acetate. The organic layer was washed with water and brine, and dried over anhydrous magnesium sulfate. The solvent was removed under reduced pressure to give the title compound (1.1 g).

Reference Example 5

5,6-Difluoro-1H-indole-3-carbonitrile

To a solution of 5,6-difluoro-1H-indole-3-carbaldehyde (1.0 g) in tetrahydrofuran (15 ml) were added hydroxylamine hydrochloride (0.81 g) and pyridine (1.9 g), and this mixture was stirred at 80° C. for 8 hours. Acetic anhydride was added to reaction mixture and this mixture was stirred at 80° C. for 8 hours. After cooling to ambient temperature, 2 mol/L aqueous sodium hydroxide solution was added to this mixture and resulting mixture was stirred for 30 minutes. This mixture was poured into 2 mol/L hydrochloric acid and the precipitated solid was collected by filtration, and washed with water and n-hexane. The solid was dissolved in ethyl acetate and this residue was purified by column chromatography on silica gel (eluent: n-hexane/ethyl acetate) to give the title compound (0.95 g).

Reference Example 6

6-Fluoro-1H-indole-3-carbonitrile

To a solution of 6-fluoro-1H-indole-3-carbaldehyde (0.97 g) in 90% formic acid (25 mL) were added hydroxylamine (0.65 g) and sodium formate (0.81 g), and this mixture was stirred at 100° C. for 3 hours. After cooling to ambient temperature, water was added to this reaction mixture and the precipitated solid was collected by filtration, and washed with water, dried to give the title compound (0.57 g).

Reference Example 7

5-Phenyl-1H-indole-carbonitrile

The title compound was prepared in a similar manner to that described in Reference Example 5 using the corresponding starting materials.

Reference Example 8

3-Formyl-1H-indole-5-carboxylic acid benzyl ester

To a solution of 1H-indole-5-carboxylic acid benzyl ester (3.5 g) in N,N-dimethylformamide (30 mL) was added phosphoryl chloride (2.6 g) under ice cooling and this mixture was stirred at room temperature for 2 hours. To this reaction mixture was added 2 mol/L aqueous sodium hydroxide solution until the pH became 6 and this mixture was stirred at 70° C. for 30 minutes. After cooling to ambient temperature, the precipitated solid was collected by filtration, and washed with water and methanol, dried to give the title compound (3.9 g).

Reference Compound 9

3-Cyano-1H-indole-5-carboxylic acid benzyl ester

To a solution of 3-formyl-1H-indole-5-carboxylic acid benzyl ester (4.3 g) and pyridine (4.8 g) in tetrahydrofuran (60 ml) was added hydroxylamine hydrochloride (1.6 g) at room temperature and this mixture was stirred at 80° C. overnight. Acetic anhydride was added to reaction mixture at the same temperature and this mixture was stirred for 8 hours. After cooling to ambient temperature, 1 mol/L sodium hydroxide solution (20 mL) was added to this mixture and resulting mixture was extracted with diethyl ether. The organic layer was washed with brine, and dried over anhydrous magnesium sulfate. The solvent was removed under reduced pressure and this residue was purified by column chromatography on silica gel (eluent: n-hexane/ethyl acetate) to give the title compound (2.8 g).

Reference Example 10

3-Benzyloxy-4-methylbenzoic acid benzyl ester

To a solution of 3-hydroxy-4-methylbenzoic acid (5.0 g) in N,N-dimethylformamide (100 mL) were added cesium carbonate (32 g) and benzyl bromide (12 g) at the same temperature and this mixture was stirred at room temperature for 2 days. To this reaction mixture was added a saturated aqueous sodium bicarbonate solution and this mixture was extracted with ethyl acetate. The organic layer was washed with brine, and dried over anhydrous magnesium sulfate. The solvent was removed under reduced pressure and this residue was purified by column chromatography on silica gel (eluent: n-hexane/ethyl acetate) to give the title compound (7.5 g).

Reference Example 11

(3-Benzyloxy-4-methylphenyl)methanol

To a suspension of lithium aluminum hydride in diethyl ether (50 mL) was added dropwise a solution of 3-Benzyloxy-4-methyl-benzoic acid benzyl ester (7.5 g) in diethyl ether (11 mL) under argon atmosphere at 0° C., and this mixture was stirred at room temperature for 6 hours. To this reaction mixture was added dropwise water (3.2 mL), and then Celite was added to this mixture and filtered. This filtrate was concentrated to give title compounds as a mixture of benzyl alcohol (7.0 g).

Reference Example 12

3-Benzyloxy-4-methylbenzaldehyde

To a solution of (3-benzyloxy-4-methylphenyl)methanol (1.0 g) in dichloromethane (50 mL) was added manganese dioxide (2.5 g), and this mixture was stirred at room temperature for 2 days. The insoluble material was removed by filtration and this filtrate was concentrated under reduced pressure. This residue was purified by column chromatography on silica gel (eluent: n-hexane/ethyl acetate) to give the title compound (0.39 g)

Reference Example 13

5-Benzyloxy-2-bromo-4-methylbenzaldehyde

To a solution of 3-benzyloxy-4-methylbenzaldehyde (0.39 g) in a mixed solvent of dichloromethane (1 mL) and methanol (1 mL) was added a solution of bromine (0.410 g) in dichloromethane (0.2 mL) at 0° C. and this mixture was stirred at room temperature for 2 hours. This mixture was poured into water and the resulting mixture was extracted with dichloromethane. The organic layer was washed with brine, and dried over anhydrous magnesium sulfate. The solvent was removed under reduced pressure. The residue was purified by column chromatography on silica gel (eluent: n-hexane/ethyl acetate) to give the title compound (0.39 g).

Reference Example 14

(Z)-3-(5-Benzyloxy-2-bromo-4-methylphenyl)-2-benzyloxycarbonylaminoacrylic acid methyl ester To a solution of 5-benzyloxy-2-bromo-4-methylbenzaldehyde (0.39 g) and N-(benzyloxycarbonyl)-alpha-phosphonoglycine trimethyl ester (0.38 g) in dichloromethane (2 mL) was added 1,1,3,3-tetramethylguanidine (0.18 g) at room temperature and this mixture was stirred at room temperature for 2 days. To this reaction mixture was added 1 mol/L hydrochloric acid and the precipitated solid was collected by filtration, and washed with water, dried under reduced pressure to give the title compound (0.34 g).

Reference Example 15

5-Benzyloxy-6-methyl-1H-indole-2-carboxylic acid methyl ester

To a solution of (Z)-3-(5-benzyloxy-2-bromo-4-methylphenyl)-2-benzyloxycarbonylaminoacrylic acid methyl ester (0.2 g) and copper (I) iodide (0.075 g) in dimethylsulfoxide (8 mL) was added cesium acetate (0.38 g) at room temperature and this mixture was stirred under argon atmosphere at 90° C. for 5 hours. To this reaction mixture was added aqueous ammonia solution (28%) and the precipitated solid was collected by filtration, and washed with water, dried under reduced pressure to give the title compound (0.073 g).

Reference Example 16

5-Benzyloxy-6-methyl-1H-indole-2-carboxylic acid

To a solution of 5-benzyloxy-6-methyl-1H-indole-2-carboxylic acid methyl ester (1.3 g) in a mixed solvent of 1,4-dioxane (40 mL) and water (20 mL) was added Lithium hydroxide mono hydrate (1.8 g) at room temperature and this mixture was stirred at 50° C. for 1 hour. After this reaction mixture was cooled to room temperature, 1 mol/L hydrochloric acid was added. This precipitated solid was collected by filtration, and washed with water, dried under reduced pressure to give the title compound (1.0 g).

Reference Example 17

5-Benzyloxy-6-methyl-1H-indole

To a solution of 5-benzyloxy-6-methyl-1H-indole-2-carboxylic acid (0.6 g) in quinoline (6 mL) was added copper powder (0.15 g), and this mixture was stirred at 220° C. for 20 minutes. This reaction mixture was poured into 1 mol/L hydrochloric acid, the resulting mixture was extracted with ethyl acetate. This organic layer was washed with brine, and dried over anhydrous magnesium sulfate. The solvent was removed under reduced pressure. The residue was purified by column chromatography on silica gel (eluent: n-hexane/ethyl acetate) to give the title compound (0.21 g).

Reference Example 18

5-Benzyloxy-6-methyl-1H-indole-3-carbaldehyde

The title compound (0.48 g) was prepared in a similar manner to that described in Reference Example 4 using the corresponding starting materials.

Reference Example 19

5-Benzyloxy-6-methyl-1H-indole-3-carbonitrile

The title compound (0.10 g) was prepared in a similar manner to that described in Reference Example 5 using the corresponding starting materials.

Reference Example 20

4-(6-Nitroindol-1-yl)benzoic acid ethyl ester

To a solution of 6-nitro-1H-indole (0.5 g) in N,N-dimethylformamide (10 mL) were added cesium carbonate (1.2 g) and 4-fluoro benzoic acid ethyl ester (0.62 g), and this mixture was stirred at 75° C. overnight. This reaction mixture was poured into water and the precipitated solid was collected by filtration, and washed with water and n-hexane, dried under reduced pressure to give the title compound (0.64 g).

Reference Example 21

1-(5-Formylfuran-2-yl)-1H-indole-3-carbonitrile

A suspension of 3-cyanoindole (0.14 g), 5-bromo-2-furaldehyde (0.18 g), and cesium carbonate (0.39 g) in N,N-dimethylformamide (3 mL) was stirred at room temperature or 3 hours. This reaction mixture was heated at 50° C., stirred for 2 hours. After cooling to ambient, water was added to this reaction mixture. This mixture was extracted with ethyl acetate, and this organic layer was washed with brine, and dried over anhydrous magnesium sulfate. The solvent was removed under reduced pressure. The residue was purified by column chromatography on silica gel (eluent: n-hexane/ethyl acetate-2/1) to give the title compound (0.086 g).

Reference Example 22

4-(6-Formylindol-1-yl)benzoic acid ethyl ester

The title compound was prepared in a similar manner to that described in Reference Example 20 using the corresponding starting materials.

Reference Example 23

4-(6-Acetoxymethyl-indol-1-yl)benzoic acid ethyl ester

To a solution of 4-(6-formylindol-1-yl)benzoic acid ethyl ester in a mixed solvent of tetrahydrofuran (3 mL) and methanol (10 mL) was added sodium borohydride (0.075 g) at 0° C., and this mixture was stirred at room temperature for 0.5 hours. This reaction mixture was poured into a saturated aqueous ammonium chloride solution and this mixture was extracted with ethyl acetate. This organic layer was washed with brine, and dried over anhydrous magnesium sulfate. The solvent was removed under reduced pressure to give 4-(6-hydroxymethyl-indol-1-yl)benzoic acid ethyl ester (0.38 g). To a solution of 4-(6-hydroxymethyl-indol-1-yl)benzoic acid ethyl ester (0.09 g) in dichloromethane (1 mL) were added acetic anhydride (0.093 g) and pyridine (0.024 g), and this mixture was stirred at room temperature for 2 days. This mixture was poured into water and the resulting mixture was extracted with ethyl acetate. This organic layer was washed with brine, and dried over anhydrous magnesium sulfate. The solvent was removed under reduced pressure. The residue was purified by column chromatography on silica gel (eluent: n-hexane/ethyl acetate) to give the title compound (0.068 g).

Reference Example 24

Methyl 4-fluoro-2-methyl carbonate

To a solution of 4-fluoro-2-methylphenol (2.0 g) in 1,4-dioxane (20 mL) were added methyl chloroformate (3.0 g) and pyridine (2.5 g) at under ice cooling and this mixture was stirred at room temperature overnight. The insoluble material was removed by filtration and 1 mol/L hydrochloric acid was added to this filtrate. This mixture was extracted with ethyl acetate and the organic layer was washed with water twice, and dried over anhydrous magnesium sulfate. The solvent was removed under reduced pressure to give the title compound.

Reference Example 25

4-Fluoro-2-methyl-5-nitrophenol

To a solution of methyl 4-fluoro-2-methyl carbonate (2.9 g) in concentrated sulfuric acid (11 mL) was added fuming nitric acid (1.1 mL) in a dropwise manner over 10 min under ice cooling, and this mixture was stirred at the same temperature for 1 hour. This reaction mixture was poured into ice water and this mixture was extracted with ethyl acetate. This organic layer was washed with water twice, and dried over anhydrous magnesium sulfate. The solvent was removed under reduced pressure. This residue was dissolved in methanol, to this solution was added sodium bicarbonate (2.6 g) and potassium carbonate (2.2 g) at room temperature and this mixture was stirred for 2 hours. To the reaction mixture was added 1 mol/L hydrochloric acid until the pH became 1 and this organic solvent was removed under reduced pressure. This residue was extracted with ethyl acetate and the organic layer was washed with water and brine, dried over anhydrous magnesium sulfate. The solvent was removed under reduced pressure. The residue was purified by column chromatography on silica gel (eluent: n-hexane/ethyl acetate) to give the title compound (1.5 g).

Reference Example 26

1-Fluoro-4-methoxy-5-methyl-2-nitrobenzene

To a solution of 4-fluoro-2-methyl-5-nitrophenol (0.5 g) in N,N-dimethylformamide (5 mL) were added potassium carbonate (0.44 g) and iodomethane (0.46 g), and this mixture was stirred at room temperature overnight. To this reaction mixture was added water and the precipitated solid was collected by filtration, and washed with water and n-hexane to give the title compound (0.44 g).

Reference Example 27

Cyano-(4-methoxy-5-methyl-2-nitrophenyl)acetic acid methyl ester

To a suspension of sodium hydride (0.86 g) in N,N-dimethylformamide (5 mL) was added dropwise a solution of cyano acetic acid methyl ester (0.35 g) in N,N-dimethylformamide (3 mL) under ice cooling and this mixture was stirred for 15 minutes. To this reaction mixture was added dropwise a solution of 1-fluoro-4-methoxy-5-methyl-2-nitrobenzene (0.44 g) under ice cooling and this mixture was stirred at room temperature for 30 minutes, and then stirred at 70° C. overnight. After cooling to ambient temperature, 1 mol/L hydrochloric acid (5 mL) was added to this reaction mixture. This resulting mixture was extracted with ethyl acetate. This organic layer was washed with water and brine, and dried over anhydrous magnesium sulfate. The solvent was removed under reduced pressure. The residue was purified by column chromatography on silica gel (eluent: n-hexane/ethyl acetate) to give the title compound (0.45 g).

Reference Example 28

(4-Methoxy-5-methyl-2-nitrophenyl)acetonitrile

To a solution of cyano-(4-methoxy-5-methyl-2-nitrophenyl)acetic acid methyl ester in methanol (1.7 mL) was added 6 mol/L hydrochloric acid (1.7 mL), and this mixture was heated under reflux for 9 hours. After cooling to ambient temperature, this organic solvent was removed under reduced pressure and resulting mixture was extracted with ethyl acetate. The residue was purified by column chromatography on silica gel (eluent: n-hexane/ethyl acetate) to give the title compound (0.25 g).

Reference Example 29

6-Methoxy-5-methylindole

To a solution of (4-methoxy-5-methyl-2-nitrophenyl)acetonitrile (0.24 g) in a mixed solvent of tetrahydrofuran (2 mL) and n-butanol (2 mL) was added palladium-carbon powder (0.043 g) under an argon atmosphere and this mixture was stirred at 60° C. under a hydrogen atmosphere for 36 hours. The insoluble material was removed by filtration and the filtrate was concentrated under reduced pressure. The residue was purified by column chromatography on silica gel (eluent: n-hexane/ethyl acetate) to give the title compound (0.13 g).

Reference Example 30

3-Cyano-6-methoxy-5-methylindole

The title compound (0.070 g) was prepared in a similar manner to that described in Reference Example 4 and Reference Example 5 using the corresponding starting materials.

Reference Example 31

1-Methoxy-2-methyl-4-nitrobenzene

To a solution of 1-hydroxy-2-methyl-4-nitrobenzene (1.0 g) in N,N-dimethylformamide (10 mL) were added potassium carbonate (1.8 g) and iodomethane (1.3 g) at room temperature and this mixture was stirred at the same temperature for 24 hours. This reaction mixture was poured into water and this resulting mixture was extracted with ethyl acetate. This organic layer was washed with water and brine, and dried over anhydrous magnesium sulfate. The solvent was removed under reduced pressure to give the title compound (0.95 g).

Reference Example 32

(5-Methoxy-4-methyl-2-nitrophenyl)acetonitrile

To a solution of 1-methoxy-2-methyl-4-nitrobenzene (0.4 g) and (4-chlorophenoxy)acetonitrile (0.4 g) in N,N-dimethylformamide (10 mL) was added potassium tert-butoxide (0.3 g) under ice cooling and this mixture was stirred at the same temperature for 1 hours. This mixture was poured into water and the resulting mixture was extracted with ethyl acetate. This organic layer was washed with water and brine, and dried over anhydrous magnesium sulfate. The solvent was removed under reduced pressure. The residue was purified by column chromatography on silica gel (eluent: n-hexane/ethyl acetate) to give the title compound (0.2 g).

Reference Example 33

5-Methoxy-6-methyl-1H-indole

The title compound (0.065 g) was prepared in a similar manner to that described in Reference Example 29 using the corresponding starting materials.

Reference Example 34

5-Methoxy-6-methyl-1H-indole-3-carbonitrile

The title compound (0.05 g) was prepared in a similar manner to that described in Reference Example 4 and 5 using the corresponding starting materials.

Reference Example 35

5-Benzyloxy-6-chloro-1H-indole

To a solution of (5-benzyloxy-4-chloro-2-nitrophenyl)acetonitrile (4.170 g) in ethanol (70 mL) was added platinum (IV) oxide (0.344 g) at room temperature and this mixture was stirred under a hydrogen atmosphere (30-35 psi) for 12 hours. To this reaction mixture were added acetic acid (7 mL) and water (7 mL), and this mixture was stirred under same condition for 24 hours. After this reaction mixture was replaced under argon atmosphere, the insoluble material was removed by filtration. To this filtrate was added water and this resulting mixture was extracted with diethyl ether. This organic layer was washed with brine, and dried over anhydrous magnesium sulfate, and filtered. The solvent was removed under reduced pressure. The residue was purified by column chromatography on silica gel (eluent: ethyl acetate/n-hexane=75/25) to give the title compound (0.629 g).

Reference Example 36

5-Benzyloxy-6-chloro-1H-indole-3-carbaldehyde

The title compound (0.270 g) was prepared in a similar manner to that described in Reference Example 4 using the corresponding starting materials.

Reference Example 37

5-Benzyloxy-6-chloro-1H-indole-3-carbonitrile

The title compound (0.267 g) was prepared in a similar manner to that described in Reference Example 5 using the corresponding starting materials.

Reference Example 38

Cyano-(4-fluoro-5-methyl-2-nitrophenyl)acetic acid benzyl ester

A suspension of 1,4-difluoro-2-methyl-5-nitrobenzene (1.00 g), cyanoacetic acid benzyl ester (1.01 g) and potassium carbonate (1.76 g) in N,N-dimethylformamide (20.0 mL) was stirred at 60° C. for 1 day. To this reaction mixture was added 1 mol/L hydrochloric acid (25.4 mL), and this mixture was extracted with diethyl ether. This organic layer was washed with brine, and dried over anhydrous magnesium sulfate, and filtered. The solvent was removed under reduced pressure. This residue was washed with ethanol to give the title compound (1.54 g).

Reference Example 39

6-Fluoro-5-methyl-1H-indole

To a solution of cyano-(4-fluoro-5-methyl-2-nitrophenyl) acetic acid benzyl ester (1.54 g), acetic acid (7 mL) and water (7 mL) in ethanol (15 mL) was added 10% palladium-carbon (0.154 g) under an argon atmosphere. This reaction mixture was stirred at room temperature for 60 hours under a hydrogen atmosphere. After water was added to this reaction mixture, hydrogen was exchanged by argon. The insoluble material was removed by filtration, and this filtrate was extracted with diethyl ether. This organic layer was washed with brine, and dried over anhydrous magnesium sulfate, and filtered. The solvent was removed under reduced pressure. The residue was purified by column chromatography on silica gel (eluent: ethyl acetate/n-hexane=75/25) to give the title compound (0.536 g).

Reference Example 40

6-Fluoro-5-methyl-1H-indole-3-carbaldehyde

The title compound (0.577 g) was prepared in a similar manner to that described in Reference Example 4 using the corresponding starting materials.

Reference Example 41

6-Fluoro-5-methyl-1H-indole-3-carbonitrile

The title compound (0.544 g) was prepared in a similar manner to that described in Reference Example 5 using the corresponding starting materials.

Reference Example 42

6-Benzyloxy-5-methoxy-1H-indole

4-Benzyloxy-3-methoxybenzaldehyde (4.85 g) was added to nitric acid (d=1.42, 20 mL) in a dropwise manner over 1 hour at room temperature, and this mixture was stirred for 1 hour. This reaction mixture was poured into ice water and the precipitated solid was collected by filtration. This solid was washed with water, dried under reduced pressure at 50° C. to give 4-benzyloxy-5-methoxy-2-nitrobenzaldehyde (4.99 g). To this product was added acetic acid (50 mL), followed by adding nitromethane (3.19 g) and ammonium acetate (5.36 g), and this mixture was stirred for 5 hours at 100° C. This reaction mixture was concentrated under reduced pressure. To this residue was added water and the precipitated solid was collected by filtration, and this solid was washed with methanol, dried to give 1-benzyloxy-2-methoxy-5-nitro-4-(2-nitrovinyl)benzene (4.03 g). To this compound were added benzene (96 mL), acetic acid (72 mL) and cyclohexane (24 mL), followed by adding silica gel (18 g) and iron powder (10.2 g), and this mixture was stirred at 100° C. for 1 hour. The insoluble material was removed by filtration, and this filtrate was concentrated under reduced pressure. The residue was purified by column chromatography on silica gel (eluent: ethyl acetate/n-hexane=75/25) to give the title compound (1.06 g).

Reference Example 43

6-Benzyloxy-5-methoxy-1H-indole-3-carbaldehyde

The title compound was prepared in a similar manner to that described in Reference Example 4 using the corresponding starting materials.

Reference Example 44

6-Benzyloxy-5-methoxy-1H-indole-3-carbonitrile

The title compound was prepared in a similar manner to that described in Reference Example 5 using the corresponding starting materials.

Reference Examples 45 to 47

The title compounds were prepared in a similar manner to that described in Reference Example 29 using the corresponding starting materials.

Reference Example 48

Dimethyl-(4-nitro-2-trifluoromethylphenyl)amine

To a solution of 1-floro-4-nitro-2-trifluoromethylbenzene (2.0 g) in tetrahydrofuran (20 mL) were added dimethyamine (0.64 g) and sodium hydride (0.34 g) at room temperature, and this mixture was stirred at 50° C. for 16 hours. This reaction mixture was poured into water, and this mixture was extracted with ethyl acetate. This organic layer was washed with water and brine, and dried over anhydrous magnesium sulfate. The solvent was removed under reduced pressure. The residue was purified by column chromatography on silica gel (eluent: n-hexane/ethyl acetate) to give the title compound (0.94 g).

Reference Example 49

(5-Dimethylamino-2-nitro-4-trifluoromethylphenyl)acetonitrile

To a solution of dimethyl-(4-nitro-2-trifluoromethylphenyl)amine (0.95 g) in N,N-dimethylformamide (20 mL) were added (4-chlorophenoxy)acetonitrile (0.75 g) and 1 mol/L potassium tert-butoxide (4.5 mL, in tetrahydrofuran solution) under ice cooling, and this mixture was stirred at the same temperature for 1 hour. This reaction mixture was poured into water, and this mixture was extracted with ethyl acetate. This organic layer was washed with water and brine, and dried over anhydrous magnesium sulfate. The solvent was removed under reduced pressure. The residue was purified by column chromatography on silica gel (eluent: n-hexane/ethyl acetate) to give the title compound (0.11 g).

Reference Example 50

Dimethyl-(6-trifluoromethyl-1H-indol-5-yl)amine

To a solution of (5-dimethylamino-2-nitro-4-trifluoromethylphenyl)acetonitrile (0.058 g) in a mixed solvent of ethanol (1 mL), acetic acid (0.1 mL) and water (0.1 mL) was added palladium-carbon powder (0.0058 g), and this mixture was stirred at 35° C. for 16 hours. The insoluble material was removed by filtration and the filtrate was concentrated under reduced pressure to give the title compound (0.058 g).

Reference Example 51

4-(5-Dimethylamino-6-trifluoromethylindol-1-yl)benzoic acid ethyl ester

The title compound was prepared in a similar manner to that described in Reference Example 20 using the corresponding starting materials.

Reference Example 52

4-(3-Formyl-5-methylamino-6-trifluoromethylindol-1-yl)benzoic acid ethyl ester

To a solution of 4-(5-dimethylamino-6-trifluoromethylindol-1-yl)benzoic acid ethyl ester (0.054 g) in N,N-dimethylformamide (2 mL) was added phosphoryl chloride (0.026 g) under ice cooling, and this mixture was stirred at room temperature for 16 hours. To this mixture was added 2 mol/L aqueous sodium hydroxide solution (5 mL), and this resulting mixture was stirred at 50° C. for 30 minutes. After cooling to ambient temperature, 1 mol/L hydrochloric acid (10 mL) was added to this mixture, and the precipitated solid was collected by filtration. This solid was washed with water and n-hexane, dried under reduced pressure at 50° C. to give the title compound (0.026 g).

Reference Example 53

The title compound was prepared in a similar manner to that described in Reference Example 29 using (3-benzyloxy-2,4-dimethyl-6-nitrophenyl)acetonitrile instead of (4-methoxy-5-methyl-2-nitrophenyl)acetonitrile.

Reference Examples 54 to 55

The title compounds were prepared in a similar manner to that described in Example 5 using the indole obtained in a similar manner to that described in Reference example 31 using Reference example 53 and the corresponding starting materials.

Reference Examples 56 to 63

The title compounds were prepared in a similar manner to that described in Reference Example 5 using the corresponding starting materials.

Example 1

4-(3-Cyano-5,6-difluoroindol-1-yl)-2-methoxymethoxybenzoic acid ethyl ester

To a solution of 3-cyano-5,6-difluoroindole (0.25 g) in N,N-dimethylformamide (10 mL) were added cesium carbonate (0.91 g), 4-fluoro-2-methoxymethoxybenzoic acid ethyl ester (0.32 g), and this mixture was stirred at 75° C. overnight. This reaction mixture was poured into water, and this resulting mixture was extracted with ethyl acetate. This organic layer was washed with water and brine, and dried over anhydrous magnesium sulfate. The solvent was removed under reduced pressure. The residue was purified by column chromatography on silica gel (eluent: ethyl acetate/n-hexane=10/90-75/25) to give the title compound (0.12 g).

Example 2

4-(3-Cyano-5,6-difluoroindol-1-yl)-2-hydroxybenzoic acid ethyl ester

To a solution of 4-(3-cyano-5,6-difluoroindol-1-yl)-2-methoxymethoxybenzoic acid ethyl ester (0.12 g) in a mixed solvent of tetrahydrofuran (1.5 mL) and ethanol (3 mL) was added 2 mol/L hydrochloric acid (1.0 mL), and this mixture was stirred at 70° C. overnight. After cooling to ambient temperature, the precipitated solid was collected by filtration, and washed with water and n-hexane, and dried under reduced pressure at 40° C. to give the title compound (0.074 g).

Example 3

4-(3-Cyano-5,6-difluoroindol-1-yl)-2-hydroxybenzoic acid

To a solution of 4-(3-cyano-5,6-difluoroindol-1-yl)-2-hydroxybenzoic acid ethyl ester (0.074 g) in a mixed solvent of tetrahydrofuran (3.0 mL) and ethanol (0.75 mL) were added 0.1 g/mL aqueous lithium hydroxide solution (0.62 mL) and water (1.0 mL), and this mixture was stirred at room temperature for 26 hours. To this reaction mixture was added 2 mol/L hydrochloric acid (5 mL), this organic solvent was removed under reduced pressure. This resulting mixture was extracted with ethyl acetate, this organic layer was washed with water, and dried over anhydrous magnesium sulfate. The solvent was concentrated under reduced pressure to give the title compounds (0.06 g).

Example 4

4-(6-Benzyloxy-3-cyanoindol-1-yl)-2-methoxymethoxybenzoic acid ethyl ester

The title compound (3.4 g) was prepared in a similar manner to that described in Example 1 using the corresponding starting materials.

Example 5

4-(6-Benzyloxy-3-cyanoindol-1-yl)-2-hydroxybenzoic acid

The title compound was prepared in a similar manner to that described in Example 2 and Example 3 using the corresponding starting materials.

Example 6

4-(3-Cyano-6-hydroxyindol-1-yl)-2-methoxymethoxybenzoic acid ethyl ester

To a solution of 4-(6-benzyloxy-3-cyanoindol-1-yl)-2-methoxymethoxybenzoic acid ethyl ester in a mixed solvent of ethyl acetate (60 mL) and methanol (60 mL) was added palladium-carbon powder (0.61 g) under argon atmosphere at 0° C. and this mixture was stirred at 40° C. under a hydrogen atmosphere for 3 hours. The insoluble material was removed by filtration, and the filtrate was concentrated under reduced pressure to give the title compound (2.5 g)

Example 7

4-[6-(2-Benzyloxycarbonylaminoethyloxy)-3-cyanoindol-1-yl]-2-methoxymethoxybenzoic acid ethyl ester To a solution of 4-(3-cyano-6-hydroxyindol-1-yl)-2-methoxymethoxybenzoic acid ethyl ester (0.37 g) in N,N-dimethylformamide (10 mL) were added (2-bromoethyl)carbamic acid benzyl ester (0.39 g) and potassium carbonate (0.28 g), and this mixture was stirred at 50° C. overnight. This reaction mixture was poured into water, and the precipitated solid was collected by filtration. This solid was washed with methanol, and dried to give the title compound (0.40 g).

Example 8

4-[6-(2-Benzyloxycarbonylaminoethyloxy)-3-cyanoindol-1-yl]-2-hydroxybenzoic acid To a solution of 4-[6-(2-benzyloxycarbonylaminoethyloxy)-3-cyanoindol-1-yl]-2-methoxymethoxybenzoic acid ethyl ester (0.14 g) in a mixed solvent of ethanol (2.5 mL), tetrahydrofuran (5 mL), and water (2.5 mL) was added lithium hydroxide mono hydrate (0.03 g), and this mixture was stirred at room temperature for 3 hours. To this reaction mixture was added 2 mol/L hydrochloric acid (0.75 mL), and this mixture was stirred at 50° C. for 5 hours. This reaction mixture was treated 1 mol/L hydrochloric acid (5 mL), and this mixture was concentrated under reduced pressure until this solvent volume became one-third. The precipitated solid was collected by filtration, and washed with water, methanol and ether to give the title compound (0.097 g)

Example 9

4-[6-(2-Aminoethyloxy)-3-cyanoindol-1-yl]-2-hydroxybenzoic acid

To a solution of 4-[6-(2-benzyloxycarbonylaminoethyloxy)-3-cyanoindol-1-yl]-2-hydroxybenzoic acid (0.087 g) in a mixed solvent ethyl acetate (2 mL) and methanol (2 mL) was added palladium-carbon powder (0.016 g) under an argon atmosphere at 0° C., and this mixture was stirred at 40° C. under a hydrogen atmosphere for 3 hours. The insoluble material was removed by filtration, and the filtrate was concentrated under reduced pressure. This obtained light yellow solid was washed with diethyl ether, dried to give the title compound (0.058 g).

Example 10

4-[6-(2-Aminoethyloxy)-3-cyanoindol-1-yl]-2-methoxymethoxybenzoic acid ethyl ester To a solution of 4-[6-(2-benzyloxycarbonylaminoethoylxy)-3-cyanoindol-1-yl]-2-methoxymethoxybenzoic acid ethyl ester (0.27 g) in a mixed solvent of ethyl acetate (5 mL) and methanol (5 mL) was added palladium-carbon powder (0.05 g) under an argon atmosphere at 0° C., and this mixture was stirred at 40° C. under a hydrogen atmosphere for 3 hours. The insoluble material was removed by filtration, and the filtrate was concentrated under reduced pressure. This obtained light yellow solid was washed with diethyl ether, dried to give the title compound (0.20 g).

Example 11

4-[6-(2-Acetylaminoethyloxy)-3-cyanoindol-1-yl]-2-methoxymethoxybenzoic acid ethyl ester To a solution of 4-[6-(2-aminoethyloxy)-3-cyanoindol-1-yl]-2-methoxymethoxybenzoic acid ethyl ester (0.10 g) and triethylamine (0.076 g) in dichloromethane (5 mL) was added acetyl chloride (0.049 g) at room temperature, and this mixture was stirred at room temperature for 12 hours. This reaction mixture was concentrated under reduced pressure. The residue was purified by column chromatography on silica gel (eluent: dichloromethane:methanol=10:1) to give the title compound (0.083 g).

Example 12

4-[6-(2-Acetylaminoethyloxy)-3-cyanoindol-1-yl]-2-hydroxybenzoic acid

The title compound (0.039 g) was prepared in a similar manner to that described in Example 8 using the corresponding starting materials.

Example 13

4-(5-Bromo-3-cyanoindol-1-yl)benzoic acid ethyl ester

To a solution of 5-bromo-3-cyanoindole (2.0 g) in N,N-dimethylformamide (50 mL) were added cesium carbonate (7.4 g) and 4-fluorobenzoic acid ethyl ester (3.0 g), and this mixture was stirred at 80° C. for 48 hours. This reaction mixture was poured into water, and the precipitated solid was collected by filtration. This solid was washed with water, dried under reduced pressure at 50° C. to give the title compound (1.8 g).

Example 14

4-[3-Cyano-5-(4-methoxyphenyl)indol-1-yl]benzoic acid ethyl ester

A mixture of 4-(5-bromo-3-cyanoindol-1-yl)benzoic acid ethyl ester (0.1 g), 4-methoxyphenylboronic acid (0.066 g), potassium carbonate (0.09 g) in a mixed solvent of 1,2-dimethoxyethane (3 mL), ethanol (0.5 mL) and water (0.5 mL) was stirred in the presence of tetrakis(triphenylphosphine) palladium catalyst at 90° C. for 18 hours. This reaction mixture was poured into water, and the precipitated solid was collected by filtration. This solid was washed with water, dried under reduced pressure at 50° C. to give the title compound (0.098 g).

Example 15

4-[3-Cyano-5-(4-methoxyphenyl)indol-1-yl]benzoic acid

The title compound (0.081 g) was prepared in a similar manner to that described in Example 3 using the corresponding starting materials.

Example 16

4-{5-[(E)-2-Ethoxycarbonylvinyl]-3-cyanoindol-1-yl}benzoic acid

A solution of 4-(5-bromo-3-cyanoindol-1-yl)benzoic acid ethyl ester (0.1 g), acrylic acid ethyl ester (0.11 g) and triethylamine (0.082 g) in N,N-dimethylformamide (2 mL) was stirred in the presence of palladium (II) acetate (0.0061 g) and triphenylphosphine (0.014 g) at 100° C. for 30 hours. This reaction mixture was poured into water, and this resulting mixture was extracted with ethyl acetate twice. This organic layer was washed with brine, and dried over anhydrous magnesium sulfate. The solvent was concentrated under reduced pressure. The residue was purified by column chromatography on silica gel. (eluent: ethyl acetate/n-hexane=10/90-75/25) to give the title compound (0.035 g).

Example 17

4-[5-((E)-2-Carboxyvinyl)-3-cyanoindol-1-yl]benzoic acid

The title compound was prepared in a similar manner to that described in Example 3 using the corresponding starting materials.

Example 18

4-(4-Benzyloxy-3-cyanoindol-1-yl)benzoic acid ethyl ester

The title compound (0.16 g) was prepared in a similar manner to that described in Example 13 using the corresponding starting materials.

Example 19

4-(4-Benzyloxy-3-cyanoindol-1-yl)benzoic acid

To a solution of 4-(4-benzyloxy-3-cyanoindol-1-yl)benzoic acid ethyl ester (0.16 g) in ethanol (2 mL) was added 2 mol/L aqueous sodium hydroxide solution (0.4 mL), and this mixture was stirred at 50° C. overnight. Ethanol was removed under reduced pressure, and to this reaction mixture was added 2 mol/L hydrochloric acid (3 mL). The precipitated solid was collected by filtration, and this solid was washed with water and n-hexane to give the title compound (0.11 g).

Example 20

4-(3-Cyano-6-nitroindol-1-yl)benzoic acid ethyl ester

To a solution of 4-(6-nitroindol-1-yl)benzoic acid ethyl ester (0.53 g) in N,N-dimethylformamide (6 mL) was added phosphoryl chloride (0.31 g) under ice cooling and this mixture was stirred at 70° C. overnight. After cooling to ambient temperature, to this reaction mixture was added 2 mol/L aqueous sodium hydroxide solution and this mixture was stirred at 30 minutes. This reaction mixture was poured into 1 mol/L hydrochloric acid, and the precipitated solid was collected by filtration, and washed with water and n-hexane, and dried under reduced pressure at 40° C. to give 4-(3-formyl-6-nitroindol-1-yl)benzoic acid ethyl ester (0.46 g). To a solution of this aldehyde (0.46 g) in tetrahydrofuran (10 mL) were added hydroxylamine hydrochloride (0.19 g) and pyridine (0.43 g) at room temperature, and this mixture was stirred at 80° C. for 8 hours. To this reaction mixture was added acetic anhydride (0.42 g) at 80° C., this mixture was stirred at same temperature overnight. After cooling to ambient temperature, to this reaction mixture was added 1 mol/L hydrochloric acid, and the precipitated solid was collected by filtration. This solid was washed with water, n-hexane and diethyl ether to give the title compound (0.13 g).

Example 21

4-(6-Amino-3-cyanoindol-1-yl)benzoic acid ethyl ester

To a solution of 4-(3-cyano-6-nitroindol-1-yl)benzoic acid ethyl ester (0.11 g) in a mixed solvent of tetrahydrofuran (2 mL) and methanol (2 mL) was added palladium-carbon powder (0.04 g) under an argon atmosphere, and this mixture was stirred at room temperature under a hydrogen atmosphere for 7 hours. The insoluble material was removed by filtration, and the filtrate was concentrated under reduced pressure to give the title compound (0.070 g).

Example 22

4-(3-Cyano-6-methanesulfonylaminoindol-1-yl)benzoic acid ethyl ester

To a solution of 4-(5-amino-3-cyanoindol-1-yl)benzoic acid ethyl ester (0.070 g) in dichloromethane (2 mL) were added methanesulfonyl chloride (0.035 g) and pyridine (0.036 g) at room temperature, and this mixture was stirred at room temperature overnight. This reaction mixture was poured into 1 mol/L hydrochloric acid, this resulting mixture was extracted with ethyl acetate. This organic layer was washed with water, and dried over anhydrous magnesium sulfate. The solvent was removed under reduced pressure. The residue was purified by column chromatography on silica gel (eluent: ethyl acetate/n-hexane=10/90-75/25) to give the title compound (0.046 g).

Example 23

4-(3-Cyano-6-methanesulfonylaminoindol-1-yl)benzoic acid

The title compound (0.040 g) was prepared in a similar manner to that described in Example 3 using the corresponding starting materials.

Example 24

4-(5-Benzyloxy-3-cyanoindol-1-yl)benzoic acid ethyl ester

The title compound was prepared in a similar manner to that described in Example 13 using the corresponding starting materials.

Example 25

4-(5-Hydroxy-3-cyanoindol-1-yl)benzoic acid ethyl ester

The title compound was prepared in a similar manner to that described in Example 6 using the corresponding starting materials.

Example 26

4-[3-Cyano-5-(thiophen-2-ylmethyloxy)indol-1-yl]benzoic acid ethyl ester

To a solution of 4-(5-hydroxy-3-cyanoindol-1-yl)benzoic acid ethyl ester and thiophene-2-methanol (0.057 g) and triphenylphosphine (0.012 g) in tetrahydrofuran (2.5 mL) was added diisopropylcarbodiimide (40% toluene solution, 0.18 mL) at room temperature, and this mixture was stirred for 3 hours. This reaction mixture was concentrated under reduced pressure. This residue was purified by column chromatography on silica gel (eluent: ethyl acetate/n-hexane=1/3) to give the title compound (0.10 g).

Example 27

4-[3-Cyano-5-(thiophen-2-ylmethyloxy)indol-1-yl]benzoic acid

The title compound (0.01 g) was prepared in a similar manner to that described in Example 3 using the corresponding starting materials.

Example 28

4-(3-Cyano-5-benzyloxycarbonylindol-1-yl)benzoic acid ethyl ester

The title compound (0.24 g) was prepared in a similar manner to that described in Example 13 using the corresponding starting materials.

Example 29

4-(5-Carboxy-3-cyanoindol-1-yl)benzoic acid

The title compound (0.050 g) was prepared in a similar manner to that described in Example 3 using the corresponding starting materials.

Example 30

4-(5-Carboxy-3-cyanoindol-1-yl)benzoic acid ethyl ester

To a solution of 4-(3-cyano-5-benzyloxycarbonylindol-1-yl)benzoic acid ethyl ester (0.16 g) in a mixed solvent of methanol (5 mL) and tetrahydrofuran (5 mL) was added palladium-carbon powder (0.03 g) at 0° C. under an argon atmosphere, and this mixture was stirred at room temperature under a hydrogen atmosphere for 3 hours. The insoluble material was removed by filtration, and the filtrate was concentrated under reduced pressure to give the title compound (0.057 g).

Example 31

4-(3-Cyano-5-hydroxymethylindole-1-yl)benzoic acid ethyl ester

To a solution of 4-(5-carboxy-3-cyanoindol-1-yl)benzoic acid ethyl ester (0.057 g) in tetrahydrofuran (2 mL) was added borane-tetrahydrofuran complex (1.2 mol/L tetrahydrofuran solution 0.2 mL) at 0° C. and this mixture was stirred at room temperature for 2 hours. To this reaction mixture was added a saturated aqueous sodium bicarbonate solution, this mixture was extracted with diethyl ether. This organic layer was washed with brine, and dried over anhydrous magnesium sulfate. The solvent was removed under reduced pressure. The residue was purified by column chromatography on silica gel (eluent: ethyl acetate/n-hexane=1/1) to give the title compound (0.032 g).

Example 32

4-(3-Cyano-5-hydroxymethylindol-1-yl)benzoic acid

The title compound (0.029 g) was prepared in a similar manner to that described in Example 3 using the corresponding starting materials.

Example 33

4-(3-Cyano-5-dimethylaminocarbonylindol-1-yl) benzoic acid ethyl ester

To a solution of 4-(5-carboxy-3-cyanoindol-1-yl)benzoic acid ethyl ester (0.084 g), dimethylamine hydrochloride (0.061 g), triethylamine (0.13 g) and 4-dimethylaminopyridine (0.006 g) in dichloromethane (2.5 mL) was added N-ethyl-N'-3-dimethylaminopropylcarbodiimide (0.058 g) at room temperature, and this mixture was stirred at room temperature overnight. This reaction mixture was poured into 1 mol/L hydrochloric acid, and this mixture was extracted with ethyl acetate. This organic layer was washed with a saturated aqueous sodium bicarbonate solution and brine, dried over anhydrous magnesium sulfate. The solvent was removed under reduced pressure. The residue was purified by column chromatography on silica gel (eluent: ethyl acetate/n-hexane=1/2) to give the title compound (0.020 g).

Example 34

4-(3-Cyano-5-dimethylaminocarbonylindol-1-yl) benzoic acid

The title compound (0.0025 g) was prepared in a similar manner to that described in Example 3 using the corresponding starting materials.

Example 35

5-(3-Cyanoindol-1-yl)furan-2-carboxylic acid

To a suspension of 1-(5-formylfuran-2-yl)-1H-indole-3-carbonitrile (0.085 g) in methanol (4 mL) and tetrahydrofuran (4 mL) were added silver oxide (0.1 g) and 2 mol/L aqueous sodium hydroxide solution (0.27 mL), this mixture was stirred at room temperature for 6 hours. The insoluble material of reaction mixture was removed by filtration, and the filtrate was concentrated under reduced pressure. To this residue were added water (15 mL) and 2 mol/L hydrochloric acid solution (2 mL), this mixture was extracted with ethyl acetate. This organic layer was washed with brine, dried over anhydrous magnesium sulfate. The solvent was removed under reduced pressure. The residue was purified by column chromatography on silica gel (eluent: dichloromethane/methanol=10/1) to give the title compound (0.023 g).

Example 36

3-(3-Cyanoindol-1-yl)benzoic acid ethyl ester

To a solution of 1H-indole-3-carbonitrile (0.28 g) in dimethyl sulfoxide (3 mL) were added 3-iodobenzoic acid ethyl ester (0.61 g), cesium carbonate (0.65 g), copper iodide (0.038 g) and N,N-dimethyl grycine (0.041 g), this mixture was stirred at 75° C. for 3 days. To this reaction mixture was added ethyl acetate, the insoluble material was removed by filtration and this filtrate was concentrated under reduced pressure. To this residue was added water, the precipitated solid was collected by filtration, and washed with water and n-hexane, and dried under reduced pressure at 40° C. to give the title compound (0.38 g).

Example 37

3-(3-Cyanoindol-1-yl)benzoic acid

The title compound (0.30 g) was prepared in a similar manner to that described in Example 3 using the corresponding starting materials.

Example 38

2-(3-Cyanoindol-1-yl)isonicotinic acid ethyl ester

A mixture of 1H-indole-3-carbonitrile (0.1 g), 2-bromoisonicotinic acid ethyl ester (0.16 g), potassium phosphate (0.27 g), (1R,2R)-(−)-N,N'-dimethylcyclohexane-1,2-diamine (0.017 g), copper iodide (0.006 g) and toluene (0.7 mL) was stirred at 110° C. for 38 hours. The insoluble material was removed by filtration, and this filtrate was concentrated under reduced pressure. The residue was purified by column chromatography on silica gel (eluent: ethyl acetate/n-hexane=10/90 to 66/34) to give the title compound (0.061 g).

Example 39

2-(3-Cyanoindol-1-yl)isonicotinic acid

The title compound (0.038 g) was prepared in a similar manner to that described in Example 8 using the corresponding starting materials.

Example 40

4-(3-Cyanoindol-1-yl)-2-nitrobenzoic acid methyl ester

The title compound was prepared in a similar manner to that described in Example 1 using the corresponding starting materials.

Example 41

4-(3-Cyanoindol-1-yl)-2-nitrobenzoic acid

The title compound was prepared in a similar manner to that described in Example 3 using the corresponding starting materials.

Example 42

2-Amino-4-(3-cyanoindol-1-yl)benzoic acid

To a solution of 4-(3-cyanoindol-1-yl)-2-nitrobenzoic acid (0.012 g) in a mixed solvent of ethanol (1 mL), water (0.5 mL) and tetrahydrofuran (0.5 mL) were added zinc powder (0.041 g) and ammonium chloride (0.004 g) at room temperature, and this mixture was stirred at 80° C. for 2.5 hours. After cooling to ambient temperature, to this reaction mixture was added ethyl acetate. This insoluble material was removed by filtration and this filtrate was washed with brine, dried over anhydrous magnesium sulfate. The solvent was removed under reduced pressure to give the title compound (0.003 g).

Example 43

2-Acetoxy-(3-cyanoindol-1-yl)benzoic acid

To a suspension of 4-(3-cyanoindol-1-yl)-2-hydroxybenzoic acid in pyridine (0.5 mL) was added acetic anhydride (0.1 mL) at 0° C., and this mixture was stirred at room temperature for 1 hour. This reaction mixture was poured into 1 mol/L hydrochloric acid, and this mixture was extracted with ethyl acetate. This organic layer was washed with brine, dried over anhydrous magnesium sulfate. The solvent was removed under reduced pressure to give the title compound (0.047 g).

Example 44

2-(3-Cyanoindol-1-yl)nicotinic acid ethyl ester

The title compound was prepared in a similar manner to that described in Reference Example 13 using 6-chloronicotinic acid ethyl ester instead of 4-fluorobenzoic acid ethyl ester.

Example 45

2-(3-Cyanoindol-1-yl)nicotinic acid

The title compound was prepared in a similar manner to that described in Example 3 using the corresponding starting materials.

Example 46

2-(3-Cyanoindol-1-yl)-4-methylthiazole-5-carboxylic acid ethyl ester

The title compound was prepared in a similar manner to that described in Reference Example 13 using 2-chloro-4-methylthiazole-5-carboxylic acid ethyl ester instead of 4-fluorobenzoic acid ethyl ester.

Example 47

2-(3-Cyanoindol-1-yl)-4-methylthiazole-5-carboxylic acid

The title compound was prepared in a similar manner to that described in Example 3 using the corresponding starting materials.

Examples 48 to 55

The compounds of Examples 48 to 55 were prepared in a similar manner to that described in Example 13 using the corresponding starting materials.

Examples 56 to 65

The compounds of Examples 56 to 65 were prepared in a similar manner to that described in Example 7 using the corresponding starting materials.

Examples 66 to 76

The compounds of Examples 66 to 76 were prepared in a similar manner to that described in Example 14 using the corresponding starting materials.

Examples 77 to 81

The compounds of Examples 77 to 81 were prepared in a similar manner to that described in Example 33 using the corresponding starting materials.

Examples 82 to 84

The compounds of Examples 82 to 84 were prepared in a similar manner to that described in Example 26 using the corresponding starting materials.

Examples 85 to 86

The compounds of Example 85 to 56 were prepared in a similar manner to that described in Example 44 using the corresponding starting materials.

Example 87

The compound of Example 87 was prepared in a similar manner to that described in Example 13 using the corresponding starting materials.

Example 88

The compound of Example 88 was prepared in a similar manner to that described in Example 20 using the corresponding starting materials.

Examples 89 to 107

The compounds of Examples 89 to 107 were prepared in a similar manner to that described in Example 1 using the corresponding starting materials.

Examples 108 to 109

The compounds of Examples 108 to 109 were prepared in a similar manner to that described in Example 6 using the corresponding starting materials.

Examples 110 to 134

The compounds of Examples 110 to 134 were prepared in a similar manner to that described in Example 7 using the corresponding starting materials.

Examples 135 to 136

The compounds of Examples 135 to 136 were prepared in a similar manner to that described in Example 26 using the corresponding starting materials.

Example 137

The compound of Example 137 was prepared in a similar manner to that described in Example 10 using the corresponding starting materials.

Examples 138 to 140

The compounds of Examples 138 to 140 were prepared in a similar manner to that described in Example 11 using the corresponding starting materials.

Examples 141 to 187

The compounds of Examples 141 to 187 were prepared in a similar manner to that described in Example 3 using the corresponding starting materials.

Examples 188 to 225

The compounds of Examples 188 to 225 were prepared in a similar manner to that described in Example 2 and Example 3 using the corresponding starting materials.

Examples 226 to 227

The compounds of Examples 226 to 227 were prepared in a similar manner to that described in Example 8 using the corresponding starting materials.

Examples 228 to 234

The compounds of Examples 228 to 234 were prepared in a similar manner to that described in Example 2 and Example 3 using the corresponding starting materials.

Example 235

The compound of Example 235 was prepared in a similar manner to that described in Example 8 using the corresponding starting materials.

Examples 236 to 237

The compounds of Examples 236 to 237 were prepared in a similar manner to that described in Example 2 and Example 3 using the corresponding starting materials.

Examples 238 to 240

The compounds of Examples 238 to 240 were prepared in a similar manner to that described in Example 8 using the corresponding starting materials.

Example 241

The compound of Example 235 was prepared in a similar manner to that described in Example 3 using the corresponding starting materials.

Example 242

4-(3-Cyano-5-methoxy-6-methylindol-1-yl)benzoic acid ethyl ester

The title compound was prepared in a similar manner to that described in Example 13 using the corresponding starting materials.

Example 243

4-(5-Benzyloxy-6-chloro-3-cyanoindol-1-yl)benzoic acid ethyl ester

The title compound (0.31 g) was prepared in a similar manner to that described in Example 13 using the corresponding starting materials.

Example 244

4-(6-Chloro-3-cyano-5-hydroxyindol-1-yl)benzoic acid ethyl ester

To a solution of 4-(5-benzyloxy-6-chloro-3-cyanoindol-1-yl)benzoic acid ethyl ester (0.310 g) in dichloromethane (7 mL) was added boron tribromide (1 mol/L dichloromethane solution) (0.860 mL) under ice cooling, and this mixture was stirred at the same temperature for 1 hour. To this reaction mixture was added water, this mixture was extracted with ethyl acetate. This organic layer was washed with brine, dried over anhydrous magnesium sulfate and filtered. This filtrate was removed under reduced pressure. The residue was washed with diethyl ether to give the title compound (0.181 g).

Example 245

4-(6-Chloro-3-cyano-5-methoxyindol-1-yl)benzoic acid ethyl ester

The title compound was prepared in a similar manner to that described in Example 31 using the corresponding starting materials.

Example 246

4-(6-Chloro-3-cyano-5-trifluoromethanesulfonyloxy-indol-1-yl)benzoic acid ethyl ester To a solution of 4-(6-chloro-3-cyano-5-hydroxyindol-1-yl)benzoic acid ethyl ester (0.079 g) and pyridine (0.056 mL) in dichloromethane (2.3 mL) was added trifluoromethanesulfonic anhydride (0.058 mL) under ice cooling, and this mixture was stirred at the same temperature for 1 hour. To this reaction mixture was added 1 mol/L hydrochloric acid (0.370 mL) and water. After separating organic layer, this organic solvent was removed under reduced pressure to give the title compound (0.103 g).

Example 247

4-(6-Chloro-3-cyano-5-methylindol-1-yl)benzoic acid ethyl ester

To a solution of 4-(6-chloro-3-cyano-5-trifluoromethanesulfonyloxyindol-1-yl)benzoic acid ethyl ester (0.103 g), trimethylboroxine (0.033 g) and tripotassium phosphate (0.070 g) in dioxane (2.0 mL) was added tetrakis(triphenylphosphine) palladium catalyst (0.038 g), and this mixture was stirred at 80° C. for 1 day. The reaction mixture was purified by column chromatography on silica gel (eluent: ethyl acetate/n-hexane=75/25) to give the title compound (0568 g).

Example 248

4-(3-Cyano-6-fluoro-5-methylindol-1-yl)benzoic acid ethyl ester

The title compound (0.117 g) was prepared in a similar manner to that described in Example 13 using the corresponding starting materials.

Example 249

6-(3-Cyano-6-fluoro-5-methylindol-1-yl)nicotinic acid ethyl ester

The title compound (0.152 g) was prepared in a similar manner to that described in Example 44 using the corresponding starting materials.

Example 250

4-(3-Cyano-6-fluoro-5-methylindol-1-yl)-2-methoxymethoxybenzoic acid ethyl ester The title compound (0.116 g) was prepared in a similar manner to that described in Example 1 using the corresponding starting materials.

Example 251

4-(6-Benzyloxy-3-cyano-5-methoxyindol-1-yl)benzoic acid ethyl ester

The title compound was prepared in a similar manner to that described in Example 13 using the corresponding starting materials.

Example 252

4-(3-Cyano-6-hydroxy-5-methoxyindol-1-yl)benzoic acid ethyl ester

The title compound was prepared in a similar manner to that described in Example 6 using the corresponding starting materials.

Example 253

4-(3-Cyano-6-cyclopropyl-5-methoxyindol-1-yl) benzoic acid ethyl ester

To a solution of 4-(3-cyano-6-hydroxy-5-methoxyindol-1-yl)benzoic acid ethyl ester (0.195 g) and pyridine (0.138 g) in dichloromethane (2.3 mL) was added trifluoromethanesulfonic anhydride (0.246 g) under ice cooling, and this mixture was stirred at the same temperature for 1 hour. To this reaction mixture was added 1 mol/L hydrochloric acid (0.370 mL) and water, and this organic layer was separated. This organic solvent was concentrated under reduced pressure to give 4-(3-cyano-5-methoxy-6-trifluoromethanesulfonyloxyindol-1-yl)benzoic acid ethyl ester (0.238 g). After to this product (0.070 g) was added toluene (1.5 mL), to this mixture was added cyclopropylboronic acid (0.016 g), potassium carbonate (0.031 g) and tetrakis(triphenylphosphine) palladium (0) (0.026 g), and this mixture was stirred at 80° C. for 1 day. The reaction mixture was purified by column chromatography on silica gel (eluent: ethyl acetate/n-hexane=75/25) to give the title compound (0.037 g).

Example 254

4-(Cyano-5-hydroxy-6-methylindol-1-yl)benzoic acid ethyl ester

The title compound was prepared in a similar manner to that described in Example 244 using 4-(3-cyano-5-methoxy-6-methylindol-1-yl)benzoic acid ethyl ester.

Example 255

4-(3-Cyano-5,6-dimethylindol-1-yl)benzoic acid ethyl ester

The title compound was prepared in a similar manner to that described in Example 246 and Example 247 using 4-(cyano-5-hydroxy-6-methylindol-1-yl)benzoic acid ethyl ester.

Example 256

The title compound was prepared in a similar manner to that described in Example 13 using the corresponding starting materials.

Example 257

4-(3-cyano-6-fluoro-5-hydroxyindol-1-yl)benzoic acid

To a solution of 4-(3-cyano-6-fluoro-5-methoxyindol-1-yl)benzoic acid ethyl ester (1.2 g) in dichloromethane (20 mL) was added boron tribromide (1.0 mol/L dichloromethane solution) (10 mL) in a dropwise manner under ice cooling, and this mixture was stirred at room temperature for 12 hours. This reaction mixture was poured into water, and this mixture was extracted with ethyl acetate, concentrated under reduced pressure to give the title compound (0.44 g).

Example 258

4-[3-Cyano-6-fluoro-5-(2-methoxyethoxy)indol-1-yl]benzoic acid 2-methoxyethyl ester To a solution of 4-(3-cyano-6-fluoro-5-hydroxyindol-1-yl) benzoic acid (0.06 g) in N,N-dimethylformamide (2 mL) were added 1-bromo-2-methoxyethane (0.14 g) and potassium carbonate (0.13 g) at room temperature, this mixture was stirred at the same temperature for 16 hours. This reaction mixture was poured into water, and this mixture was extracted with ethyl acetate. This organic layer was washed with water and brine, dried over anhydrous magnesium sulfate. The solvent was removed under reduced pressure. The residue was purified by column chromatography on silica gel (eluent: ethyl acetate/n-hexane) to give the title compound (0.79 g).

Examples 259 to 264

The title compounds were prepared in a similar manner to that described in Example 13 using the corresponding starting materials.

Example 265

The title compound was prepared in a similar manner to that described in Example 245 using the corresponding starting materials.

Example 266

The title compound was prepared in a similar manner to that described in Example 252 using the corresponding starting materials.

Examples 267 to 270

The title compounds were prepared in a similar manner to that described in Example 1 using the corresponding starting materials.

Example 271

The title compound was prepared in a similar manner to that described in Example 244 using the corresponding starting materials.

Examples 272 to 277

The title compounds were prepared in a similar manner to that described in Example 1 using the corresponding starting materials.

Example 278

The title compound was prepared in a similar manner to that described in Example 252 using the corresponding starting materials.

Example 279

The title compound was prepared in a similar manner to that described in Example 1 using the corresponding starting materials and 2,4-difluoro-6-methoxymethoxy benzoic acid ethyl ester instead of 4-fluoro-2-methoxymethoxy benzoic acid ethyl ester.

Examples 280 to 282

The title compounds were prepared in a similar manner to that described in Example 258 using the corresponding starting materials.

Example 283

4-(3-Cyano-5-dimethylamino-6-trifluoromethylindol-1-yl)benzoic acid ethyl ester To a solution of 4-(3-formyl-5-methylamino-6-trifluoromethylindol-1-yl)benzoic acid ethyl ester (0.026 g) in tetrahydrofuran (1 mL) was added hydroxylamine hydrochloride (0.0067 g) and pyridine (0.02 g), and this mixture was stirred at 60° C. for 4 hours. After cooling to ambient temperature, acetic anhydride (0.013 g) was added to reaction mixture and this mixture was stirred at 60° C. for 12 hours. This reaction mixture was poured into water, and the precipitated solid was collected by filtration. This solid was washed with water and n-hexane, dried under reduced pressure at 50° C. to give the title compound (0.026 g).

Examples 284 to 291

The title compounds were prepared in a similar manner to that described in Example 3 using the corresponding starting materials.

Example 292

The title compound was prepared in a similar manner to that described in Example 257 using the corresponding starting materials.

Examples 293 to 308

The title compounds were prepared in a similar manner to that described in Example 3 using the corresponding starting materials.

Example 309

After the corresponding carboxylic acid was prepared in a similar manner to that described in Example 3, to this product was added 2 mol/L hydrochloric acid until the pH became 1, and this mixture was stirred overnight. The precipitated solid was collected by filtration to give the title compound.

Examples 310 to 321

The title compounds were prepared in a similar manner to that described in Example 309 using the corresponding starting materials.

Example 322

The title compound was prepared in a similar manner to that described in Example 2 and Example 3 using the corresponding starting materials.

Example 323

The title compound was prepared in a similar manner to that described in Example 6 using the corresponding starting materials.

Example 324

The title compound was prepared in a similar manner to that described in Example 309 using the corresponding starting materials, followed by alkylation in a similar manner to that described in Example 7.

Example 325

The title compound was prepared in a similar manner to that described in Example 309 using the corresponding starting materials.

Example 326

The title compound was prepared in a similar manner to that described in Example 324 using the corresponding starting materials.

Example 327

The title compound was prepared in a similar manner to that described in Example 309 using the corresponding starting materials.

Example 328

The title compound was prepared in a similar manner to that described in Example 41 and Example 21 using the corresponding starting materials.

Tables 1 to 3 and 42 to 45 show the chemical structures and $^1$H-NMR data of the above compounds of Reference Examples 1 to 23 and 24 to 53, Table 46 shows the chemical structures of Reference Examples 54 to 63, Tables 4 to 41, 47 to 49 and 53 to 59 show the chemical structures and $^1$H-NMR data of the above compounds of Examples 1 to 241, 242 to 258 and 284 to 328, Tables 50 to 52 show the chemical structures of Examples 259 to 283, respectively.

The abbreviations in these Tables: "Ref No.", "Ex No.", "Strc" and "Solv", represent Reference Example number, Example number, chemical structure and measurement solvent of $^1$H-NMR, respectively.

TABLE 1

| Ref No. | Strc | (Solv) ¹H-NMR δ ppm: |
|---|---|---|
| 1 | ethyl 4-fluoro-2-hydroxybenzoate | (CDCl3) 1.41 (3H, t, J = 7.2 Hz), 4.41 (2H, q, J = 7.2 Hz), 6.55-6.65 (1H, m), 6.67 (1H, dd, J = 10.4 Hz, 2.6 Hz), 7.86 (1H, dd, J = 9.0 Hz, 6.6 Hz), 11.08 (1H, d, J = 2.5 Hz) |
| 2 | ethyl 4-fluoro-2-(methoxymethoxy)benzoate | (CDCl3) 1.37 (3H, t, J = 7.0 Hz), 3.52 (3H, s), 4.35 (2H, q, J = 7.0 Hz), 5.25 (2H, s), 6.07-6.78 (1H, m), 6.94 (1H, dd, J = 2.4, 10.8 Hz), 7.83 (1H, d, J = 7.0, 8.9 Hz) |
| 3 | methyl 4-fluoro-2-(methoxymethoxy)benzoate | (CDCl3) 3.52 (3H, s), 3.88 (3H, s), 5.25 (2H, s), 6.70-6.80 (1H, m), 6.90-7.00 (1H, m), 7.75-7.95 (1H, m), |
| 4 | 5,6-difluoro-1H-indole-3-carbaldehyde | (DMSO-d6) 7.58 (1H, dd, J = 10.9 Hz, 7.0 Hz), 7.94 (1H, dd, J = 10.9 Hz, 8.0 Hz), 8.37 (1H, s) 9.92 (1H, s), 12.28 (1H, brs.) |
| 5 | 5,6-difluoro-1H-indole-3-carbonitrile | (DMSO-d6) 7.61 (1H, dd, J = 10.7 Hz, 7.0 Hz), 7.69 (1H, dd, J = 10.6 Hz, 7.7 Hz), 8.32 (1H, s), 12.34 (1H, brs.) |
| 6 | 6-fluoro-1H-indole-3-carbonitrile | (DMSO-d6) 7.05-7.20 (2H, m), 7.65-7.75 (2H, m), 8.62 (1H, s) |
| 7 | 5-phenyl-1H-indole-3-carbonitrile | (DMSO-d6) 7.30-8.35 (9H, m), 12.2 (1H, brs.) |
| 8 | benzyl 3-formyl-1H-indole-5-carboxylate | (DMSO-d6) 5.38 (2H, s), 7.25-7.55 (5H, m), 7.62 (1H, d, J = 8.7 Hz), 7.85-7.95 (1H, m), 8.44 (1H, s), 8.80 (1H, s), 9.98 (1H, s), 12.4 (1H, s) |

TABLE 1-continued
| Ref No. | Strc | (Solv) $^1$H-NMR δ ppm: |
|---|---|---|
| 9 | 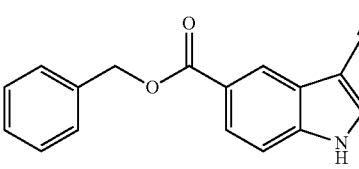 | (CDCl3) 5.42 (2H, d), 7.30-7.55 (6H, m), 7.80 (1H, d, J = 2.9 Hz), 8.08 (1H, dd, J = 8.7 Hz, 1.5 Hz), 8.50-8.65 (1H, m), 8.93 (1H, brs.) |
| 10 | 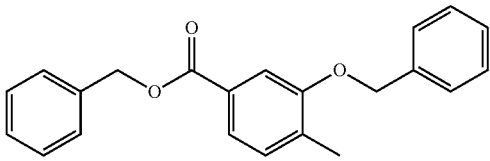 [SMILES: Cc1ccc(C(=O)OCc2ccccc2)cc1OCc1ccccc1] | (DMSO-d6) 2.32 (3H, s), 5.11 (2H, s), 5.34 (2H, s), 7.15-7.70 (13H, m) |
TABLE 2
| Ref No. | Strc | (Solv) $^1$H-NMR δ ppm: |
|---|---|---|
| 11 | 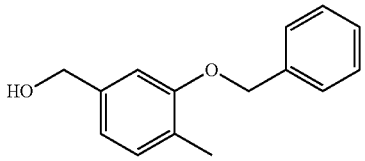 [SMILES: Cc1ccc(CO)cc1OCc1ccccc1] | (CDCl3) 2.28 (3H, s), 4.70 (2H, s), 5.10 (2H, s), 6.80-7.20 (3H, m), 7.25-7.50 (5H, m) |
| 12 | 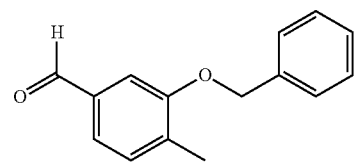 [SMILES: Cc1ccc(C=O)cc1OCc1ccccc1] | (CDCl3) 2.36 (3H, s), 5.15 (2H, s), 7.30-7.50 (8H, m), 9.92 (1H, s) |
| 13 | 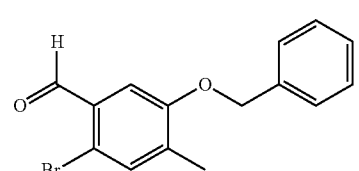 | (DMSO-d6) 2.28 (3H, s), 5.22 (2H, s), 7.25-7.50 (6H, m), 7.64 (1H, s), 10.13 (1H, s) |
| 14 | 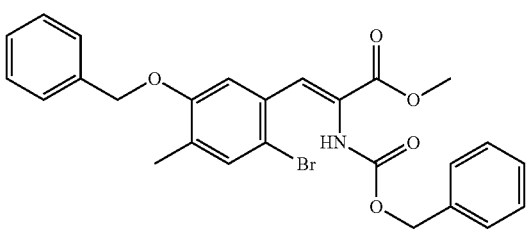 [SMILES: COC(=O)/C(=C/c1cc(OCc2ccccc2)c(C)cc1Br)NC(=O)OCc1ccccc1] | (CDCl3) 2.24 (3H, s), 3.85 (3H, s), 4.82 (2H, s), 5.06 (2H, s), 6.34 (1H, brs.), 7.07 (1H, s), 7.20-7.45 (12H, m) |
| 15 | 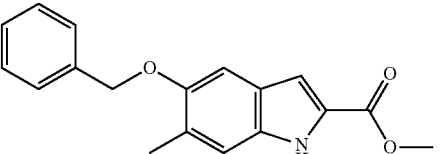 | (CDCl3) 2.35-2.45 (3H, m), 3.92 (3H, s), 5.11 (2H, s), 7.08 (1H, s), 7.10 (1H, dd, J = 2.0 Hz, 0.8 Hz), 7.20 (1H, s), 7.30-7.50 (5H, m), 8.65 (1H, brs.) |
| 16 | 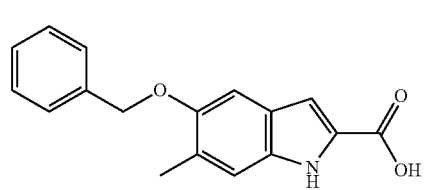 [SMILES: Cc1cc2[nH]c(C(=O)O)cc2cc1OCc1ccccc1] | (DMSO-d6) 2.30 (3H, s), 5.11 (2H, s), 7.02 (1H, s), 7.16 (1H, s), 7.23 (1H, s), 7.33 (1H, t, J = 7.3 Hz), 7.41 (2H, t, J = 7.3 Hz), 7.48 (2H, d, J = 7.3 Hz), 11.67 (1H, s) |

TABLE 2-continued

| Ref No. | Strc | (Solv) ¹H-NMR δ ppm: |
|---|---|---|
| 17 | | (CDCl3) 2.39 (3H, s), 5.12 (2H, s), 6.40-6.50 (1H, m), 7.05-7.15 (2H, m), 7.18 (1H, s), 7.25-7.35 (1H, m), 7.35-7.45 (2H, m), 7.45-7.55 (2H, m), 7.94 (1H, brs.) |
| 18 | | (DMSO-d6) 2.31 (3H, s), 5.14 (2H, s), 7.31 (1H, s), 7.33 (1H, d, J = 7.3 Hz), 7.40 (2H, t, J = 7.3 Hz), 7.51 (2H, d, J = 7.6 Hz), 7.66 (1H, s), 8.13 (1H, d, J = 2.9 Hz), 9.87 (1H, s), 11.92 (1H, s) |
| 19 | | (DMSO-d6) 2.34 (3H, s), 5.15 (2H, s), 7.21 (1H, s), 7.24 (1H, s), 7.34 (1H, d, J = 7.4 Hz), 7.40 (2H, t, J = 7.7 Hz), 7.49 (2H, d, J = 7.4 Hz), 7.60 (1H, d, J = 2.9), 8.41 (1H, brs.) |

TABLE 3

| Ref No. | Strc | (Solv) ¹H-NMR δ ppm: |
|---|---|---|
| 20 | | (DMSO-d6) 1.37 (3H, t, J = 7.1 Hz), 4.38 (2H, q, J = 7.1 Hz), 6.95-7.05 (1H, m), 7.80-7.95 (3H, m), 8.06 (1H, dd, J = 8.0 Hz, 2.0 Hz), 8.15-8.25 (3H, m), 8.40-8.50 (1H, m) |
| 21 | | (CDCl3) 6.56 (1H, d, J = 3.7 Hz), 7.40-7.55 (3H, m), 7.80-7.95 (2H, m), 8.05 (1H, s), 9.65 (1H, s) |
| 22 | | (DMSO-d6) 1.36 (3H, t, J = 7.1 Hz), 4.38 (2H, q, J = 7.1 Hz), 6.90-6.95 (1H, m), 7.65-7.90 (4H, m), 8.08 (1H, d, J = 3.4 Hz), 8.15-8.30 (3H, m), 10.0 (1H, s) |

TABLE 3-continued
| Ref No. | Strc | (Solv) ¹H-NMR δ ppm: |
|---|---|---|
| 23 | 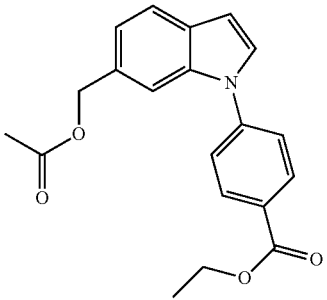 [SMILES: CCOC(=O)c1ccc(-n2ccc3ccc(COC(C)=O)cc32)cc1] | (DMSO-d6) 1.30-1.40 (3H, m), 2.03 (3H, s), 4.30-4.45 (2H, m), 5.16 (2H, s), 6.70-6.80 (1H, m), 7.10-7.25 (1H, m), 7.60-7.85 (5H, m), 8.15 (2H, d, J = 8.6 Hz) |
TABLE 4
| Ex No. | Strc | (Solv) ¹H-NMR δ ppm: |
|---|---|---|
| 1 | 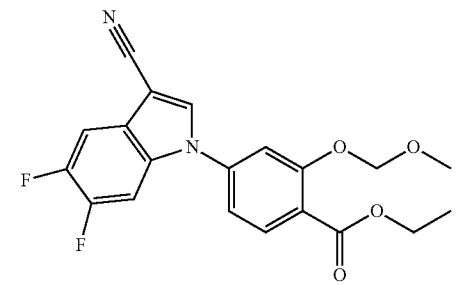 [SMILES: CCOC(=O)c1ccc(-n2cc(C#N)c3cc(F)c(F)cc32)cc1OCOC] | (CDCl3) 1.33 (1H, t, J = 7.1 Hz), 3.44 (3H, s), 4.32 (2H, q, J = 7.1 Hz), 5.39 (2H, s), 7.30-7.55 (2H, m), 7.70-7.95 (3H, m), 8.75 (1H, s) |
| 2 | 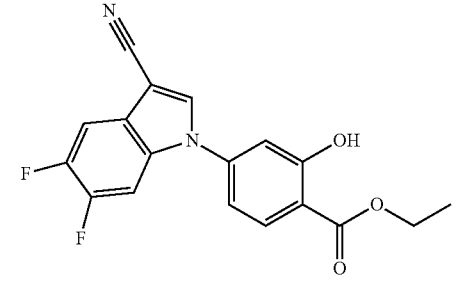 [SMILES: CCOC(=O)c1ccc(-n2cc(C#N)c3cc(F)c(F)cc32)cc1O] | (DMSO-d6) 1.37 (3H, t, J = 7.1 Hz), 4.41 (2H, q, J = 7.1 Hz), 7.20-7.35 (2H, m), 7.70-8.05 (3H, m), 8.75 (1H, s) |
| 3 | 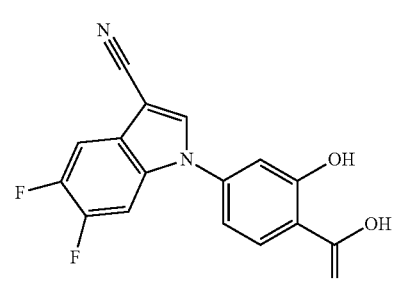 | (DMSO-d6) 7.15-7.35 (2H, m), 7.75-7.95 (2H, m), 8.00 (1H, d, J = 8.2 Hz), 8.75 (1H, s) |

TABLE 4-continued

| Ex No. | Strc | (Solv) ¹H-NMR δ ppm: |
|---|---|---|
| 4 | | (CDCl3) 1.42 (3H, t, J = 7.1 Hz), 3.54 (3H, s), 4.42 (2H, q, J = 7.1 Hz), 5.07 (2H, s), 5.29 (2H, s), 7.00-7.20 (3H, m), 7.25-7.55 (6H, m), 7.70 (1H, d, J = 8.8 Hz), 7.73 (1H, s), 7.97 (1H, d, J = 8.2 Hz) |
| 5 | | (DMSO-d6) 5.17 (2H, s), 7.11 (1H, dd, J = 8.7 Hz, 2.0 Hz), 7.15-7.55 (8H, m), 7.64 (1H, d, J = 8.7 Hz), 7.99 (1H, d, J = 8.4 Hz), 8.52 (1H, s) |
| 6 | | (DMSO-d6) 1.42 (3H, t, J = 7.2 Hz), 3.45 (3H, s), 4.31 (2H, q, J = 7.2 Hz), 5.37 (2H, s), 6.88 (1H, dd, J = 8.7 Hz, 1.7 Hz), 7.05 (1H, d, J = 1.7 Hz), 7.34 (1H, dd, J = 8.4 Hz, 1.8 Hz), 7.44 (1H, d, J = 1.8 Hz), 7.53 1H, d, J = 8.4 Hz), 7.86 (1H, d, J = 8.4 Hz), 8.44 (1H, s), 9.68 (1H, brs.) |
| 7 | | (CDCl3) 1.42 (3H, t, J = 7.2 Hz), 3.54 (3H, s), 3.62 (2H, m,), 4.04 (2H, t, J = 4.9 Hz), 4.41 (2H, q, J = 7.2 Hz), 5.10 (2H, s), 5.22 (1H, br. s.), 5.31 (2H, s), 6.90-7.10 (2H, m), 7.14 (1H, dd, J = 8.5, 1.9 Hz), 7.20-7.40 (6H, m), 7.68 (1H, d, J = 8.5 Hz), 7.73 (1H, s), 7.99 (1H, d, J = 8.5 Hz) |

TABLE 5

| Ex No. | Strc | (Solv) ¹H-NMR δ ppm: |
|---|---|---|
| 8 | | (DMSO-d6) 3.30-3.50 (2H, m), 3.95-4.1 (2H, m), 5.01 (2H, s), 8.95-7.55 (10H, m), 7.64 (1H, d, J = 8.6 Hz), 8.01 (1H, d, J = 8.5 Hz), 8.53 (1H, s) |
| 9 | | (DMSO-d6) 3.10-3.50 (2H, m), 4.10-4.30 (2H, m), 7.05-7.35 (4H, m), 7.70 (1H, d, J = 8.6 Hz), 7.95-8.25 (3H, m), 8.57 (1H, s) |
| 10 | | (CDCl3) 1.42 (3H, t, J = 7.1 Hz), 3.10 (2H, t, J = 5.1 Hz), 3.99 (2H, t, J = 5.1 Hz), 4.42 (2H, q, J = 7.1 Hz), 5.32 (2H, s), 7.02 (1H, dd, J = 8.7 Hz, 2.2 Hz), 7.05 (1H, d, J = 2.2 Hz), 7.16 (1H, dd, J = 8.3 Hz, 1.9 Hz), 7.36 (1H, d, J = 1.9 Hz), 7.69 (1H, d, J = 8.7 Hz), 7.73 (1H, s), 7.98 (1H, d, J = 8.3 Hz) |
| 11 | | (CDCl3) 1.42 (3H, t, J = 7.1 Hz), 2.01 (3H, s), 3.55 (3H, s), 3.60-3.75 (2H, m), 3.68 (2H, q, J = 5.8 Hz), 4.03 (2H, t, J = 5.0 Hz), 4.42 (2H, q, J = 7.1 Hz), 5.32 (2H, s), 5.92 (1H, br. s.), 7.00 (1H, dd, J = 8.5, 2.2 Hz), 7.03 (1H, d, J = 2.2 Hz), 7.15 (1H, dd, J = 8.3, 2.1 Hz), 7.35 (1H, d, J = 2.1 Hz), 7.70 (1H, d, J = 8.5 Hz), 7.74 (1H, s), 7.99 (1H, d, J = 8.3 Hz) |
| 12 | | (DMSO-d6) 1.81 (3H, s), 3.30-3.50 (2H, m), 3.95-4.10 (2H, m), 6.95-7.35 (4H, m), 7.60-7.7 (1H, m), 7.95-8.2 (2H, m), 8.53 (1H, s) |

TABLE 5-continued

| Ex No. | Strc | (Solv) $^1$H-NMR δ ppm: |
|---|---|---|
| 13 | | (DMSO-d6) 1.36 (3H, t, J = 7.1 Hz), 4.37 (2H, q, J = 7.1 Hz), 7.55 (1H, dd, J = 8.9 Hz, 1.8 Hz), 7.66 (1H, d, J = 8.9 Hz), 7.80-7.90 (2H, m), 7.96 (1H, d, J = 1.8 Hz), 8.15-8.25 (2H, m), 8.77 (1H, s) |

TABLE 6

| Ex No. | Strc | (Solv) $^1$H-NMR δ ppm: |
|---|---|---|
| 14 | | (DMSO-d6) 1.35 (3H, t, J = 7.0 Hz), 3.82 (3H, s), 4.37 (2H, q, J = 7.0 Hz), 7.05 (2H, d, J = 8.5 Hz), 7.68 (1H, dd, J = 9.3 Hz, 1.6 Hz), 7.71 (2H, d, J = 8.5 Hz), 7.76 (1H, d, J = 8.5 Hz), 7.87 (2H, d, J = 8.5 Hz), 7.92 (1H, d, J = 1.6 Hz), 8.19 (2H, d, J = 8.5 Hz), 8.74 (1H, s) |
| 15 | | (DMSO-d6) 3.82 (3H, s), 7.05 (2H, d, J = 8.9 Hz), 7.67-7.72 (3H, m), 7.75 (1H, d, J = 8.9 Hz), 7.84 (2H, d, J = 8.4 Hz), 7.91 (1H, d, J = 1.5 Hz), 8.17 (2H, d, J = 8.9 Hz), 8.73 (1H, s), 13.3 (1H, s-br) |
| 16 | | (DMSO-d6) 1.26 (3H, t, J = 7.2 Hz), 1.35 (3H, t, J = 7.2 Hz), 4.20 (2H, q, J = 7.2 Hz), 4.37 (2H, q, J = 7.2 Hz), 6.74 (1H, d, J = 16.2 Hz), 7.70 (1H, d, J = 8.5 Hz), 7.80-7.90 (4H, m), 8.15-8.25 (3H, m), 8.77 (1H, s), |
| 17 | | (DMSO-d6) 6.61 (1H, d, J = 16.1 Hz), 7.69 (1H, d, J = 8.9 Hz), 7.76-7.82 (5H, m), 8.10 (1H, s), 8.16 (2H, d, J = 8.5 Hz), 8.74 (1H, s) |

TABLE 6-continued

| Ex No. | Strc | (Solv) $^1$H-NMR δ ppm: |
|---|---|---|
| 18 | | (DMSO-d6) 1.36 (3H, t, J = 7.1 Hz), 4.37 (2H, q, J = 7.1 Hz), 5 36 (2H, s), 7.00 (1H, d, J = 7.9 Hz), 7.20-7.50 (5H, m), 7.55-7.65 (2H, m), 7.75-7.90 (2H, m), 8.10-8.25 (2H, m), 8.60 (1H, s) |
| 19 | | (DMSO-d6) 5.37 (2H, s), 6.95-7.10 (1H, m), 7.20-7.5 (5H, m), 7.55-7.70 (2H, m), 7.80 (2H, d, J = 8.1 Hz), 8.16 (2H, d, J = 8.1 Hz), 8.61 (1H, s), 13.10-13.40 (1H, brs.) |
| 20 | | (DMSO-d6) 1.37 (3H, t, J = 7.1 Hz), 4.39 (2H, q, J = 7.1 H), 7.90-8.00 (2H, m), 8.03 (1H, m), 8.20-8.30 (3H, m), 8.43 (1H, d, J = 2.0 Hz), 9.08 (1H, s) |

TABLE 7

| Ex No. | Strc | (Solv) $^1$H-NMR δ ppm: |
|---|---|---|
| 21 | | (DMSO-d6) 1.36 (3H, t, J = 7.1 Hz), 4.37 (2H, q, J = 7.1 Hz), 5.32 (2H, brs.), 6.72 (1H, dd, J = 8.5 Hz, 1.8 Hz), 6.82 (1H, d, J = 1.8 Hz), 7.39 (1H, d, J = 8.5 Hz), 7.76 (2H, d, J = 8.6 Hz), 8.16 (2H, d, J = 8.6 Hz), 8.29 (1H, s) |

TABLE 7-continued

| Ex No. | Strc | (Solv) ¹H-NMR δ ppm: |
|---|---|---|
| 22 | | (DMSO-d6) 1.36 (3H, t, J = 7.1 Hz), 2.97 (3H, s), 4.38 (2H, q, J = 7.1 Hz), 7.28 (1H, dd, J = 8.6 Hz, 1.9 Hz), 7.56 (1H, d, J = 1.9 Hz), 7.75 (1H, d, J = 8.6 Hz), 7.80-7.90 (2H, m), 8.15-8.25 (2H, m), 9.82 (1H, s) |
| 23 | | (DMSO-d6) 2.97 (3H, s), 7.00-7.85 (5H, m), 8.00-8.25 (2H, m), 9.00-10.0 (1H, s), 8.65 (1H, s), 13.0-13.5 (1H, brs.) |
| 24 | | (CDCl3) 1.44 (3H, t, J = 7.1 Hz), 4.44 (2H, q, J = 7.1 Hz), 5.16 (2H, s), 7.08 (1H, dd, J = 9.1 Hz, 2.5 Hz), 7.30-7.65 (9H, m), 7.79 (1H, s), 8.20-8.3 (2H, m) |
| 25 | | (DMSO-d6) 1.35 (3H, t, J = 7.1 Hz), 4.37 (2H, q, J = 7.1 Hz), 6.90 (1H, dd, J = 8.9 Hz, 2.3 Hz), 7.01 (1H, d, J = 2.3 Hz), 7.54 (1H, d, J = 8.9 Hz), 7.75-7.85 (2H, m), 8.10-8.25 (2H, m), 8.56 (1H, s), 9.55 (1H, brs.) |
| 26 | | (CDCl3) 1.43 (3H, t, J = 7.2 Hz), 4.44 (2H, q, J = 7.2 Hz), 5.32 (2H, s), 6.90-7.40 (6H, m), 7.46 (1H, d, J = 8.9 Hz), 7.56 (2H, d, J = 8.5 Hz), 7.79 (1H, s), 8.24 (2H, d, J = 8.5 Hz) |

TABLE 7-continued

| Ex No. | Strc | (Solv) ¹H-NMR δ ppm: |
|---|---|---|
| 27 | | (DMSO-d6) 5.42 (2H, s), 6.95-7.45 (4H, m), 7.50-7.85 (4H, m), 8.10-8.20 (2H, m), 8.64 (1H, s), 13.2 (1H, s) |

TABLE 8

| Ex No. | Strc | (Solv) ¹H-NMR δ ppm: |
|---|---|---|
| 28 | | (CDCl3) 1.44 (3H, t, J = 7.2 Hz), 4.45 (2H, q, J = 7.2 Hz), 5.43 (2H, s), 7.30-7.65 (8H, m), 7.91 (1H, s), 8.11 (1H, d, J = 8.8 Hz), 8.28 (2H, d, J = 8.5 Hz), 8.61 (1H, s) |
| 29 | | (DMSO-d6) 7.65-8.50 (7H, m), 8.82 (1H, s), 13.1 (2H, m) |
| 30 | | (DMSO-d6) 1.36 (3H, t, J = 7.1 Hz), 4.38 (2H, t, J = 7.1 Hz), 7.75 (1H, d, J = 8.8 Hz), 7.87 (2H, d, J = 8.4 Hz), 7.95-8.05 (1H, m), 8.20 (2H, d, = 8.4 Hz), 8.25-8.35 (1H, m), 8.81 (1H, s) |

TABLE 8-continued

| Ex No. | Strc | (Solv) ¹H-NMR δ ppm: |
|---|---|---|
| 31 | | (CDCl3) 1.44 (3H, t, J = 7.2 Hz), 1.77 (1H, t, J = 5.5 Hz), 4.44 (2H, q, J = 7.2 Hz), 4.86 (2H, d, J = 5.5 Hz), 7.41 (1H, dd, J = 8.5, 1.3 Hz), 7.50-7.65 (3H, m), 7.80-7.90 (2H, m), 8.26 (2H, d, J = 8.5 Hz) |
| 32 | | (DMSO-d6) 4.65 (2H, s), 5.20-5.40 (1H, m), 7.30-7.90 (5H, m), 8.00-8.3 (2H, m), 8.66 (1H, s), 13.2 (1H, brs.) |
| 33 | | (DMSO-d6) 1.36 (3 H, t, J = 7.2 Hz), 2.85-3.15 (6 H, m), 4.38 (2 H, q, J = 7.2 Hz), 7.46 (1 H, dd, J = 8.5, 1.6 Hz), 7.70-7.85 (2 H, m), 7.87 (2 H, d, J = 8.8 Hz), 8.20 (2 H, d, J = 8.8 Hz), 8.80 (1 H, s) |
| 34 | | (DMSO-d6) 3.00 (6H, brs.), 7.45 (1H, dd, J = 8.7 Hz, 1.5 Hz), 7.73 (1H, d, J = 8.7 Hz), 7.75-7.85 (2H, d, J = 8.5 Hz), 8.77 (1H, s) |

TABLE 9

| Ex No. | Strc | (Solv) ¹H-NMR δ ppm: |
|---|---|---|
| 35 | | (DMSO-d6) 6.72 (1H, d, J = 3.1 Hz), 6.97 (1H, brs.), 7.40-7.45 (1H, m), 7.46-7.52 (1H, m), 7.77 (1H, d, J = 8.1 Hz), 7.84 (1H, d, J = 8.1 Hz), 8.69 (1H, s) |

TABLE 9-continued

| Ex No. | Strc | (Solv) $^1$H-NMR δ ppm: |
|---|---|---|
| 36 | (3-cyanoindol-1-yl)-phenyl ethyl ester structure | (DMSO-d6) 1.34 (3H, t, J = 7.1 Hz), 4.37 (2H, q, J = 7.1 Hz), 7.30-7.65 (3H, m), 7.70-7.85 (2H, m), 7.90-8.20 (3H, m), 8.69 (1H, s) |
| 37 | (3-cyanoindol-1-yl)-benzoic acid structure | (DMSO-d6) 7.35-7.50 (2H, m), 7.55-7.65 (1H, m), 7.70-7.85 (2H, m), 7.90-8.00 (1H, m), 8.05-8.15 (2H, m), 8.69 (1H, s) |
| 38 | (3-cyanoindol-1-yl)-pyridine ethyl ester structure | (DMSO-d6) 1.38 (3H, t, J = 7.1 Hz), 4.43 (2H, q, J = 7.1 Hz), 7.30-7.55 (2H, m), 7.70-7.80 (1H, m), 7.89 (1H, dd, J = 5.1 Hz, 1.3 Hz), 8.25 (1H, s), 8.43 (1H, d, J = 8.5 Hz), 8.80-8.90 (1H, m), 9.10 (1H, s) |
| 39 | (3-cyanoindol-1-yl)-pyridine carboxylic acid structure | (DMSO-d6) 7.30-7.95 (4H, m), 8.23 (1H, s), 8.41 (1H, d, J = 8.1 Hz), 8.83 (1H, d, J = 5.1 Hz), 9.08 (1H, s), 13.5-14.5 (1H, brs.) |
| 40 | (3-cyanoindol-1-yl)-nitro methyl ester structure | (DMSO-d6) 3.91 (3H, s), 7.42 (2H, m), 7.79-7.80 (2H, m), 8.12-8.19 (2H, m), 8.43 (1H, d, J = 1.9 Hz), 8.75 (1H, s) |
| 41 | (3-cyanoindol-1-yl)-nitro benzoic acid structure | (DMSO-d6) 7.42-7.46 (2H, m), 7.76 (2H, m), 8.10-8.12 (2H, m), 8.36 (1H, d, J = 1.4 Hz), 8.75 (1H, s) |

TABLE 9-continued

| Ex No. | Strc | (Solv) ¹H-NMR δ ppm: |
|---|---|---|
| 42 | | (DMSO-d6) 6.70 (1H, dd, J = 6.5, 2.3 Hz), 7.00 (1H, d, J = 2.0 Hz), 7.40-7.47 (2H, m), 7.72 (1H, d, J = 7.8 Hz), 7.76 (1H, d, J = 6.8 Hz), 7.95 (1H, d, J = 8.6 Hz), 8.48 (1H, s) |

TABLE 10

| Ex No. | Strc | (Solv) ¹H-NMR δ ppm: |
|---|---|---|
| 43 | | (DMSO-d6) 2.29 (3H, s), 7.30-7.85 (6H, m), 8.14 (1H, d, 8.0 Hz), 8.69 (1H, s) |
| 44 | | (DMSO-d6) 1.37 (3H, t, J = 7.1 Hz), 4.40 (2H, q, J = 7.1 Hz), 7.40-7.55 (2H, m), 7.70-7.80 (1H, m), 8.03 (1H, d, J = 8.8 Hz), 8.45-8.60 (2H, m), 9.07 (1H, s), 9.10-9.15 (1H, m) |
| 45 | | (DMSO-d6) 7.35-7.60 (2H, m), 7.70-7.80 (1H, m), 7.99 (1H, d, J = 8.6 Hz), 8.48 (1H, dd, J = 8.6 Hz, 2.3 Hz), 8.53 (1H, d, J = 8.4 Hz), 9.03 (1H, s), 9.10-9.15 (1H, m) |
| 46 | | (DMSO-d6) 1.33 (3H, t, J = 7.1 Hz), 2.71 (3H, s), 4.33 (2H, q, J = 7.1 Hz), 7.40-7.65 (2H, m), 7.78 (1H, d, J = 7.9 Hz), 8.50 (1H, d, J = 8.5 Hz), 8.97 (1H, s) |

TABLE 10-continued

| Ex No. | Strc | (Solv) ¹H-NMR δ ppm: |
|---|---|---|
| 47 | | (DMSO-d6) 2.69 (3H, s). 7.40-7.65 (2H, s), 7.78 (1H, d, J = 8.0 Hz), 8.49 (1H, d, J = 8.4 Hz), 8.96 (1H, s), 13.59 (1H, brs.) |
| 48 | | (DMSO-d6) 1.35 (3H, t, J = 7.3 Hz), 4.38 (2H, q, J = 7.3 Hz), 7.38 (1H, t, J = 7.4 Hz), 7.49 (2H, t, J = 7.6 Hz), 7.72-7.80 (4H, m), 7.88 (2H, d, J = 8.1 Hz), 7.98 (1H, d, J = 1.2 Hz), 8.20 (2H, d, J = 8.1 Hz), 8.75 (1H, s), |
| 49 | | (DMSO-d6) 1.35 (3H, t, J = 7.1 Hz), 4.37 (2H, q, J = 7.1 Hz), 7.38 (1H, t, J = 6.8 Hz), 7.46 (2H, t, J = 7.4 Hz), 7.70-7.73 (3H, m), 7.86 (2H, d, J = 8.2 Hz), 7.92 (2H, d, J = 8.2 Hz), 8.20 (2H, d, J = 8.2 Hz), 8.74 (1H, s) |

TABLE 11

| Ex No. | Strc | (Solv) ¹H-NMR δ ppm: |
|---|---|---|
| 50 | | (DMSO-d6) 3.92 (3H, s), 7.35-7.50 (2H, m), 7.65-7.90 (3H, s), 7.99 (1H, d, J = 2.1 Hz), 8.06 (1H, d, J = 8.4 Hz), 8.73 (1H, s) |
| 51 | | (DMSO-d6) 2.10 (3H, s), 3.92 (3H, s), 7.14-7.16 (1H, m), 7.34-7.40 (2H, m), 7.61 (1H, d, J = 8.1 Hz), 7.77-7.79 (1H, m), 7.99 (1H, dd, J = 6.1 Hz, 1.8 Hz), 8.11 (1H, d, J = 1.8 Hz), 8.55 (1H, s) |

TABLE 11-continued

| Ex No. | Strc | (Solv) ¹H-NMR δ ppm: |
|---|---|---|
| 52 | | (DMSO-d6) 3.94 (3H, s), 7.14-7.42 (3H, m), 7.78 (1H, m), 7.91 (1H, t, J = 8.1 Hz), 8.02-8.08 (2H, m), 8.65 (1H, s) |
| 53 | | (DMSO-d6) 3.33 (3H, s), 7.40-7.47 (2H, m), 7.71 (1H, dd, J = 8.5 Hz, 2.0 Hz), 7.77-7.79 (2H, m), 7.81 (1H, dd, J = 8.5 Hz, 2.0 Hz), 8.11 (1H, t, J = 8.2 Hz), 8.73 (1H, s) |
| 54 | | (DMSO-d6) 3.83 (3H, s), 3.93 (3H, s), 7.33 (1H, dd, J = 8.5 Hz, 1.6 Hz), 7.39-7.44 (3H, m), 7.76-7.78 (2H, m), 7.88 (1H, d, J = 8.1 Hz), 8.71 (1H, s) |
| 55 | | (DMSO-d6) 1.34 (3H, t, J = 7.1 Hz), 2.33 (3H, s), 4.36 (2H, q, J = 7.1 Hz), 5.26 (2H, s), 7.29 (1H, s), 7.34 (1H, t, J = 7.3 Hz), 7.42 (2H, t, J = 7.3 Hz), 7.51 (2H, d, J = 7.3 Hz), 7.55 (1H, s), 7.81 (2H, d, J = 8.3 Hz), 8.17 (2H, d, J = 8.3), 8.55 (1H, s), |
| 56 | | (CDCl3) 1.44 (3H, t, J = 7.1 Hz), 3.48 (3H, s), 3.75-3.85 (2H, m), 4.15-4.25 (2H, m), 4.44 (2H, q, J = 7.1 Hz), 7.06 (1H, dd, J = 9.0 Hz, 2.4 Hz), 7.24 (1H, d, J = 2.4 Hz), 7.45 (1H, d, J = 9.0 Hz), 7.50-7.65 (2H, m), 7.78 (1H, s), 8.20-8.3 (2H, m) |

TABLE 12

| Ex No. | Strc | (Solv) ¹H-NMR δ ppm: |
|---|---|---|
| 57 | | (CDCl3) 1.44 (3H, t, J = 7.1 Hz), 4.35-4.50 (6H, m), 6.95-7.05 (4H, m), 7.25-7.4 (3H, m), 7.46 (1H, d, J = 9.0 Hz), 7.05-7.60 (2H, m), 7.79 (1H, s), 8.20-8.30 (2H, m) |
| 58 | | (CDCl3) 1.44 (3 H, t, J = 7.1 Hz), 3.85 (3 H, s), 4.44 (2 H, q, J = 7.1 Hz), 4.75 (2 H, s), 7.10 (1 H, d, J = 9.1, 2.5 Hz), 7.18 (1 H, d, J = 2.5 Hz), 7.48 (1 H, d, J = 9.1 Hz), 7.56 (2 H, d, J = 8.5 Hz), 7.81 (1 H, s), 8.25 (2 H, d, J = 8.5 Hz) |
| 59 | | (CDCl3) 1.44 (3 H, t, J = 7.2 Hz), 2.13 (3 H, s), 4.20-4.55 (6 H, m), 7.04 (1 H, dd, J = 9.1, 2.4 Hz), 7.24 (1 H, d, J = 2.4 Hz), 7.47 (1 H, d, J = 9.1 Hz), 7.56 (2 H, d, J = 8.5 Hz), 7.80 (1 H, s), 8.25 (2 H, d, J = 8.5 Hz) |
| 60 | | (CDCl3) 1.44 (3 H, t, J = 7.0 Hz), 2.08 (3 H, s), 2.15-2.25 (2H, m), 4.15 (2 H, t, J = 6.1 Hz), 4.30 (2 H, t, J = 6.1 Hz), 4.44 (2 H, q, J = 7.0 Hz), 6.99 (1 H, dd, J = 8.9, 2.4 Hz), 7.15-7.30 (1 H, m), 7.45 (1 H, d, J = 8.9 Hz), 7.56 (2 H, d, J = 8.2 Hz), 7.79 (1 H, s), 8.25 (2 H, d, J = 8.2 Hz) |
| 61 | | (DMSO-d6) 1.15 (3 H, t, J = 7.0 Hz), 1.36 (3 H, t, J = 7.1 Hz), 3.53 (2 H, q, J = 7.0 Hz), 3.60-3.90 (2 H, m), 4.10-4.30 (2 H, m), 4.37 (2 H, q, J = 7.1 Hz), 6.95-7.15 (1 H, m), 7.23 (1 H, s), 7.50-7.70 (1 H, m), 7.70-7.95 (2H, m), 8.05-8.30 (2 H, m), 8.63 (1H, s) |

TABLE 12-continued

| Ex No. | Strc | (Solv) ¹H-NMR δ ppm: |
|---|---|---|
| 62 | | (DMSO-d6) 1.36 (3H, t, J = 7. Hz), 3.70-3.90 (2H, m), 4.20-4.35 (2H, m), 4.37 (2H, q, J = 7.0 Hz), 4.58 (2H, s), 7.05 (1H, dd, J = 9.1, 2.3 Hz), 7.15-7.45 (6H, m), 7.62 (1H, d, J = 9.1 Hz), 7.82 (2H, d, J = 8.5 Hz), 8.17 (2H, d, J = 8.5 Hz), 8.63 (1H, s) |

TABLE 13

| Ex No. | Strc | (Solv) ¹H-NMR δ ppm: |
|---|---|---|
| 63 | | (DMSO-d6) 1.36 (3H, t, J = 7.1 Hz), 3.30 (3H, s), 3.60-3.70 (2H, m), 4.10-4.20 (2H, m), 4.38 (2H, q, J = 7.1 Hz), 7.04 (1H, dd, J = 8.7 Hz, 2.0 Hz), 7.16 (1H, d, J = 2.0 Hz), 7.64 (1H, d, J = 8.7 Hz), 7.84 (2H, d, J = 7.8 Hz), 8.17 (2H, d, J = 7.8 Hz), 8.56 (1H, s) |
| 64 | | (DMSO-d6) 1.34 (3H, t, J = 7.1 Hz), 2.02 (3H, s), 4.20-4.25 (2H, m), 4.30-4.40 (4H, m), 7.05 (1H, dd, J = 8.7 Hz, 2.1 Hz), 7.16 (1H, d, J = 2.1 Hz), 7.65 (1H, d, J = 8.7 Hz), 7.80-7.90 (2H, m), 8.15-8.20 (2H, m), 8.57 (1H, s) |
| 65 | | (CDCl3) 1.44 (3H, t, J = 7.1 Hz), 3.08 (3H, s), 4.44 (2H, q, J = 7.1 Hz), 5.27 (2H, s), 7.10 (1H, dd, J = 8.9, 2.3 Hz), 7.29 (1H, d, J = 2.3 Hz), 7.49 (1H, d, J = 8.9 Hz), 7.56 (2H, d, J = 8.5 Hz), 7.70 (2H, d, J = 8.0 Hz), 7.81 (1H, s), 7.99 (2H, d, J = 8.0 Hz), 8.26 (2H, d, J = 8.5 Hz) |

TABLE 13-continued

| Ex No. | Strc | (Solv) ¹H-NMR δ ppm: |
|---|---|---|
| 66 | | (DMSO-d6) 1.37 (3H, t, J = 7.1 Hz), 3.86 (3H, s), 4.37 (2H, q, J = 7.1 Hz), 6.96 (1H, d, J = 7.2 Hz), 7.29-7.43 (3H, m), 7.72-7.79 (2H, m), 7.88 (2H, d. J = 8.2 Hz), 8.00 (1H, s), 8.20 (2H, d, J = 7.9 Hz), 8.75-8.77 (1H, m) |
| 67 | | (DMSO-d6) 1.38 (3H, t, J = 7.2 Hz), 3.79 (3H, s), 4.38 (2H, q, J = 7.2 Hz), 7.08 (1H, t, J = 7.5 Hz), 7.15 (1H, d, J = 8.8 Hz), 7.37-7.54 (3H, m), 7.73 (1H, d, J = 8.3 Hz), 7.77 (1H, d, J = 1.3 Hz), 7.88 (2H, d, J = 8.4 Hz), 8.19 (2H, d, J = 8.4 Hz), 8.74 (1H, s), |
| 68 | | (DMSO-d6) 1.35 (3H, t, J = 7.0 Hz), 4.37 (2H, q, J = 7.0 Hz), 7.15-7.29 (1H, m), 7.57 (1H, d, J = 5.0 Hz), 7.63 (1H, d, J = 3.5 Hz), 7.70-7.75 (2H, m), 7.86 (2H, d, J = 8.3 Hz), 7.95-8.00 (1H, m), 8.19 (2H, d, J = 8.3 Hz), 8.74 (1H, s), |

TABLE 14

| Ex No. | Strc | (Solv) ¹H-NMR δ ppm: |
|---|---|---|
| 69 | | (DMSO-d6) 1.37 (3H, t, J = 7.3 Hz), 4.38 (2H, q, J = 7.3 Hz), 7.80-7.95 (6H, m), 8.15-8.25 (3H, m), 8.60-8.70 (2H, m), 8.80 (1H, s) |
| 70 | | (DMSO-d6) 1.35 (3H, t, J = 7.1 Hz), 2.95 (6H, s), 4.37 (2H, q, J = 7.1 Hz), 6.83 (2H, d, J = 8.6 Hz), 7.55-7.75 (3H, m), 7.72 (1H, d, J = 8.8 Hz), 7.80-7.90 (3H, m), 8.19 (2H, d, J = 8.2 Hz), 8.70 (1H, s) |

TABLE 14-continued

| Ex No. | Strc | (Solv) ¹H-NMR δ ppm: |
|---|---|---|
| 71 | | (DMSO-d6) 1.35 (3H, t, J = 7.1 Hz), 2.63 (3H, s), 4.38 (2H, q, J = 7.1 Hz), 7.80-7.85 (2H, m), 7.85-8.00 (4H, m), 8.00-8.15 (3H, m), 8.15-8.25 (2H, m), 8.78 (1H, s) |
| 72 | | (DMSO-d6) 1.35 (3H, t, J = 7.2 Hz), 3.27 (3H, s), 4.38 (2H, q, J = 7.2 Hz), 7.80-7.85 (2H, m), 7.88 (2H, d, J = 8.6 Hz), 8.02 (2H, d, J = 8.6 Hz), 8.08 (2H, d, J = 8.6 Hz), 8.10-8.15 (1H, m), 8.20 (2H, d, J = 8.6 Hz), 8.80 (1H, s) |
| 73 | | (DMSO-d6) 1.25 (3H, t, J = 7.2 Hz), 1.30-1.40 (3H, m), 3.88 (2H, q, J = 7.2 Hz), 4.38 (2H, q, J = 7.2 Hz), 6.60-6.75 (4H, m), 7.65-7.75 (4H, m), 7.85-7.95 (3H, m), 8.87 (1H, s) |
| 74 | | (DMSO-d6) 1.35 (3H, t, J = 7.2 Hz), 4.37 (2H, q, J = 7.2 Hz), 5.18 (2H, s), 7.14 (2H, d, J = 8.3 Hz), 7.35-7.55 (5H, m), 7.65-7.80 (4H, m), 7.85-7.95 (3H, m), 8.19 (2H, d, J = 7.7 Hz), 8.74 (1H, s) |

TABLE 15

| Ex No. | Strc | (Solv) ¹H-NMR δ ppm: |
|---|---|---|
| 75 | | (DMSO-d6) 1.37 (3H, t, J = 7.2 Hz), 4.37 (2H, q, J = 7.2 Hz), 6.85-6.90 (2H, m), 7.60-7.70 (1H, m), 7.70-7.80 (2H, m), 7.85-7.95 (3H, m), 8.19 (2H, d, J = 8.3 Hz), 8.72 (1H, s) |

TABLE 15-continued

| Ex No. | Strc | (Solv) ¹H-NMR δ ppm: |
|---|---|---|
| 76 | | (DMSO-d6) 1.35 (3H, t, J = 7.2 Hz), 3.01 (3H, s), 4.37 (2H, q, J = 7.2 Hz), 7.30 (2H, d, J = 8.0 Hz). 7.65-7.80 (4H, m), 7.85-7.90 (2H, m), 7.95 (1H, d, J = 1.8 Hz), 8.15-8.25 (2H, m), 8.74 (1H, s) |
| 77 | | (CDCl3) 1.44 (3 H, t, J = 7.0 Hz), 4.45 (2 H, q, J = 7.0 Hz), 4.71 (2 H, d, J = 5.7 Hz), 6.53 (1 H, br. s.), 7.25-7.70 (8 H, m), 7.85-8.00 (2 H, m), 8.21 (1 H, s), 8.28 (2 H, d, J = 8.5 Hz) |
| 78 | | (CDCl3) 1.44 (3 H, t, J = 7.2 Hz), 2.80-3.20 (3 H, m), 4.44 (2 H, q, J = 7.2 Hz), 4.50-4.90 (2 H, m), 7.10-7.70 (9 H, m), 7.80-8.10 (2 H, m), 8.27 (2 H, d, J = 8.2 Hz) |
| 79 | | (CDCl3) 1.44 (3 H, t, J = 7.2 Hz), 3.43 (3 H, s), 3.62 (2 H, t, J = 5.0 Hz), 3.65-3.75 (2H, m), 4.45 (2 H, q, J = 7.2 Hz), 6.62 (1 H, br. s.), 7.50-7.65 (3 H, m), 7.85-7.95 (2 H, m), 8.20-8.25 (1 H, m), 8.28 (2 H, d, J = 8.5 Hz) |

TABLE 16
| Ex No. | Strc | (Solv) ¹H-NMR δ ppm: |
|---|---|---|
| 80 | 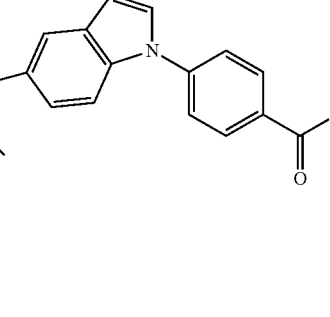 | (CDCl3) 1.44 (3 H, t, J = 7.1 Hz), 3.00-3.90 (10 H, m), 4.45 (2 H, q, J = 7.1 Hz), 7.48 (1 H, dd, J = 8.5, 1.6 Hz), 7.50-7.65 (3 H, m), 7.80-8.05 (2 H, m), 8.27 (2 H, d, J = 8.5 Hz) |
| 81 | 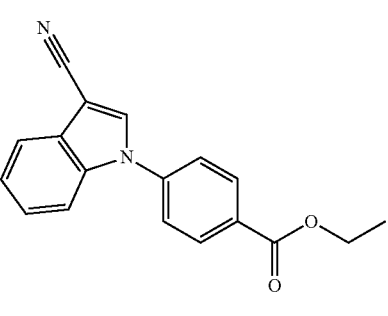 | (CDCl3) 1.44 (3 H, t, J = 7.2 Hz), 3.20-4.15 (8 H, m), 4.45 (2 H, q, J = 7.2 Hz), 7.47 (1 H, dd, J = 8.5, 1.6 Hz), 7.50-7.65 (3 H, m), 7.85-7.95 (2 H, m), 8.28 (2 H, d, J = 8.8 Hz) |
| 82 | 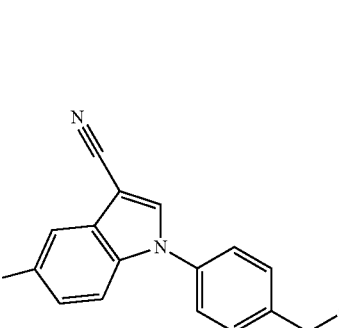 | (CDCl3) 1.44 (3 H, t, J = 7.1 Hz), 4.44 (2 H, q, J = 7.1 Hz), 5.17 (2 H, s), 7.07 (1 H, dd, J = 9.0, 2.5 Hz), 7.20 (1 H, dd, J = 4.7, 1.3 Hz), 7.25-7.45 (3 H, m), 7.46 (1 H, d, J = 9.0 Hz), 7.56 (2 H, d, J = 8.7 Hz), 7.79 (1 H, s), 8.25 (2 H, d, J = 8.7 Hz) |
| 83 | 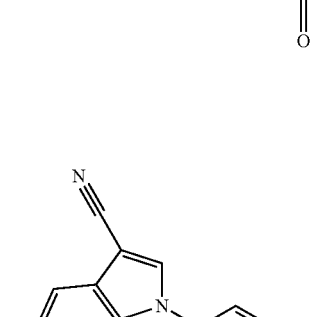 | (CDCl3) 1.44 (3 H, t, J = 7.1 Hz), 1.95-2.10 (2 H, m), 2.28 (6 H, s), 2.49 (2 H, t, J = 7.3 Hz), 4.05-4.20 (2 H, m), 4.44 (2 H, q, J = 7.1 Hz), 7.00 (1 H, dd, J = 9.1, 2.3 Hz), 7.24 (1 H, d, J = 2.3 Hz), 7.44 (1 H, d, J = 9.1 Hz), 7.56 (2 H, d, J = 8.7 Hz), 7.78 (1 H, s), 8.24 (2 H, d, J = 8.7 Hz) |

TABLE 16-continued

| Ex No. | Strc | (Solv) ¹H-NMR δ ppm: |
|---|---|---|
| 84 | | (CDCl3) 1.40-1.50 (12 H, m), 1.95-2.10 (2 H, m), 3.30-3.45 (2 H, m), 4.05-4.00 (2 H, m), 4.44 (2 H, q, J = 7.2 Hz), 4.77 (1 H, br. s.), 7.00 (1 H, dd, J = 8.9, 2.3 Hz), 7.22 (1 H, d, J = 2.3 Hz), 7.45 (1 H, d, J = 8.9 Hz), 7.56 (2 H, d, J = 8.5 Hz), 7.79 (1 H, s), 8.25 (2 H, d, J = 8.5 Hz) |
| 85 | | (DMSO-d6) 1.37 (3H, t, J = 7.1 Hz), 4.39 (2H, q, J = 7.1 Hz), 5.36 (2H, s), 7.05 (1H, d, J = 8.0 Hz), 7.25-7.45 (4H, m), 7.50-7.65 (2H, m), 8.02 (1H, d, J = 8.6 Hz), 8.1 (1H, d, J = 8.6 Hz), 8.5 (1H, dd, J = 8.6 Hz, 2.4 Hz), 8.95 (1H, s), 9.12 (1H, m) |

TABLE 17

| Ex No. | Strc | (Solv) ¹H-NMR δ ppm: |
|---|---|---|
| 86 | | (DMSO-d6) 1.30-1.45 (3H, m), 2.47 (3H, s), 4.30-4.45 (2H, m), 7.3 (1H, d, J = 8.7 Hz), 7.53 (1H, s), 8.00 (1H, d, J = 8.7 Hz), 8.44 (1H, d, J = 8.6 Hz), 8.45-8.55 (1H, m), 9.0 (1H, s), 9.05-9.15 (1H, m) |
| 87 | | (DMSO-d6) 1.36 (3H, t, J = 7.1 Hz), 2.97 (3H, s), 4.37 (2H, q, J = 7.1 Hz), 7.20-7.40 (1H, m), 7.59 (1H, d, J = 2.0 Hz), 7.70 (1H, d, J = 9.0 Hz), 7.75-7.90 (2H, m), 8.10-8.25 (2H, m), 8.70 (1H, s), 9.79 (1H, brs.) |

TABLE 17-continued

| Ex No. | Strc | (Solv) $^1$H-NMR δ ppm: |
|---|---|---|
| 88 | | (DMSO-d6) 1.35 (3H, t, J = 7.1 Hz), 2.94 (3H, s), 4.37 (2H, q, J = 7.1 Hz), 5.19 (2H, s), 7.05-8.25 (7H, m), 8.73 (1H, s) |
| 89 | | (DMSO-d6) 1.42 (3H, t, J = 7.1 Hz), 3.55 (3H, s), 4.40 (2H, q, J = 7.1 Hz), 5.31 (2H, s), 7.19 (1H, dd, J = 8.3 Hz, 2 Hz), 7.25-7.65 (4H, m), 7.80-8.05 (3H, m) |
| 90 | | (DMSO-d6) 2.47 (3H, s), 3.44 (3H, s), 3.86 (3H, s), 5.38 (2H, s), 7.20-7.30 (1H, m), 7.35-7.70 (4H, m), 7.90 (1 H, d, J = 8.4 Hz), 8.62 (1H, s) |
| 91 | | (DMSO-46) 2.44 (3H, s), 3.44 (3H, s), 3.86 (3H, s), 5.39 (2H, s), 7.20-7.30 (1H, m), 7.39 (1H, dd, J = 8.3 Hz, 2.0 Hz), 7.50 (1H, d, J = 2 0 Hz), 7.52 (1H, s), 7.65 (1H, d, J = 8.2 Hz), 7.90 (1H, d, J = 8.4 Hz), 8.59 (1H, s) |
| 92 | | (DMSO-d6) 1.33 (3H, t, J = 7.1 Hz), 3.44 (3H, s), 4.32 (2H, q, J = 7.1 Hz), 5.38 (2H, s), 7.20-7.65 (4H, m), 7.73 (1H, dd, J = 9.0 Hz, 4.1 Hz), 7.88 (1H, d, J = 8.3 Hz), 8.74 (1H, s) |

TABLE 18
| Ex No. | Strc | (Solv) ¹H-NMR δ ppm: |
|---|---|---|
| 93 | 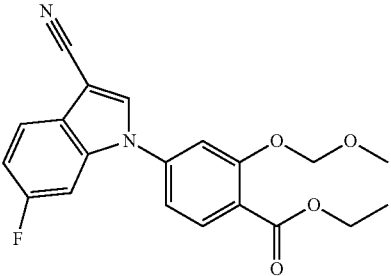 | (DMSO-d6) 1.33 (3H, t, J = 7.1 Hz), 3.44 (3H, s), 4.32 (2H, q, J = 7.1 Hz), 5.39 (2H, s), 7.20-7.65 (4H, m), 7.75-7.85 (1H, m), 7.88 (1H, d, J = 8.4 Hz), 8.7 (1H, s) |
| 94 | 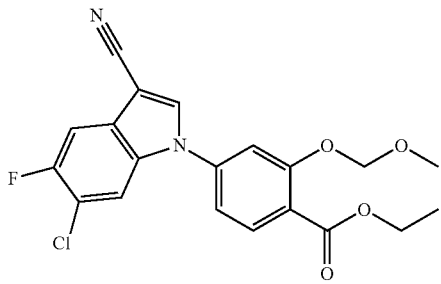 | (DMSO-d6) 1.33 (3H, t, J = 7.1 Hz), 3.44 (3H, s), 4.32 (2H, q, J = 7.1 Hz), 5.38 (2H, s), 7.41 (1H, dd, J = 8.3 Hz, 2 Hz), 7.50 (1H, d, J = 2.0 Hz), 7.80-7.95 (3H, m), 8.79 (1H, s) |
| 95 | 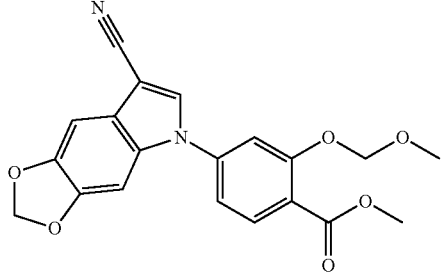 | (DMSO-d6) 3.43 (3H, s), 3.85 (3H, s), 5.39 (2H, s), 6.10 (2H, s), 7.21 (1H, s), 7.23 (1H, s), 7.30-7.50 (2H, m), 7.85-7.95 (1H, m), 8.45 (1H, s) |
| 96 | 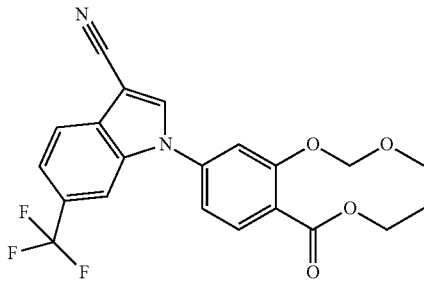 | (DMSO-d6) 1.33 (3H, t, J = 7.1 Hz), 3.44 (3H, s), 4.33 (2H, q, J = 7.1 Hz), 5.37 (2H, s), 7.40-7.50 (1H, m), 7.55-7.60 (1H, m), 7.65-7.80 (1H, m), 7.91 (1H, d, J = 8.3 Hz), 7.95-8.1 (2H, m), 8.92 (1H, s) |
| 97 | 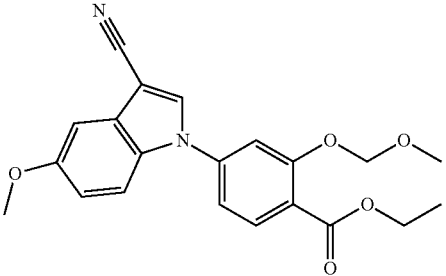 | (DMSO-d6) 1.32 (3H, t, J = 7.1 Hz), 3.44 (3H, s), 3.86 (3H, s), 4.32 (2H, q, J = 7.1 Hz), 5.38 (2H, s), 7.03 (1H, dd, J = 9.1 Hz, 2.4 Hz), 7.21 (1H, d, J = 2.4 Hz), 7.30-7.55 (2H, m), 7.63 (1H, d, J = 9.1 Hz), 7.87 (1H, d, J = 8.2 Hz), 8.62 (1H, s) |

TABLE 18-continued

| Ex No. | Strc | (Solv) ¹H-NMR δ ppm: |
|---|---|---|
| 98 | | (DMSO-d6) 1.32 (3H, t, J = 7.1 Hz), 3.44 (3H, s), 4.32 (2H, q, J = 7.1 Hz), 5.38 (2H, s), 7.4 (1H, dd, J = 8.3 Hz, 2.1 Hz), 7.44 (1H, dd, J = 8.9 Hz, 2.0 Hz), 7.5 (1H, d, J = 2.1 Hz), 7.73 (1H, d, J = 8.9 Hz), 7.83 (1H, d, J = 2 Hz), 7.88 (1H, d, J = 8.3 Hz), 8.76 (1H, s) |

TABLE 19

| Ex No. | Strc | (Solv) ¹H-NMR δ ppm: |
|---|---|---|
| 99 | | (DMSO-d6) 1.32 (3H, t, J = 7.1 Hz), 3.46 (3H, s), 4.32 (2H, q, J = 7.1 Hz), 5.40 (2H, s), 7.35-7.55 (5H, m), 7.70-7.85 (4H, m), 7.90 (1H, d, J = 8.3 Hz), 7.98 (1H, s), 8.72 (1H, s) |
| 100 | | (DMSO-d6) 1.32 (3H, t, J = 7.1 Hz), 3.45 (3H, s), 4.32 (2H, q, J = 7.1 Hz), 5.40 (2H, s), 7.35-7.50 (4H, m), 7.62 (1H, d, J = 2.0 Hz), 7.70-7.75 (3H, m), 7.85 (1H, d, J = 8.4 Hz), 7.90-7.95 (2H, m), 8.72 (1H, s), |
| 101 | | (DMSO-d6) 1.41 (3H, t, J = 7.2 Hz), 3.55 (3H, s), 4.41 (2H, q, J = 7.2 Hz), 5.15 (2H, s), 5.31 (2H, s), 7.08 (1H, dd, J = 9.1 Hz, 2.4 Hz), 7.16 (1H, dd, J = 8.3 Hz, 2.0 Hz), 7.30-7.55 (8H, m), 7.78 (1H, s); 7.97 (1H, d, J = 8.3 Hz) |
| 102 | | (DMSO-d6) 1.34 (3H, t, J = 7.1 Hz), 3.44 (3H, s), 4.31 (2H, q, J = 7.1 Hz), 5.30-5.40 (4H, m), 6.99 (1H, d, J = 7.5 Hz), 7.25-7.50 (7H, m), 7.59 (2H, d, J = 7.6 Hz), 7.86 (1H, d, J = 8.4 Hz), 8.58 (1 H, s) |

TABLE 19-continued

| Ex No. | Strc | (Solv) $^1$H-NMR δ ppm: |
|---|---|---|
| 103 | | (DMSO-d6) 1.33 (3H, t, J = 7.1 Hz), 3.44 (3H, s), 4.33 (2H, q, J = 7.1 Hz), 5.37 (2H, s), 7.41 (1H, dd, J = 8.3 Hz, 2.0 Hz), 7.52 (1H, d, J = 2.0 Hz), 7.79 (1H, dd, J = 8.7 Hz, 1.6 Hz), 7.80-7.87 (1H, m), 7.89 (1H, d, J = 8.3 Hz), 8.35-8.4 (1H, m), 8.88 (1H, s) |
| 104 | | (DMSO-d6) 1.33 (3H, t, J = 7.1 Hz), 3.44 (3H, s), 4.33 (2H, q, J = 7.1 Hz), 5.39 (2H, s), 7.40-7.60 (2H, m), 7.70-8.1 (3H, m), 8.24 (1H, s), 8.94 (1H, s) |

TABLE 20

| Ex No. | Strc | (Solv) $^1$H-NMR δ ppm: |
|---|---|---|
| 105 | | (DMSO-d6) 1.33 (3H, t, J = 7.1 Hz), 3.44 (3H, s), 4.33 (2H, q, J = 7.1 Hz), 5.37 (2H, s), 7.41 (1H, dd, J = 8.3 Hz, 2.0 Hz), 7.50-7.60 (2H, m), 7.85-7.95 (2H, m), 8.0-8.05 (1H, m), 8.94 (1H, s) |
| 106 | | (DMSO-d6) 1.33 (3H, t, J = 7.1 Hz), 3.44 (3H, s), 4.32 (2H, q, J = 7.1 Hz), 5.38 (2H, s), 7.15-7.60 (5H, m), 7.88 (1H, d, J = 8.3 Hz), 8.73 (1H, s) |
| 107 | | (DMSO-d6) 1.20-1.35 (9H, m), 3.00-3.10 (1H, m), 3.45 (3H, s), 4.32 (2H, q, J = 7.1 Hz), 5.39 (2H, s), 6.80-7.95 (6H, m), 8.62 (1H, s) |

TABLE 20-continued

| Ex No. | Strc | (Solv) ¹H-NMR δ ppm: |
|---|---|---|
| 108 | | (DMSO-d6) 1.32 (3H, t, J = 7.1 Hz), 3.44 (3H, s), 4.31 (2H, q, J = 7.1 Hz), 6.89 (1H, dd, J = 9.0 Hz, 2.4 Hz), 7.01 (1H, d, J = 2.4 Hz), 7.36 (1H, dd, J = 8.3 Hz, 2.0 Hz), 7.45 (1H, d, J = 2.0 Hz), 7.55 (1H, d, J = 9.0 Hz), 7.86 (1H, d, J = 8.3 Hz), 8.53 (1H, s), 9.54 (1H, brs.) |
| 109 | | (DMSO-d6) 1.32 (3H, t, J = 7.1 Hz), 3.45 (3H, s), 4.32 (2H, q, J = 7.1 Hz), 5.38 (2H, s), 6.70 (1H, d, J = 8.0 Hz), 7.07 (1H, d, J = 8.0 Hz), 7.23 (1H, t, J = 8.0 Hz), 7.40 (1H, dd, J = 8.3 Hz, 2.0 Hz), 7.52 (1H, d, J = 2.0 Hz), 7.89 (1H, d, J = 8.3 Hz), 8.72 (1H, s), 9.82 (1H, s) |
| 110 | | (DMSO-d6) 1.09 (6H, d, J = 6.4 Hz), 1.34 (3H, t, J = 7.1 Hz), 2.00-2.20 (1H, m), 3.44 (3H, s), 3.95 (2H, d, J = 5.5 Hz), 4.31 (2H, q, J = 7.1 Hz), 5.37 (2H, s), 6.83 (1H, d, J = 7.4 Hz), 7.20-7.40 (3H, m), 7.46 (1H, s), 7.86 (1H, d, J = 8.2 Hz), 8.53 (1H, s) |

TABLE 21

| Ex No. | Strc | (Solv) ¹H-NMR δ ppm: |
|---|---|---|
| 111 | | (DMSO-d6) 1.01 (6H, d, J = 6.6 Hz), 1.32 (3H, t, J = 7.1 Hz), 2.00-2.15 (1H, m), 3.44 (3H, s), 3.85 (2H, d, J = 6.6 Hz), 4.32 (2H, q, J = 7.1 Hz), 5.38 (2H, s), 7.30 (1H, dd, J = 9.1 Hz, 2.4 Hz), 7.19 (1H, d, J = 2.4 Hz), 7.37 (1H, dd, J = 8.3 Hz, 2.0 Hz), 7.47 (1H, d, J = 2.0 Hz), 7.62 (1H, d, J = 9.1 Hz), 7.87 (1H, d, J = 8.3 Hz), 8.59 (1H, s) |
| 112 | | (DMSO-d6) 1.25-1.40 (9H, m), 3.44 (3H, s), 4.32 (2H, q, J = 7.1 Hz), 4.65-4.80 (1H, m), 5.38 (2H, s), 7.00 (1H, dd, J = 9.0 Hz, 2.3 Hz), 7.19 (1H, d, J = 2.3 Hz), 7.37 (1H, dd, J = 8.3 Hz, 2.0 Hz), 7.47 (1H, d, J = 2.0 Hz), 7.61 (1H, d, J = 9.0 Hz), 7.87 (1H, d, J = 8.3 Hz), 8.59 (1H, s) |

TABLE 21-continued

| Ex No. | Strc | (Solv) ¹H-NMR δ ppm: |
|---|---|---|
| 113 | | (DMSO-d6) 1.32 (3H, t, J = 7.1 Hz), 2.06 (3H, s), 3.44 (3H, s), 4.25-4.45 (6H, m), 5.38 (2H, s), 7.05 (1H, dd, J = 9.1 Hz, 2.4 Hz), 7.25 (1H, d, J = 2.4 Hz), 7.38 (1H, dd, J = 8.4 Hz, 2.0 Hz), 7.47 (1H, d, J = 2.0 Hz), 7.64 (1H, d, J = 9.1 Hz), 7.87 (1H, d, J = 8.4 Hz), 8.61 (1H, s) |
| 114 | | (DMSO-d6) 1.32 (3H, t, J = 7.1 Hz), 3.33 (3H, s), 3.44 (3H, s), 3.65-3.8 (2H, m), 4.15-4.25 (2H, m), 4.32 (2H, q, J = 7.1 Hz), 5.38 (2H, s), 6.95-7.10 (1H, m), 7.15-7.25 (1H, m), 7.30-7.5 (2H, m), 7.63 (1, d, J = 9.1 Hz), 7.87 (1H, d, J = 8.2 Hz), 8.60 (1H, s) |
| 115 | | (CDCl3) 1.41 (3H, t, J = 7.1 Hz), 3.55 (3H, s), 3.84 (3H, s), 4.41 (2H, q, J = 7.1 Hz), 4.74 (2H, s), 5.30 (2H, s), 7.05-7.25 (3H, m), 7.33 (1H, d, J = 1.9 Hz), 7.49 (1H, d, J = 8.9 Hz), 7.79 (1H, s), 7.97 (1H, d, J = 8.2 Hz) |
| 116 | | (CDCl3) 1.41 (3H, t, J = 7.3 Hz), 1.47 (3H, t, J = 6.9 Hz), 3.55 (3H, s), 4.13 (2H, q, J = 6.9 Hz), 4.41 (2H, q, J = 7.3 Hz), 5.31 (2H, s), 7.00 (1H, dd, J = 9.0, 2.5 Hz), 7.16 (1H, dd, J = 8.4, 2.1 Hz), 7.21 (1H, d, J = 2.5 Hz), 7.34 (1H, d, J = 2.1 Hz), 7.46 (1H, d, J = 9.0 Hz), 7.77 (1H, s), 7.97 (1H, d, J = 8.41 Hz) |

TABLE 22

| Ex No. | Strc | (Solv) ¹H-NMR δ ppm: |
|---|---|---|
| 117 | | (CDCl3) 1.42 (3H, t, J = 7.2 Hz), 3.45 (3H, s), 3.55 (3H, s), 3.70-3.85 (2H, m), 4.05-4.20 (2H, m), 4.41 (2H, q, J = 7.2 Hz), 5.31 (2H, s), 7.05 (1H, dd, J = 8.8, 1.9 Hz), 7.08 (1H, d, J = 1.9 Hz), 7.15 (1H, dd, J = 8.3, 1.8 Hz), 7.35 (1H, d, J = 1.8 Hz), 7.68 (1H, d, J = 8.8 Hz), 7.73 (1H, s), 7.98 (1H, d, J = 8.3 Hz) |
| 118 | | (CDCl3) 1.42 (3H, t, J = 7.1 Hz), 3.56 (3H, s), 3.80 (3H, s), 4.42 (2H, q, J = 7.1 Hz), 4.66 (2H, s), 5.33 (2H, s), 7.06 (1H, dd, J = 8.8, 2.2 Hz), 7.08 (1H, d, J = 2.2 Hz), 7.13 (1H, dd, J = 8.3, 1.8 Hz), 7.35 (1H, d, J = 1.8 Hz), 7.72 (1H, d, J = 8.8 Hz), 7.75 (1H, s), 7.98 (1H, d, J = 8.3 Hz) |
| 119 | | (CDCl3) 1.42 (3H, t, J = 7.1 Hz), 2.09 (3H, s), 3.55 (3H, s), 4.17 (2H, t, J = 4.7 Hz), 4.35-4.50 (4H, m), 5.32 (2H, s), 6.95-7.10 (2H, m), 7.15 (1H, dd, J = 8.2, 1.3 Hz), 7.35 (1H, d, J = 1.3 Hz), 7.70 (1H, d, J = 8.5 Hz), 7.74 (1H, s), 7.98 (1H, d, J = 8.2 Hz) |
| 120 | | (CDCl3) 1.23 (3H, t, J = 7.0 Hz), 1.42 (3H, t, J = 7.2 Hz), 3.56 (3H, s), 3.60 (2H, q, J = 7.0 Hz), 3.75-3.85 (2H, m), 4.05-4.20 (2H, m), 4.41 (2H, q, J = 7.2 Hz), 5.31 (2H, s), 7.04 (1H, dd, J = 8.8, 2.1 Hz), 7.08 (1H, d, J = 2.1 Hz), 7.15 (1H, dd, J = 8.3, 2.2 Hz), 7.35 (1H, d, J = 2.2 Hz), 7.68 (1H, d, J = 8.8 Hz), 7.72 (1H, s), 7.97 (1H, d, J = 8.3 Hz) |

TABLE 22-continued

| Ex No. | Strc | (Solv) ¹H-NMR δ ppm: |
| --- | --- | --- |
| 121 | | (CDCl3) 1.04 (3H, t, J = 7.4 Hz), 1.42 (3H, t, J = 7.0 Hz), 1.70-1.95 (2H, m), 3.55 (3H, s), 3.91 (2H, t, J = 6.6 Hz), 4.41 (2H, q, J = 7.0 Hz), 5.31 (2H, s), 7.01 (1H, dd, J = 8.5, 1.9 Hz), 7.03 (1H, d, J = 1.9 Hz), 7.16 (1H, dd, J = 8.4, 1.8 Hz), 7.37 (1H, d, J = 1.8 Hz), 7.67 (1H, d, J = 8.5 Hz), 7.71 (1H, s), 7.98 (1H, d, J = 8.4 Hz) |

TABLE 23

| Ex No. | Strc | (Solv) ¹H-NMR δ ppm: |
| --- | --- | --- |
| 122 | | (CDCl3) 0.98 (3H, t, J = 7.4 Hz), 1.42 (3H, t, J = 7.1 Hz), 1.45-1.60 (2H, m), 1.70-1.85 (2H, m), 3.55 (3H, s), 3.95 (2H, t, J = 6.5 Hz), 4.41 (2H, q, J = 7.1 Hz), 5.31 (2H, s) 6.95-7.10 (2H, m), 7.16 (1H, dd, J = 8.1, 1.5 Hz), 7.37 (1H, d, J = 1.5 Hz), 7.67 (1H, d, J = 8.8 Hz), 7.71 (1H, s), 7.98 (1H, d, J = 8.1 Hz) |
| 123 | | (CDCl3) 1.42 (3H, t, J = 7.2 Hz), 3.54 (3H, s), 4.25-4.40 (4H, m), 4.41 (2H, q, J = 7.2 Hz), 5.31 (2H, s), 6.85-7.05 (3H, m), 7.06 (1H, dd, J = 8.8, 2.1 Hz), 7.12 (1H, d, J = 2.1 Hz), 7.15 (1H, dd, J = 8.4, 1.9 Hz), 7.29 (2H, t, J = 8.0 Hz), 7.37 (1H, d, J = 1.9 Hz), 7.70 (1H, d, J = 8.8 Hz), 7.74 (1H, s), 7.98 (1H, d, J = 8.4 Hz) |
| 124 | | (DMSO-d6) 1.25-1.40 (6H, m), 3.44 (3H, s), 4.06 (2H, q, J = 7.0 Hz), 4.32 (2H, q, J = 7.1 Hz), 5.39 (2H, s), 7.00 (1H, dd, J = 8.8 Hz, 2.1 Hz), 7.16 (1H, d, J = 2.1 Hz), 7.39 (1H, dd, J = 8.4 Hz, 2.0 Hz), 7.52 (1H, d, J = 2.0 Hz), 7.63 (1H, d, J = 8.8 Hz), 7.88 (1H, d, J = 8.4 Hz), 8.53 (1H, s) |

TABLE 23-continued
| Ex No. | Strc | (Solv) $^1$H-NMR δ ppm: |
|---|---|---|
| 125 | 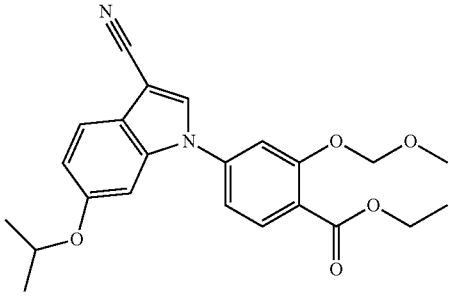 [SMILES: CCOC(=O)c1ccc(-n2cc(C#N)c3ccc(OC(C)C)cc32)cc1OCOC] | (DMSO-d6) 1.27 (6H, d, J = 6.0 Hz), 1.33 (3H, t, J = 7.1 Hz), 3.44 (3H, s), 4.32 (2H, q, J = 7.1 Hz), 4.55-4.75 (1H, m), 5.38 (2H, s), 6.95-7.05 (1H, m), 7.10-7.20 (1H, m), 7.30-7.40 (1H, m), 7.45-7.55 (1H, m), 7.62 (1H, d, J = 8.8 Hz), 7.89 (1H, d, J = 8.3 Hz), 8.52 (1H, s) |
| 126 | 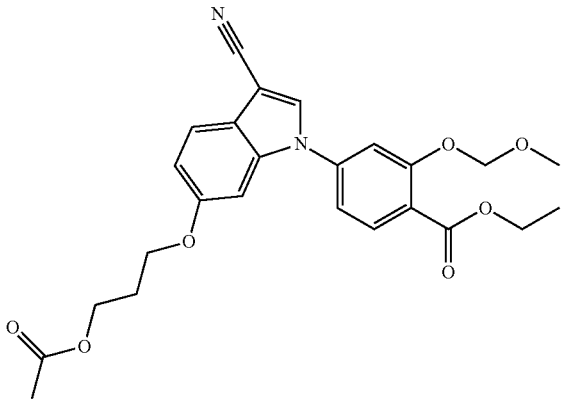 [SMILES: CCOC(=O)c1ccc(-n2cc(C#N)c3ccc(OCCCOC(C)=O)cc32)cc1OCOC] | (DMSO-d6) 1.31 (3H, t, J = 7.1 Hz), 1.95-2.10 (5H, m), 3.44 (3H, s), 4.05-4.20 (4H, m), 4.31 (2H, q, J = 7.1 Hz), 5.39 (2H, s), 7.01 (1H, dd, J = 8.6 Hz, 2.1 Hz), 7.17 (1H, d, J = 2.1 Hz), 7.38 (1H, dd, J = 8.6 Hz, 1.9 Hz), 7.52 (1H, d, J = 1.9 Hz), 7.63 (1H, d, J = 8.6 Hz), 7.87 (1H, d, J = 8.6 Hz), 8.3 (1H, s) |
TABLE 24
| Ex No. | Strc | (Solv) $^1$H-NMR δ ppm: |
|---|---|---|
| 127 | 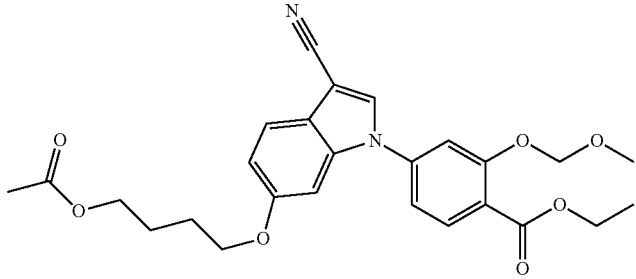 [SMILES: CCOC(=O)c1ccc(-n2cc(C#N)c3ccc(OCCCCOC(C)=O)cc32)cc1OCOC] | (DMSO-d6) 1.34 (3H, t, J = 7.2 Hz), 1.60-1.85 (4H, m), 2.00 (3H, s), 3.44 (3H, s), 4.00-4.10 (4H, m), 4.31 (2H, q, J = 7.2 Hz), 5.39 (2H, s), 7.00 (1H, dd, J = 8.6 Hz, 1.8 Hz), 7.16 (1H, d, J = 1.8 Hz), 7.38 (1H, dd, J = 8.6 Hz, 1.8 Hz), 7.51 (1H, d, J = 1.8 Hz), 7.62 (1H, d, J = 8.6 Hz), 7.87 (1H, d, J = 8.6 Hz), 8.52 (1H, s) |
| 128 | 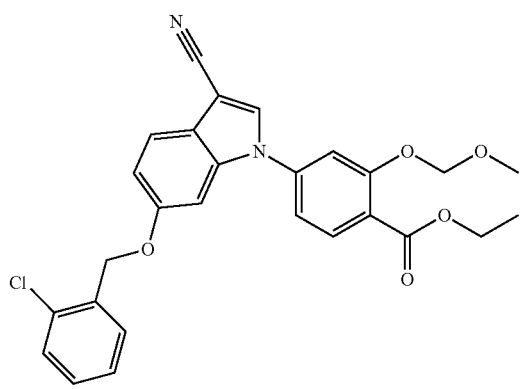 [SMILES: CCOC(=O)c1ccc(-n2cc(C#N)c3ccc(OCc4ccccc4Cl)cc32)cc1OCOC] | (DMSO-d6) 1.34 (3H, t, J = 7.1 Hz), 3.43 (3H, s), 4.31 (2H, q, J = 7.1 Hz), 5.21 (2H, s), 5.38, (2H, s), 7.05-7.15, (1H, m), 7.25-7.70 (8H, m), 7.87 (1H, d, J = 8.6 Hz), 8.55 (1H, s) |

TABLE 24-continued

| Ex No. | Strc | (Solv) ¹H-NMR δ ppm: |
|---|---|---|
| 129 | | (DMSO-d6) 1.31 (3H, t, J = 7.1 Hz), 3.44 (3H, s), 4.32 (2H, q, J = 7.1 Hz), 5.18 (2H, s), 5.38 (2H, s), 7.11 (1H, dd, J = 8.6 Hz, 1.8 Hz), 7.28 (1H, d, J = 1.8 Hz), 7.33 (1H, dd, J = 8.6 Hz, 1.8 Hz), 7.35-7.45 (3H, m), 7.49 (1H, d, J = 1.8 Hz), 7.50-7.55 (1H, m), 7.66 (1H, d, J = 8.6 Hz), 7.87 (1H, d, J = 8.6 Hz), 8.54 (1H, s) |
| 130 | | (DMSO-d6) 1.32 (3H, t, J = 7.1 Hz), 3.44 (3H, s), 4.32 (2H, q, J = 7.1 Hz), 5.15 (2H, s), 5.38 (2H, s), 7.09 (1H, dd, J = 8.7 Hz, 2.2 Hz), 7.28 (1H, d, J = 2.2 Hz), 7.35 (1H, dd, J = 8.3 Hz, 1.9 Hz), 7.40-7.50 (5H, m), 7.65 (1H, d, J = 8.7 Hz), 7.87 (1H, d, J = 8.3 Hz), 8.54 (1H, s) |
| 131 | | (DMSO-d6) 0.25-0.35 (2H, m), 0.50-0.60 (2H, m), 1.10-1.30 (1H, m), 1.31 (3H, t, J = 7.1 Hz), 3.44 (3H, s), 3.84 (2H, d, J = 7.6 Hz), 4.31 (2H, q, J = 7.1 Hz), 5.38 (2H, s), 7.01 (1H, dd, J = 8.8 Hz, 1.8 Hz), 7.14 (1H, d, J = 1.8 Hz), 7.37 (1H, dd, J = 8.6 Hz, 1.8 Hz), 7.51 (1H, d, J = 1.8 Hz), 7.61 (1H, d, J = 8.6 Hz), 7.87 (1H, d, J = 8.6 Hz), 8.51 (1H, s) |

TABLE 25

| Ex No. | Strc | (Solv) ¹H-NMR δ ppm: |
|---|---|---|
| 132 | | (DMSO-d6) 1.31 (3H, t, J = 7.1 Hz), 1.75-1.95 (4H, m), 2.00-2.15 (2H, m), 2.65-2.80 (1H, m), 3.45 (3H, s), 3.97 (2H, d, J = 6.8 Hz), 4.31 (2H, d, J = 6.8 Hz), 5.40 (2H, s), 7.00 (1H, dd, J = 8.3 Hz, 2.0 Hz), 7.17 (1H, d, J = 2.0 Hz), 7.38 (1H, d, J = 8.3 Hz), 7.53 (1H, d, J = 2.0 Hz), 7,61 (1H, d, J = 8.6 Hz), 7.87 (1H, d, J = 8.6 Hz), 8.52 (1H, s) |
| 133 | | (CDCl3) 1.42 (3H, t, J = 7.1 Hz), 2.34 (6H, s), 2.74 (2H, t, J = 5.6 Hz), 3.55 (3H, s), 4.5 (2H, t, J = 5.6 Hz), 4.42 (2H, q, J = 7.1 Hz), 5.32 (2H, s), 7.00-7.10 (2H, m), 7.16 (1H, dd, J = 8.3, 2.0 Hz), 7.36 (1H, d, J = 2.0 Hz), 7.68 (1H, d, J = 8.7 Hz), 7.72 (1H, s), 7.98 (1H, d, J = 8.3 Hz) |
| 134 | | (DMSO-d6) 0.92 (6H, d, J = 6.8 Hz), 1.31 (3H, t, J = 7.0 Hz), 1.62 (2H, q, J = 6.8 Hz), 1.70-1.85 (1H, m), 3.44 (3H, s), 4.01 (2H, t, J = 6.6 Hz), 4.31 (2H, q, J = 7.0 Hz), 5.39 (2H, s), 7.00 (1H, d, J = 8.7 Hz, 2.2 Hz), 7.18 (1H, d, J = 2.2 Hz), 7.38 (1H, dd, J = 8.3 Hz, 1.9 Hz), 7.53 (1H, d, J = 1.9 Hz), 7.62 (1H, d, J = 8.7 Hz), 7.87 (1H, d, J = 8.3 Hz), 8.53 (1H, s) |
| 135 | | (CDCl3) 1.42 (3H, t, J = 7.2 Hz), 1.90-2.05 (2H, m), 2.23 (6H, s), 2.44 (2H, t, J = 7.3 Hz), 3.55 (3H, s), 4.01 (2H, t, J = 6.5 Hz), 4.41 (2H, q, J = 7.2 Hz), 5.31 (2H, s), 7.00 (1H, dd, J = 8.8, 2.1 Hz), 7.04 (1H, d, J = 2.1 Hz), 7.15 (1H, dd, J = 8.4, 2.1 Hz), 7.36 (1H, d, J = 2.1 Hz), 7.67 (1H, d, J = 8.8 Hz), 7.71 (1H, s), 7.98 (1H, d, J = 8.4 Hz) |

TABLE 25-continued

| Ex No. | Strc | (Solv) $^1$H-NMR δ ppm: |
|---|---|---|
| 136 | 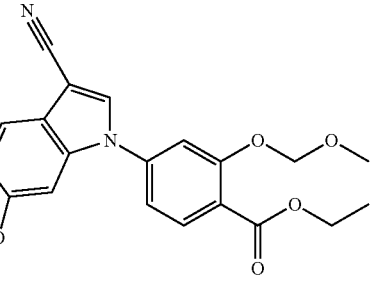 | (DMSO-d6) 1.35-1.50 (12H, m), 1.90-2.05 (2H, m), 3.25-3.40 (2H, m), 3.55 (3H, s), 4.01 (2H, t, J = 6.0 Hz), 4.41 (2H, q, J = 7.2 Hz), 4.73 (1H, br. s.), 5.32 (2H, s), 7.00 (1H, dd, J = 8.7, 2.1 Hz) 7.04 (1H, d, J = 2.1 Hz) 7.15 (1H, dd, J = 8.3, 2.0 Hz) 7.36 (1H, d, J = 2.0 Hz) 7.68 (1H, d, J = 8.7 Hz) 7.72 (1H, s) 7.98 (1H, d, J = 8.3 Hz) |

TABLE 26

| Ex No. | Strc | (Solv) $^1$H-NMR δ ppm: |
|---|---|---|
| 137 | 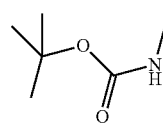 | (CDCl3) 1.30-1.55 (3H, m), 1.80-2.05 (2H, m), 2.80-3.05 (2H, m), 3.55 (3H, s), 3.95-4.15 (2H, m), 4.30-4.50 (2H, m), 5.32 (2H, s), 6.90-7.25 (3H, m), 7.30-7.45 (1H, m), 7.60-7.80 (2H, m), 7.90-8.10 (1H, m) |
| 138 | 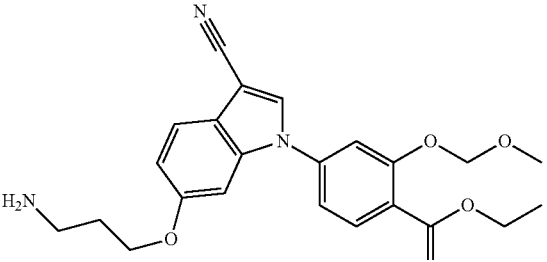 | (CDCl3) 1.42 (3H, t, J = 7.1 Hz), 3.02 (3H, s), 3.50-3.65 (5H, m), 4.11 (2H, t, J = 4.9 Hz), 4.42 (2H, q, J = 7.1 Hz), 4.77 (1H, br. s.), 5.32 (2H, s), 6.99 (1H, dd, J = 8.7, 2.1 Hz), 7.04 (1H, d, J = 2.1 Hz), 7.15 (1H, dd, J = 8.3, 2.1 Hz), 7.35 (1H, d, J = 2.1 Hz), 7.71 (1H, d, J = 8.7 Hz), 7.75 (1H, s), 7.99 (1H, d, J = 8.3 Hz) |
| 139 | 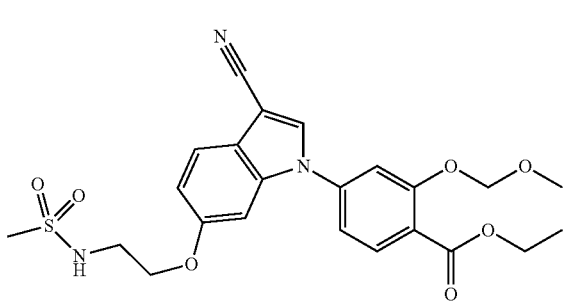 | (CDCl3) 1.42 (3H, t, J = 7.2 Hz), 1.98 (3H, s), 2.00-2.10 (2H, m), 3.46 (2H, q, J = 6.6 Hz), 3.55 (3H, s), 4.03 (2H, t, J = 5.8 Hz), 4.42 (2H, q, J = 7.2 Hz), 5.32 (2H, s), 5.74 (1H, br. s.), 6.99 (1H, dd, J = 8.6, 2.0 Hz), 7.03 (1H, d, J = 2.0 Hz), 7.15 (1H, dd, J = 8.2, 1.9 Hz), 7.36 (1H, d, J = 1.9 Hz), 7.69 (1H, d, J = 8.6 Hz), 7.73 (1H, s), 7.99 (1H, d, J = 8.2 Hz) |

TABLE 26-continued

| Ex No. | Strc | (Solv) ¹H-NMR δ ppm: |
|---|---|---|
| 140 | | (CDCl3) 1.42 (3H, t, J = 7.1 Hz), 2.00-2.15 (2H, m), 2.98 (3H, s), 3.39 (2H, q, J = 6.3 Hz), 3.55 (3H, s), 4.09 (2H, t, J = 5.8 Hz), 4.41 (2H, q, J = 7.1 Hz), 4,52 (1H, br. s.), 5.32 (2H, s), 6.99 (1H, dd, J = 8.6, 2.1 Hz), 7.04 (1H, d, J = 2.1 Hz), 7.16 (1H, dd, J = 8.2, 2.1 Hz), 7.36 (1H, d, J = 2.1 Hz), 7.69 (1H, d, J = 8.6 Hz), 7.74 (1H, s), 7.99 (1H, d, J = 8.2 Hz) |
| 141 | | (DMSO-d6) 5.37 (2H, s), 7.05 (1H, d, J = 7.9 Hz), 7.30-7.50 (5H, m), 8.45-8.55 (1H, m), 8.93 (1H, s), 9.05-9.15 (1H, m) |

TABLE 27

| Ex No. | Strc | ¹H-NMR δ ppm (DMSO-d6): |
|---|---|---|
| 142 | | 7.35-7.50 (2H, m), 7.54-8.85 (3H, m), 7.94 (1H, d, J = 2.2 Hz), 8.04 (1H, d, J = 8.3 Hz), 8.72 (1H, s), 13.50-14 (1H, brs.) |
| 143 | | 2.47 (3H, s), 7.25-7.35 (1H, m), 7.54 (1H, s), 8.45 (1H, d, J = 8.6 Hz), 8.48 (1H, dd, J = 8.3 Hz, 2.2 Hz), 9.01 (1H, s), 9.09 (1H, d, J = 2.2 Hz), 13.00-14.00 (1H, brs.) |
| 144 | | 3.33 (3H, s), 7.10-8.15 (8H, m), 13.30 (1H, brs.) |

TABLE 27-continued

| Ex No. | Strc | $^1$H-NMR δ ppm (DMSO-d6): |
|---|---|---|
| 145 | | 7.35-7.45 (3H, m), 7.75-8.05 (4H, m), 8.55-8.65 (1H, m), 13.62 (1H, brs.) |
| 146 | | 7.40-7.46 (2H, m), 7.66-7.67 (1H, m), 7.76-7.78 (3H, m), 8.10 (1H, t, J = 8.2 Hz), 8.72 (1H, s) |
| 147 | | 2.47 (3H, s), 3.44 (3H, s), 5.37 (2H, s), 7.20-7.45 (3H, m), 7.56 (1H, m), 7.60-7.65 (1H, m), 7.88 (1H, d, J = 8.3 Hz) |
| 148 | | 3.92 (3H, s), 7.25-7.50 (4H, m), 7.70-7.90 (3H, m), 8.70 (1H, s), 12.4 (1H, s-br) |
| 149 | | 2.33 (3H, s), 5.26 (2H, s), 7.25-7.60 (7H, m), 7.70-7.85 (2H, m), 8.10-8.25 (2H, m), 8.54 (1H, s), 13.25 (1H, brs.) |

TABLE 28

| Ex No. | Strc | $^1$H-NMR δ ppm (DMSO-d6): |
|---|---|---|
| 150 | | 7.30-7.95 (10H, m), 8.10-8.25 (2H, m), 8.74 (1H, s), 13.27 (1H, brs.) |
| 151 | | 5.23 (2H, s), 7.11 (1H, dd, J = 9.1 Hz, 2.4 Hz), 7.25-7.55 (5H, m), 7.63 (1H, d, 9.1 Hz), 7.75-7.90 (2H, m), 8.10-8.2 (2H, m), 8.63 (1H, s), |
| 152 | | 6.85-7.10 (2H, m), 7.45-7.90 (3H, m), 8.10-8.25 (2H, m), 8.55 (1H, s), 9.45-9.70 (1H, brs.) |
| 153 | | 3.65-3.75 (2H, m), 4.15-4.25 (2H, m), 7.04 (1H, dd, J = 9.1 Hz, 2.4 Hz), 7.22 (1H, d, J = 2.3 Hz), 7.62 (1H, d, J = 9.1 Hz), 7.75-7.85 (2H, m), 8.10-8.20 (2H, m), 8.64 (1H, s), 13.00-13.50 (1H, brs.) |
| 154 | | 4.30-4.55 (4H, m), 6.90-7.05 (3H, m), 7.07 (1H, dd, J = 9.1 Hz, 2.4 Hz), 7.25-7.40 (3H, m), 7.63 (1H, d, J = 9.1 Hz), 7.75-7.85 (2H, m), 8.10-8.20 (2H, m), 8.65 (1H, s), 13.10-13.40 (1H, brs.) |

TABLE 28-continued
| Ex No. | Strc | ¹H-NMR δ ppm (DMSO-d6): |
|---|---|---|
| 155 | 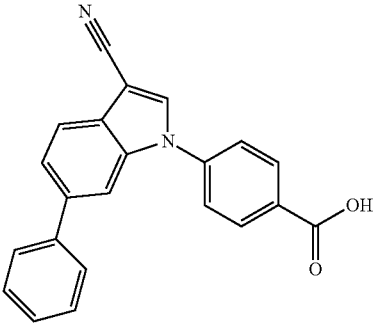 [SMILES: N#Cc1cn(-c2ccc(C(=O)O)cc2)c2cc(-c3ccccc3)ccc12] | 7.30-7.95.(10H, m), 8.10-8.25 (2H, m), 8.74 (1H, s), 13.32 (1H, brs.) |
| 156 | 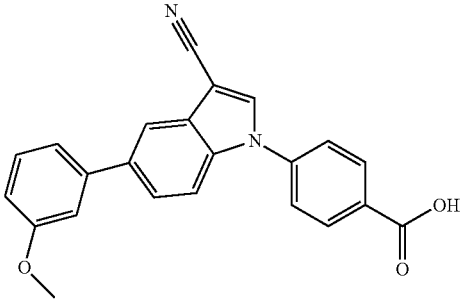 [SMILES: COc1cccc(-c2ccc3c(c2)c(C#N)cn3-c2ccc(C(=O)O)cc2)c1] | 3.86 (3H, s), 6.85-8.25 (11H, m), 8.74 (1H, s) |
TABLE 29
| Ex No. | Strc | ¹H-NMR δ ppm (DMSO-d6): |
|---|---|---|
| 157 | 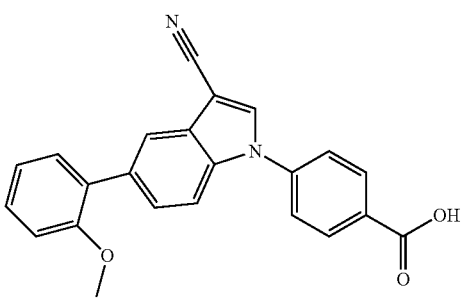 [SMILES: COc1ccccc1-c1ccc2c(c1)c(C#N)cn2-c1ccc(C(=O)O)cc1] | 3.79 (3H, s), 6.90-7.90 (9H, m), 8.10-8.25 (2H, m), 8.73 (1H, s) |
| 158 | 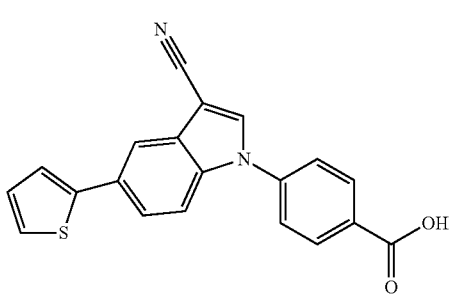 [SMILES: N#Cc1cn(-c2ccc(C(=O)O)cc2)c2ccc(-c3cccs3)cc12] | 7.10-7.25 (1H, m), 7.50-8.25 (9H, m), 8.73 (1H, s), 13.24 (1H, brs.) |

TABLE 29-continued
| Ex No. | Strc | $^1$H-NMR δ ppm (DMSO-d6): |
|---|---|---|
| 159 | 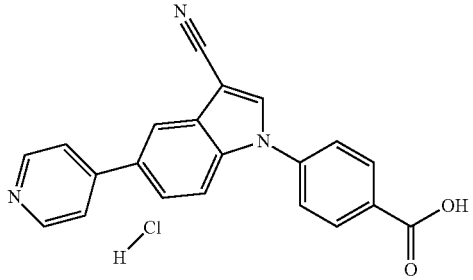 | 7.75-8.45 (10H, m), 8.75-8.90 (3H, m), 13.34 (1H, brs.) |
| 160 | 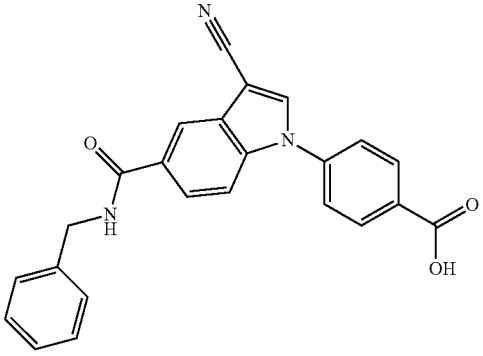 [SMILES: N#Cc1cn(-c2ccc(C(=O)O)cc2)c2ccc(C(=O)NCc3ccccc3)cc12] | 4.45-4.6 (2H, m), 7.70-7.5 (5H, m), 7.65-8.05 (4H, m), 8.10-8.25 (2H, m), 8.35-8.5 (1H, m), 8.79 (1H, s), 9.15-9.3 (1H, m), 13.3 (1H, brs.) |
| 161 | 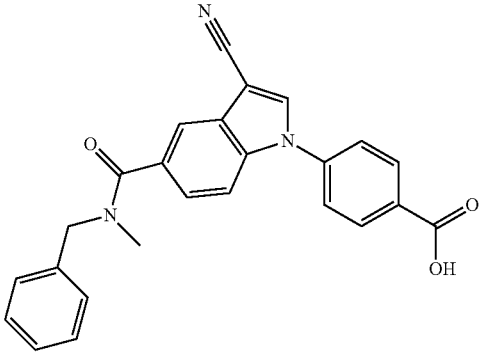 [SMILES: CN(Cc1ccccc1)C(=O)c1ccc2c(c1)c(C#N)cn2-c1ccc(C(=O)O)cc1] | 2.91 (3H, brs.), 4.40-4.85 (2H, m), 7.00-7.6 (6H, m), 7.65-8.0 (4H, m), 8.05-8.3 (2H, m), 8.78 (1H, brs.), 13.2 (1H, brs.) |
| 162 | 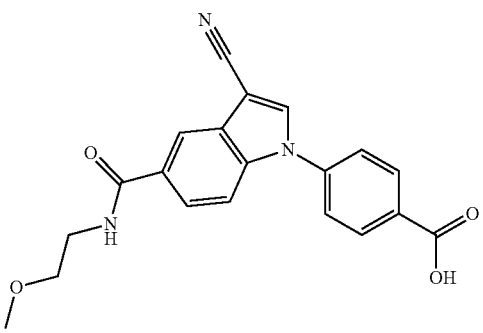 [SMILES: COCCNC(=O)c1ccc2c(c1)c(C#N)cn2-c1ccc(C(=O)O)cc1] | 3.40-3.6 (4H, m), 7.70-8.0 (4H, m), 8.10-8.25 (2H, m), 8.30-8.45 (1H, m), 8.65-8.85 (2H, m), 13.3 (1H, brs.) |

TABLE 29-continued

| Ex No. | Strc | ¹H-NMR δ ppm (DMSO-d6): |
|---|---|---|
| 163 | | 3.00 (3H, s), 7.40-8.00 (5H, m), 8.17 (2H, d, J = 8.4 Hz), 8.77 (1H, s), 13.2 (1H, brs.) |

TABLE 30

| Ex No. | Strc | ¹H-NMR δ ppm (DMSO-d6): |
|---|---|---|
| 164 | | 3.00-4.0 (8H, m), 7.40-7.55 (1H, m), 7.80-8.0 (4H, m), 8.05-8.30 (2H, m), 8.70-8.85 (1H, m), 13.3 (1H, brs.) |
| 165 | | 2.96 (6H, s), 6.83 (2H, d, J = 8.1 Hz), 7.6 (2H, d, J = 8.1 Hz), 7.65 (1H, d, J = 8.1 Hz), 7.73 (1H, d, J = 8.1 Hz), 7.80-7.85 (3H, m), 8.17 (2H, d, J = 8.1 Hz), 8.70 (1H, s), 13.2 (1H, s-br) |
| 166 | | 2.63 (3H, s), 7.80-7.90 (4H, m), 7.95 (2H, d, J = 8.5 Hz), 8.06 (2H, d, J = 8.5 Hz), 8.11 (1H, s), 8.18 (2H, d, J = 8.5 Hz), 8.78 (1H, s) |

TABLE 30-continued

| Ex No. | Strc | ¹H-NMR δ ppm (DMSO-d6): |
|---|---|---|
| 167 | | 3.28 (3H, s), 7.80-7.85 (4H, m), 8.02 (2H, d, J = 8.5 Hz), 8.08 (2H, d, J = 8.5 Hz), 8.13 (1H, s), 8.17 (2H, d, J = 8.7 Hz), 8.79 (1H, s) |
| 168 | | 1.23 (3H, t, J = 7.6 Hz), 2.66 (2H, q, 7.6 Hz), 7.25-7.40 (2H, m), 7.65-8.25 (9H, m), 8.73 (1H, s), 13.29 (1H, brs.) |
| 169 | | 1.36 (3H, t, J = 6.5 Hz), 4.08 (2H, q, J = 6.5 Hz), 7.05-7.85 (8H, m), 7.90-8.70 (4H, m), 13.2 (1H, brs.) |
| 170 | | 4.77 (2H, s), 6.95-7.25 (2H, m), 7.50-7.90 (3H, m), 8.00-8.25 (2H, m), 8.63 (1H, brs.), 12.50-14.0 (2H, m) |

TABLE 31

| Ex No. | Strc | ¹H-NMR δ ppm (DMSO-d6): |
|---|---|---|
| 171 | | 3.70-3.8 (2H, m), 4.09 (2H, t, J = 4.8 Hz), 4.80-4.95 (1H, m), 7.04 (1H, dd, J = 9.1 Hz, 2.5 Hz), 7.21 (1H, d, J = 2.5 Hz), 7.61 (1H, d, J = 9.1 Hz), 7.78 (2H, d, J = 8.3 Hz), 8.15 (2H, d, J = 8.3 Hz), 8.62 (1H, s), 13.2 (1H, brs.) |

TABLE 31-continued

| Ex No. | Strc | $^1$H-NMR δ ppm (DMSO-d6): |
|---|---|---|
| 172 | | 1.80-2.00 (2H, m), 3.50-3.70 (2H, m), 4.00-4.25 (2H, m), 4.40-4.7 (1H, m), 6.95-7.10 (1H, m), 7.15-7.25 (1H, m), 7.50-7.65 (1H, m), 7.70-7.85 (2H, m), 8.05-8.25 (2H, m), 8.61 (1H, s), 13.30 (1H, brs.) |
| 173 | | 5.18 (2H, s), 7.00-7.95 (14H, m), 8.10-8.25 (2H, m), 8.71 (1H, s) |
| 174 | | 1.05-1.25 (3H, m), 3.45-3.85 (4H, m), 4.10-4.25 (2H, m), 6.95-7.35 (2H, m), 7.50-7.95 (3H, m), 8.00-8.30 (2H, m), 8.50-8.75 (1H, m) 13.2 (1H, brs.) |
| 175 | | 3.70-3.95 (2H, m), 4.15-4.40 (2H, m), 4.58 (2H, s), 8.95-7.45 (7H, m), 7.50-7.90 (3H, m), 8.05-8.25 (2H, m), 8.62 (1H, s), 13.2 (1H, brs.) |
| 176 | | 5.21 (2H, s), 7.09 (1H, dd, J = 8.8 Hz, 1.6 Hz), 7.22 (1H, d, J = 4.8 Hz), 7.32 (1H, d, J = 1.6 Hz), 7.50-7.70 (5H, m), 7.79 (1H, d, J = 8.2 Hz), 8.15 (1H, d, J = 8.2 Hz), 8.64 (1H, s), 13.2 (1H, brs.) |

TABLE 31-continued
| Ex No. | Strc | ¹H-NMR δ ppm (DMSO-d6): |
|---|---|---|
| 177 | 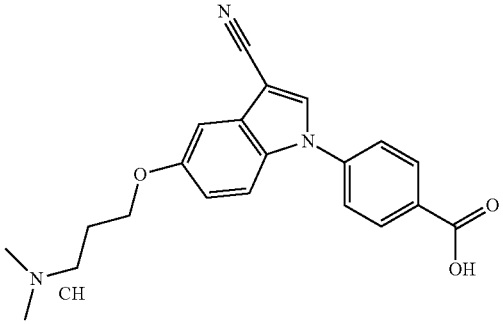 | 2.10-2.25 (2H, m), 2.81 (6H, s), 3.15-3.40 (2H, m), 4.17 (2H, t, J = 6.1 Hz), 7.04 (1H, dd, J = 9.1 Hz, 2.4 Hz), 7.24 (1H, d, J = 2.4 Hz), 7.64 (1H, d, J = 9.1 Hz), 7.75-7.85 (2H, m), 8.10-8.20 (2H, m), 8.65 (1H, s), 9.88 (1H, brs.), 13.2 (1H, brs.) |
TABLE 32
| Ex No. | Strc | ¹H-NMR δ ppm (DMSO-d6): |
|---|---|---|
| 178 | 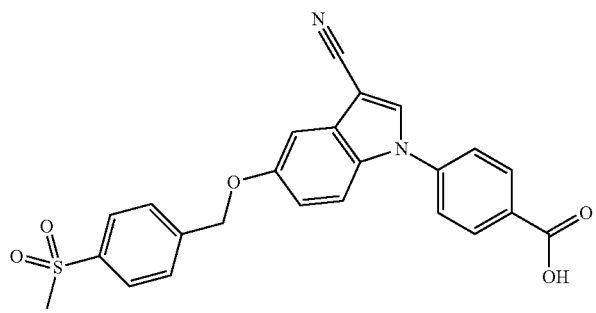 [SMILES: CS(=O)(=O)c1ccc(COc2ccc3c(c2)c(C#N)cn3-c2ccc(C(=O)O)cc2)cc1] | 3.23 (3H, s), 5.38 (2H, s), 7.00-7.45 (2H, m), 7.50-7.45 (2H, m), 7.50-8.40 (9H, m), 8.65 (1H, s), 13.20 (1H, brs.) |
| 179 | 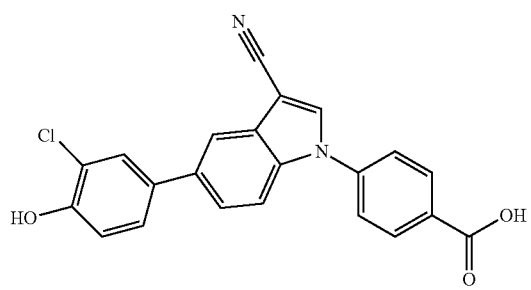 [SMILES: N#Cc1cn(-c2ccc(C(=O)O)cc2)c2ccc(-c3ccc(O)c(Cl)c3)cc12] | 7.00-7.15 (1H, m), 7.55-8.00 (7H, m), 8.10-8.25 (2H, m), 8.73 (1H, s), 10.32 (1H, s), 13.29 (1H, brs.) |
| 180 | 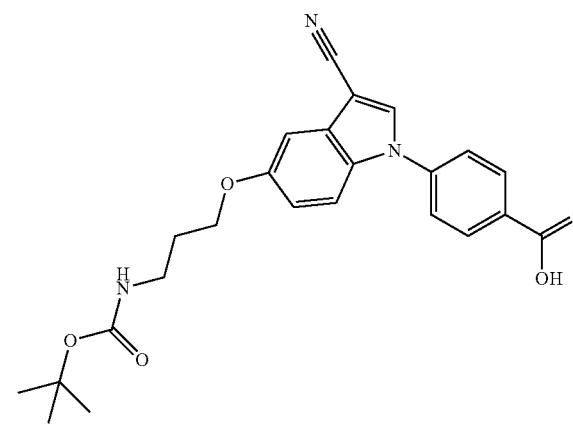 | 1.38 (9H, s), 1.80-1.95 (2H, m), 3.05-3.20 (2H, m), 4.00-4.15 (2H, m), 6.85-7.10 (2H, m), 7.15-7.25 (1H, m), 7.61 (1H, d, J = 9.2 Hz), 7.79 (2H, d, J = 8.0 Hz), 8.15 (2H, d, J = 8.0 Hz), 8.62 (1H, s), 13.2 (1H, brs.) |

TABLE 32-continued

| Ex No. | Strc | $^1$H-NMR δ ppm (DMSO-d6): |
|---|---|---|
| 181 | | 1.95-2.15 (2H, m), 2.90-3.10 (2H, m), 4.10-4.25 (2H, m), 6.95-7.10 (1H, m) 7.15-7.30 (1H, m), 7.63 (1H, d, J = 9.2 Hz), 7.79 (2H, d, J = 8.0 Hz), 7.84 (2H, brs.), 8.16 (2H, d, J = 8.0 Hz), 8.64 (1H, s), 13.2 (1H, brs.) |
| 182 | | 2.98 (3H, s), 7.03 (1H, dd, J = 9.0 Hz, 1.9 Hz), 7.59 (1H, d, J = 1.9 Hz), 7.70 (1H, d, J = 9.0 Hz), 7.75-7.85 (2H, m), 8.10-8.20 (2H, m), 8.69 (1H, s), 9.78 (1H, s), 13.0-13.5 (1H, brs.) |
| 183 | | 3.03 (3H, s), 7.32 (2H, d, J = 8.1 Hz), 7.69 (1H, dd, J = 7.3, 1.5 Hz), 7.75 (2H, d, J = 8.1 Hz), 7.78 (1H, s), 7.83 (2H, d, J = 8.5 Hz), 7.95 (1H, d, J = 2.0 Hz), 8.17 (2H, d, J = 8.9 Hz), 8.72 (1H, s) 13.2 (1H, s-br) |
| 184 | | 4.62 (2H, d, J = 5.3 Hz), 5.26 (1H, t, J = 5.3 Hz), 7.25-7.85 (5H, m), 8.10-8.25 (2H, m), 8.64 (1H, s), 13.25 (1H, brs.) |

TABLE 33

| Ex No. | Strc | $^1$H-NMR δ ppm (DMSO-d6): |
|---|---|---|
| 185 | | 3.30 (3H, s), 3.60-3.70 (2H, m), 4.10-4.20 (2H, m), 7.03 (1H, dd, J = 8.7, 1.7 Hz), 7.15 (1H, d, J =1.7 Hz), 7.64 (1H, d, J = 8.7 Hz), 7.80 (2H, d, J = 8.7 Hz), 8.15 (2H, d, J = 8.7 Hz), 8.55 (1H, s) |

TABLE 33-continued

| Ex No. | Strc | ¹H-NMR δ ppm (DMSO-d6): |
|---|---|---|
| 186 | | 3.65-3.80 (2H, m), 4.03 (2H, t, J = 6.0 Hz), 4.80-4.95 (1H, m), 6.95-7.20 (2H, m), 7.60-7.90 (3H, m), 8.10-8.25 (2H, m), 8.55 (1H, s), 13.28 (1H, brs.) |
| 187 | | 2.47 (3H, s), 2.68 (3H, s), 7.30-7.45 (2H, m), 7.55 (1H, s), 8.33 (1H, d, J = 8.6 Hz), 8.89 (1H, s), 13.62 (1H, brs.) |
| 188 | | 7.20-7.50 (4H m), 7.70-7.80 (2H, m), 8.01 (1H, d, J = 8.5 Hz), 8.69 (1H, s) |
| 189 | | 2.46 (3H, S), 7.15-7.35 (3H, m), 7.55 (1H, s), 7.63 (1H, d, J = 8.4 Hz), 7.90-8.10 (1H, m), 8.55-8.70 (1H, m) |
| 190 | | 7.15-7.50 (3H, m), 7.35-7.50 (1H, m), 7.65-7.85 (2H, m), 8.01 (1H, d, J = 8.3 Hz), 8.72 (1H, s) |

TABLE 33-continued

| Ex No. | Strc | $^1$H-NMR δ ppm (DMSO-d6): |
|---|---|---|
| 191 | | 7.15-7.35 (3H, m), 7.58 (1H, dd, J = 8.8 Hz, 2.5 Hz), 7.74 (1H, dd, J = 8.8 Hz, 4.4 Hz), 8.01 (1H, d, J = 8.4 Hz), 8.74 (1H, s) |

TABLE 34

| Ex No. | Strc | $^1$H-NMR δ ppm (DMSO-d6): |
|---|---|---|
| 192 | | 7.20-7.35 (3H, m), 7.54 (1H, dd, J = 9.9 Hz, 2.2 Hz), 7.79 (1H, dd, J = 8.8 Hz, 5.2 Hz), 8.01 (1H, d, J = 8.7 Hz), 8.70 (1H, s) |
| 193 | | 7.20-7.35 (2H, m), 7.86 (1H, d, J = 9.1 Hz), 7.90 (1H, d, J = 9.1 Hz), 8.01 (1H, d, J = 8.7 Hz), 8.79 (1H, s) |
| 194 | | 6.10 (2H, s), 7.15-7.25 (4H, m), 7.90-8.05 (1H, m), 8.45 (1H, s) |
| 195 | | 7.10-7.35 (2H, m), 7.65-7.75 (1H, m), 7.92 (1H, s), 7.95-8.10 (2H, m), 8.89 (1H, s) |

TABLE 34-continued

| Ex No. | Strc | ¹H-NMR δ ppm (DMSO-d6): |
|---|---|---|
| 196 | | 3.86 (3H, s), 7.03 (1H, dd, J = 9.0 Hz, 2.5 Hz), 7.15-7.30 (3H, m), 7.54 (1H, d, J = 9.0 Hz), 8.00 (1H, d, J = 8.3 Hz), 8.60 (1H, s) |
| 197 | | 7.15-7.35 (3H, m), 7.44 (1H, dd, J = 9.0 Hz, 2.2 Hz), 7.73 (1H, d, J = 9.0 Hz), 7.81 (1H, d, J = 2.2 Hz), 8.01 (1H, d, J = 8.4 Hz), 8.75 (1H, s) |
| 198 | | 7.25-7.40 (3H, m), 7.50 (2H, t, J = 7.6 Hz), 7.70-7.85 (4H, m), 7.97 (1H, s), 8.01 (1H, d, J = 9.8 Hz), 8.73 (1H, s) |

TABLE 35

| Ex No. | Strc | ¹H-NMR δ ppm (DMSO-d6): |
|---|---|---|
| 199 | | 7.25-7.55 (5H, m), 7.65-8.05 (6H, m), 8.72 (1H, s) |

TABLE 35-continued
| Ex No. | Strc | ¹H-NMR δ ppm (DMSO-d6): |
|---|---|---|
| 200 | 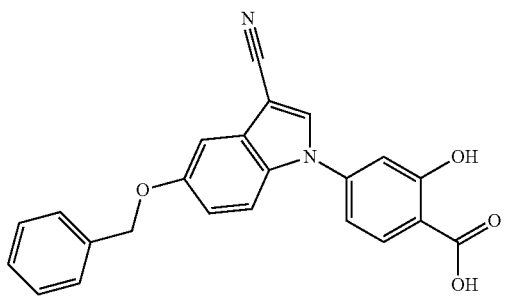 [SMILES: N#Cc1cn(-c2ccc(C(=O)O)c(O)c2)c2ccc(OCc3ccccc3)cc12] | 5.22 (2H, s), 7.00-7.60 (9H, m), 7.53 (1H, d, J = 9.0 Hz), 7.96 (1H, 8.4 Hz), 8.59 (1H, s) |
| 201 | 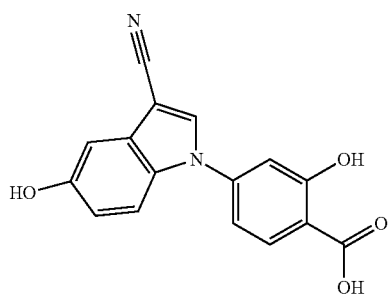 [SMILES: N#Cc1cn(-c2ccc(C(=O)O)c(O)c2)c2ccc(O)cc12] | 6.90 (1H, dd, J = 9.0 Hz, 2.3 Hz), 7.00 (1H, d, J = 2.1 Hz), 7.15-7.30 (2H, m), 7.56 (1H, d, 9.0 Hz), 7.98 (1H, d, J = 8.5 Hz), 8.55 (1H, s), 9.58 (1H, brs) |
| 202 | 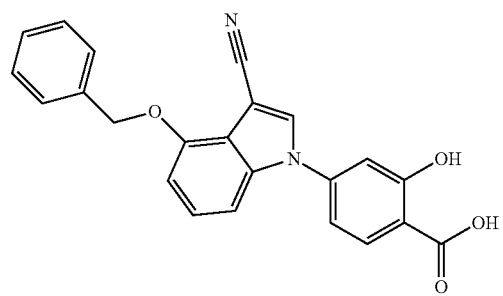 [SMILES: N#Cc1cn(-c2ccc(C(=O)O)c(O)c2)c2cccc(OCc3ccccc3)c12] | 5.35 (2H, s), 6.70-6.85 (2H, m), 6.94 (1H, d, J = 8.3 Hz), 7.20 (1H, d, J = 8.8 Hz), 7.26-7.34 (2H, m), 7.35-7.45 (2H, m), 7.59 (2H, d, J = 8.3 Hz), 7.81 (1H, d, J = 7.9 Hz), 8.47 (1H, s) |
| 203 | 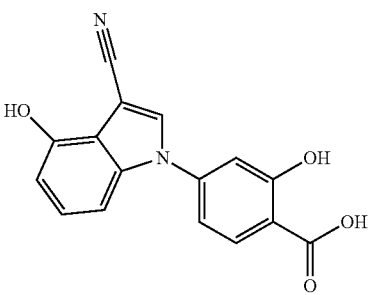 [SMILES: N#Cc1cn(-c2ccc(C(=O)O)c(O)c2)c2cccc(O)c12] | 6.69 (1H, d, J = 7.6 Hz), 7.11 (1H, d, J = 8.8 Hz), 7.15-7.25 (3H, m), 7.98 (1H, d, J = 8.8 Hz), 8.49 (1H, s). 10.3 (1H, s) |
| 204 | 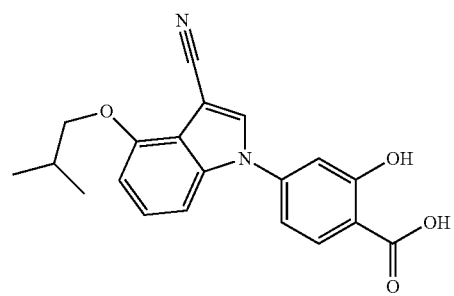 [SMILES: CC(C)COc1cccc2c1c(C#N)cn2-c1ccc(C(=O)O)c(O)c1] | 1.09 (6H, d, J = 6.3 Hz), 2.10-2.15 (1H, m), 3.90 (2H, d, J = 5.8 Hz), 6.83 (1H, d, J = 8.1 Hz), 7.19-7.29 (4H, m), 7.98 (1H, d, J = 8.5 Hz), 8.53 (1H, s) |

TABLE 35-continued

| Ex No. | Strc | $^1$H-NMR δ ppm (DMSO-d6): |
|---|---|---|
| 205 | | 1.01 (6H, d, J = 6.6 Hz), 2.00-2.15 (1H, m), 3.85 (2H d, J = 6.4 Hz), 7.03 (1H, dd, J = 9.1 Hz, 2.4 Hz), 7.15-7.30 (3H, m), 7.63 (1H, d, J = 9.1 Hz), 7.99 (1H, d, J = 3.3 Hz), 8.59 (1H, s) |

TABLE 36

| Ex No. | Strc | $^1$H-NMR δ ppm (DMSO-d6): |
|---|---|---|
| 206 | | 7.20-7.35 (2H, m), 7.75-7.90 (2H, m), 8.02 (1H, d, J = 8.4 Hz), 8.36 (1H, s), 8.88 (1H, s) |
| 207 | | 7.25-7.40 (2H, m), 7.70-7.80 (1H, m), 7.96 (1H, d, J = 8.3 Hz), 8.02 (1H, d, J = 8.3 Hz), 8.25 (1 H, s), 8.94 (1H, s) |
| 208 | | 7.25 (1H, dd, J = 8.5 Hz, 2.1 Hz), 7.31 (1H, d, J = 2.1 Hz), 7.50-7.60 (1H, m), 7.85-8.00 (1H, m), 7.95-8.10 (2H, m), 8.94 (1H, s) |
| 209 | | 1.30 (6H, d, J = 6.0 Hz), 4.65-4.80 (1H, m), 7.00 (1H, dd, J = 9.1 Hz, 2.3 Hz), 7.10-7.30 (3H, m), 7.61 (1H, d, J = 9.1 Hz), 7.99 (1H, d, J = 8.2 Hz), 8.59 (1H, s) |

TABLE 36-continued

| Ex No. | Strc | ¹H-NMR δ ppm (DMSO-d6): |
|---|---|---|
| 210 | | 3.75 (2H, t, J = 4.8 Hz), 4.09 (2H, d, J = 4.8 Hz), 4.50-5.25 (1H, br.), 7.04 (1H, dd, J = 9.1 Hz, 2.2 Hz), 7.15-7.30 (3H, m), 7.63 (1H, d, J = 9.1 Hz), 7.99 (1H, d, J = 8.2 Hz), 8.60 (1H, s) |
| 211 | | 3.34 (3H, s), 3.65-3.75 (2H, m), 4.15-4.25 (2H, m), 7.04 (1H, dd, J = 9.2 Hz, 2.5 Hz), 7.15-7.30 (3H, m), 7.63 (1H, d, J = 9.2 Hz), 7.99 (1H, d, J = 8.2 Hz), 8.60 (1H, s) |
| 212 | | 6.87 (1H, dd, J = 6.8, 2.1 Hz), 7.05 (1H, d, J = 2.1 Hz), 7.18-7.21 (2H, m), 7.52 (1H, d, J = 8.4 Hz), 7.98 (1H, d, J = 8.1 Hz), 8.44 (1H, s), 9.67 (1H, s) |

TABLE 37

| Ex No. | Strc | ¹H-NMR δ ppm (DMSO-d6): |
|---|---|---|
| 213 | | 4.80 (2H, s), 6.90-7.45 (4H, m), 7.50-7.75 (1H, m), 7.80-8.10 (1H, m), 8.62 (1H, s), 13.0 (1H, brs.) |

TABLE 37-continued
| Ex No. | Strc | $^1$H-NMR δ ppm (DMSO-d6): |
|---|---|---|
| 214 | 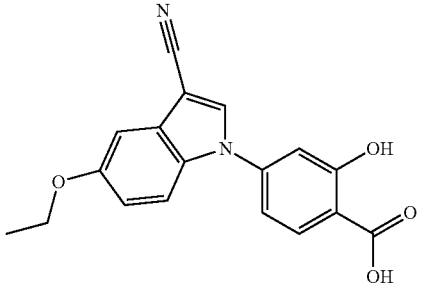 [SMILES: CCOc1ccc2c(c1)c(C#N)cn2-c1ccc(C(=O)O)c(O)c1] | 1.20-1.55 (3H, m), 4.00-4.25 (2H, m), 6.80-7.40 (4H, m), 7.50-7.70 (1H, m), 7.80-8.10 (1H, m), 8.40-8.70 (1H, m) |
| 215 | 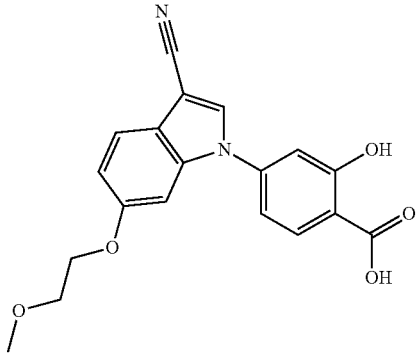 [SMILES: COCCOc1ccc2c(C#N)cn(-c3ccc(C(=O)O)c(O)c3)c2c1] | 3.30 (3H, s), 3.60-3.75 (2H, m), 4.00-4.25 (2H, m), 6.90-7.4 (4H, m), 7.50-7.7 (1H, m), 7.90-8.10 (1H, m), 8.52 (1H, s) |
| 216 | 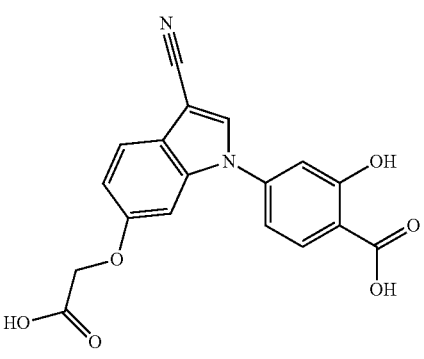 [SMILES: N#Cc1cn(-c2ccc(C(=O)O)c(O)c2)c2cc(OCC(=O)O)ccc12] | 4.75 (2H, s), 6.95-7.40 (4H, m), 7.65 (1H, d, J = 8.3 Hz), 7.90-8.05 (1H, m), 8.54 (1H, s), 13.0 (1H, brs.) |
| 217 | 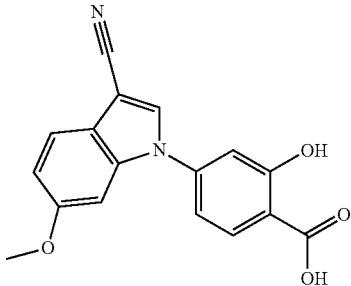 [SMILES: COc1ccc2c(C#N)cn(-c3ccc(C(=O)O)c(O)c3)c2c1] | 3.81 (3H, s), 7.03 (1H, dd, J = 8.8 Hz, 2.1 Hz), 7.05-7.35 (3H, m), 7.64 (1H, d, J = 8.8 Hz), 8.01 (1H, d, J = 8.9 Hz), 8.52 (1H, s) |

TABLE 37-continued
| Ex No. | Strc | $^1$H-NMR δ ppm (DMSO-d6): |
|---|---|---|
| 218 | 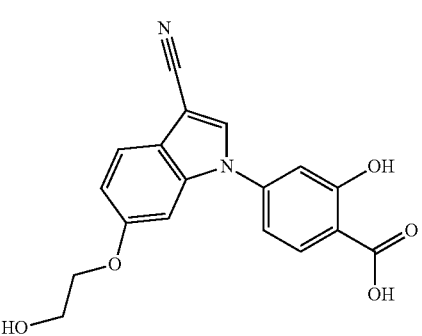 [SMILES: N#Cc1cn(-c2ccc(C(=O)O)c(O)c2)c2cc(OCCO)ccc12] | 3.65-3.80 (2H, m), 3.95-4.15 (2H, m), 6.95-7.40 (4H, m), 7.63 (1H, d, J = 8.2 Hz), 7.90-8.10 (1H, m), 8.52 (1H, s) |
TABLE 38
| Ex No. | Strc | $^1$H-NMR δ ppm (DMSO-d6): |
|---|---|---|
| 219 | 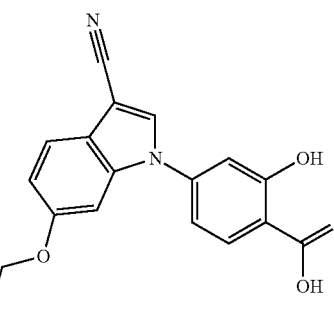 | 1.11 (3H, t, J = 7.0 Hz), 3.5 (2H, q, J = 7.0 Hz), 3.60-3.8 (2H, m), 4.05-4.20 (2H, m), 6.95-7.35 (4H, m), 7.63 (1H, d, J = 8.7 Hz), 7.90-8.10 (1H, m), 8.52 (1H, s) |
| 220 | 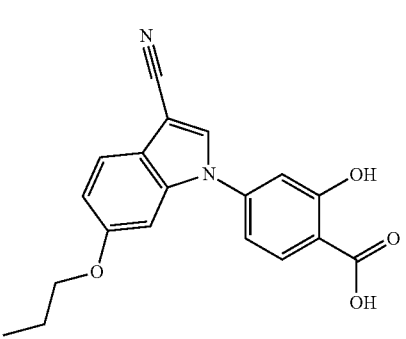 [SMILES: CCCOc1ccc2c(C#N)cn(-c3ccc(C(=O)O)c(O)c3)c2c1] | 0.98 (3H, t, J = 7.3 Hz), 1.65-1.85 (2H, m), 3.96 (2H, t, J = 6.5 Hz), 7.03 (1H, dd, J = 8.7 Hz, 2.0 Hz), 7.10-7.15 (1H, m), 7.20-7.35 (2H, m), 7.62 (1H, d, J = 8.7 Hz), 7.90-8.10 (1H, m), 8.51 (1H, s) |
| 221 | 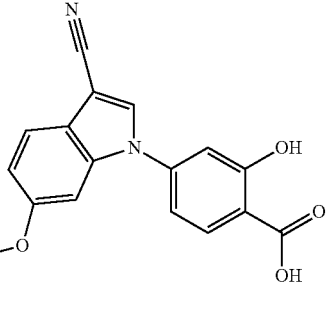 | 10.93 (3H, t, J = 7.4 Hz), 1.35-1.55 (2H, m), 1.60-1.8 (2H, m), 4.0 (2H, t, J = 6.4 Hz), 7.02 (1H, dd, J = 8.8 Hz, 2.0 Hz), 7.13 (1H, d, J = 2.0 Hz), 7.15-7.30 (2H, m), 7.62 (1H, d, J = 8.8 Hz), 7.95-8.05 (1H, m), 8.51 (1H, s) |

TABLE 38-continued

| Ex No. | Strc | ¹H-NMR δ ppm (DMSO-d6): |
|---|---|---|
| 222 | | 4.25-4.45 (4H, m), 6.80-7.05 (3H, m), 7.08 (1H, dd, J = 8.8 Hz, 2.0 Hz), 7.15-7.45 (5H, m), 7.65 (1H, d, J = 8.8 Hz), 8.0 (1H, d, J = 9.1 Hz), 8.53 (1H, s) |
| 223 | | 1.34 (3H, t, J = 7.0 Hz), 4.06 (2H, q, J = 7.0 Hz), 7.02 (1H, dd, J = 8.7 Hz, 2.1 Hz), 7.13 (1H, d, J = 2.1 Hz), 7.20-7.30 (2H, m), 7.62 (1H, d, J = 8.7 Hz), 8.00 (1H, d, J = 9.0 Hz), 8.51 (1H, s) |
| 224 | | 1.30 (6H, d, J = 6.0 Hz), 4.55-4.70 (1H, m), 7.02 (1H, dd, J = 8.7 Hz, 2.1 Hz), 7.12 (1H, d, J = 2.1 Hz), 7.20-7.30 (2H, m), 7.62 (1H, d, J = 8.7 Hz), 7.95-8.05 (1H, m), 8.51 (1H, s), |

TABLE 39

| Ex No. | Strc | ¹H-NMR δ ppm (DMSO-d6): |
|---|---|---|
| 225 | | 7.10-7.5 (4H, m), 7.54 (1H, d, J = 8.4 Hz), 8.01 (1H, d, J = 8.4 Hz), 8.74 (1H, s) |

TABLE 39-continued
| Ex No. | Strc | ¹H-NMR δ ppm (DMSO-d6): |
|---|---|---|
| 226 | 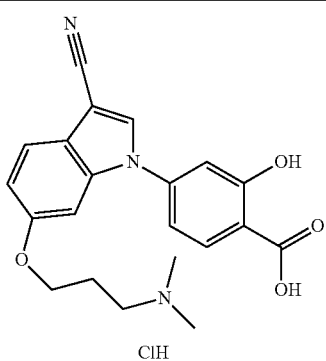 ClH | 2.05-2.20 (2H, m), 2.79 (3H, s), 2.80 (3H, s), 3.00-3.5 (2H, m), 4.10 (2H, t, J = 6.0 Hz), 7.05 (1H, dd, J = 8.7 Hz, 2.0 Hz), 7.16 (1H, d, J = 2.0 Hz), 7.20-7.30 (2H, m), 7.67 (1H, d, J = 8.7 Hz), 8.0 (1H, d, J = 8.3 Hz), 8.53 (1H, s), 9.67 (1H, brs.) |
| 227 | 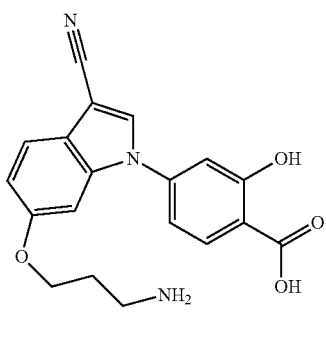 ClH | 2.00-2.10 (2H, m), 2.90-3.05 (2H, m), 4.12 (2H, t, J = 6.1 Hz), 7.06 (1H, dd, J = 8.7 Hz, 2.1 Hz), 7.17 (1H, d, J = 2.1 Hz), 7.20-7.30 (2H, m), 7.66 (1H, d, J = 8.7 Hz), 7.90-8.10 (4H, m), 8.54 (1H, s) |
| 228 | 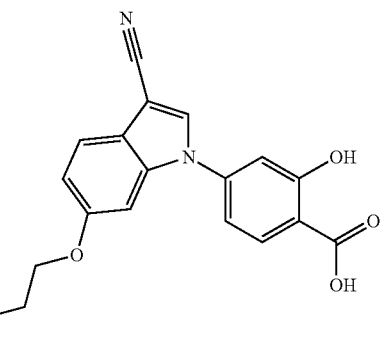 | 1.85-1.88 (2H, m), 3.54-3.57 (2H, m), 4.05-4.08 (2H, m), 7.02 (1H, dd, J = 6.2, 1.9 Hz), 7.14 (1H, s), 7.23-7.25 (2H, m), 7.62 (1H, d, J = 8.6 Hz), 8.00 (1H, d, J = 8.6 Hz), 8.51 (1H, s) |
| 229 | 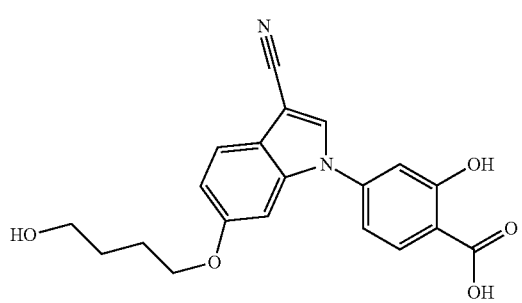 [SMILES: N#Cc1cn(-c2ccc(C(=O)O)c(O)c2)c2cc(OCCCCO)ccc12] | 1.55-1.58 (2H, m), 1.74-1.75 (2H, m), 3.43-3.46 (2H, m), 4.01-4.02 (2H, m), 7.01 (1H, d, J = 8.9 Hz), 7.13 (1H, s), 7.25-7.27 (2H, m), 7.61 (1H, d, J = 8.9 Hz), 7.99 (1H, d, J = 8.6 Hz), 8.51 (1H, s) |

TABLE 39-continued
| Ex No. | Strc | ¹H-NMR δ ppm (DMSO-d6): |
|---|---|---|
| 230 | 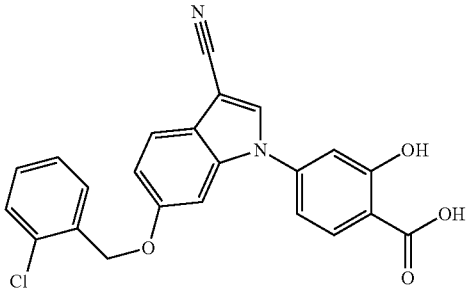 [SMILES: N#Cc1cn(-c2ccc(C(=O)O)c(O)c2)c2cc(OCc3ccccc3Cl)ccc12] | 5.23 (2H, s), 7.11 (1H, dd, J = 6.2, 2.3 Hz), 7.21-7.23 (2H, m), 7.27 (1H, d, J = 2.1 Hz), 7.38-7.40 (2H, m), 7.51-7.52 (1H, m), 7.61-7.63 (1H, m), 7.66 (1H, d, J = 8.4 Hz), 7.99 (1H, d, J = 8.1 Hz), 8.55 (1H, s) |
TABLE 40
| Ex No. | Strc | ¹H-NMR δ ppm (DMSO-d6): |
|---|---|---|
| 231 | 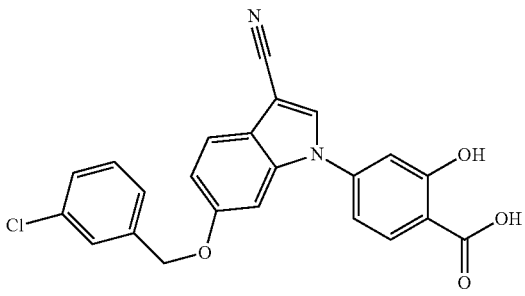 [SMILES: N#Cc1cn(-c2ccc(C(=O)O)c(O)c2)c2cc(OCc3cccc(Cl)c3)ccc12] | 5.19 (2H, s), 7.11 (1H, dd, J = 6.6, 2.2 Hz), 7.17 (1H, dd, J = 6.1, 2.1 Hz), 7.22 (1H, d, J = 1.9 Hz), 7.25 (1H, d, J = 1.9 Hz), 7.39-7.44 (3H, m), 7.54 (1H, s), 7.65 (1H, d, J = 8.7 Hz), 7.99 (1H, d, J = 8.7 Hz), 8.54 (1H, s) |
| 232 | 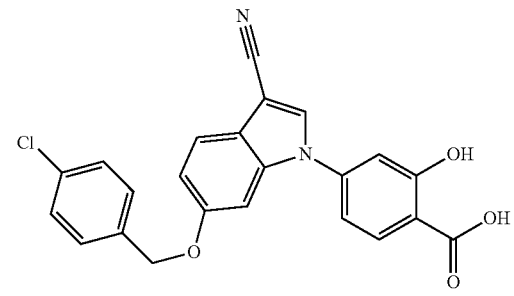 [SMILES: N#Cc1cn(-c2ccc(C(=O)O)c(O)c2)c2cc(OCc3ccc(Cl)cc3)ccc12] | 5.17 (2H, s), 7.01 (1H, dd, J = 6.7, 2.1 Hz), 7.19-7.22 (2H, m), 7.25 (1H, d, J = 2.1 Hz), 7.45-7.51 (m, 4H), 7.64 (1H, d, J = 8.8 Hz), 7.99 (1H, d, J = 8.3 Hz), 8.54 (1H, s) |
| 233 | 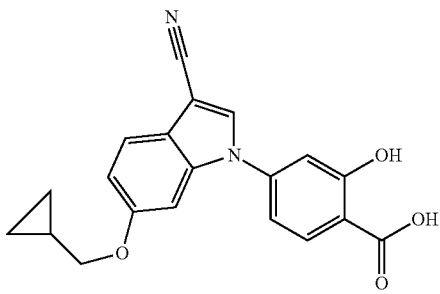 [SMILES: N#Cc1cn(-c2ccc(C(=O)O)c(O)c2)c2cc(OCC3CC3)ccc12] | 0.32-0.33 (2H, m), 0.56-0.57 (2H, m), 1.19-1.26 (1H, m), 3.85 (2H, d, J = 6.3 Hz), 7.02 (1H, dd, J = 6.6, 2.1 Hz), 7.11 (1H, d, J = 1.9 Hz), 7.23-7.25 (2H, m), 7.61 (1H, d, J = 8.7 Hz), 7.99 (1 H, d, J = 8.9 Hz), 8.51 (1H, s) |
| 234 | 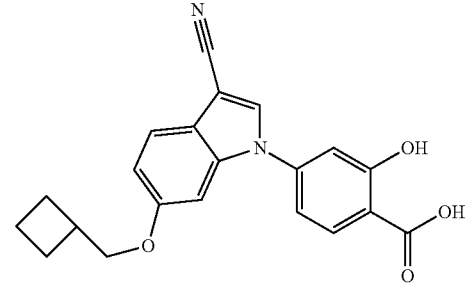 [SMILES: N#Cc1cn(-c2ccc(C(=O)O)c(O)c2)c2cc(OCC3CCC3)ccc12] | 1.83-1.90 (4H, m), 2.05-2.07 (2H, m), 2.69-2.75 (1H, m), 3.98 (2H, d, J = 6.2 Hz), 7.01 (1H, dd, J = 6.5, 2.2 Hz), 7.12 (1H, d, J = 2.2 Hz), 7.21-7.22 (2H, m), 7.61 (1H, d, J = 8.7 Hz), 7.99 (1H, d, J = 9.0 Hz), 8.51 (1H, s) |

TABLE 40-continued
| Ex No. | Strc | $^1$H-NMR δ ppm (DMSO-d6): |
|---|---|---|
| 235 | 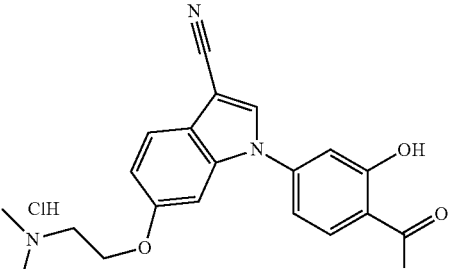 | 2.75-2.95 (6H, m), 3.40-3.60 (2H, m), 4.30-4.45 (2H, m), 7.05-7.35 (4H, m), 7.7 (1H, d, J = 8.7 Hz), 8.01 (1H, d, J = 8.3 Hz), 8.58 (1H, s), 9.86 (1H, brs.) |
| 236 | 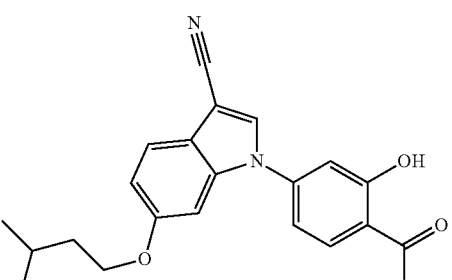 | 0.92 (6H, d, J = 6.6 Hz), 1.55-1.70 (2H, m), 1-75-1.81 (1H, m), 4.03 (2H, t, J = 6.6 Hz), 7.02 (1H, dd, J = 6.4, 2.0 Hz), 7.14 (1H, d, J = 2.0 Hz), 7.23-7.25 (2H, m), 7.61 (1H, d, J = 8.8 Hz), 7.99 (1H, d, J = 8.8 Hz), 8.51 (1H, s) |
| 237 | 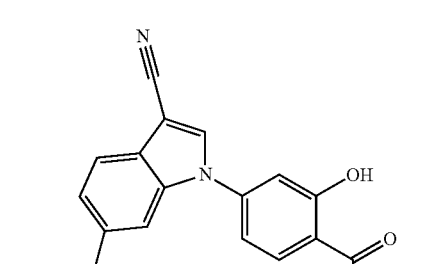 | 1.24 (6H, d, J = 7.2 Hz), 3.02-3.07 (1H, m), 7.22-7.24 (2H, m), 7.31 (1H, d, J = 8.3 Hz), 7.52 (1H, s), 7.67 (1H, d, J = 7.6 Hz), 8.00 (1H, d, J = 8.3 Hz), 8.60 (1H, s) |
TABLE 41
| Ex No. | Strc | $^1$H-NMR δ ppm (DMSO-d6): |
|---|---|---|
| 238 | | 2.94 (3H, s), 3.20-3.50 (2H, m), 4.00-4.15 (2H, m), 6.90-7.40 (5H, m), 7.65 (1H, d, J = 8.5 Hz), 6.00 (1H, d, J = 7.8 Hz), 8.53 (1H, s) |

TABLE 41-continued

| Ex No. | Strc | ¹H-NMR δ ppm (DMSO-d6): |
| --- | --- | --- |
| 239 | | 1.78 (3H, s), 1.80-1.95 (2H, m), 3.05-3.30 (2H, m), 3.95-4.15 (2H, m), 6.95-7.35 (4H, m), 7.60-7.70 (1H, m), 7.80-8.10 (2H, m), 8.52 (1H, s) |
| 240 | | 1.85-2.00 (2H, m), 2.29 (3H, s), 3.05-3.20 (2H, m), 4.07 (2H, t, J = 6.0 Hz), 7.00-7.10 (2H, m), 7.15 (1H, dd, J = 1.9 Hz), 7.20-7.35 (2H, m), 7.64 (1H, d, J = 8.8 Hz), 8.01 (1H, d, J = 9.1 Hz), 8.53 (1H, s) |
| 241 | | 5.43 (2H, s), 7.16 (1H, s), 7.25-7.55 (5H, m), 7.80-8.20 (4H, m), 8.71 (1H, s), 8.88 (1H, s) |

TABLE 42

| Ref. No. | Strc | (Solv) ¹H-NMR δ ppm: |
| --- | --- | --- |
| 24 | | (CDCl3) 2.22 (3H, s), 3.91 (3H, s), 6.85-7.15 (3H, m) |
| 25 | | (CDCl3) 2.33 (3H, s), 5.15 (1H, s), 7.06 (1H, d, J = 11.3 Hz), 7.49 (1H, d, J = 6.2 Hz) |
| 26 | | (CDCl3) 2.28 (3H, s), 3.89 (3H, s), 7.00-7.10 (1H, m), 7.46 (1H, d, J = 6.3 Hz) |
| 27 | | (CDCl3) 2.30-2.40 (3H, m), 3.86 (3H, s), 3.95 (3H, s), 5.58 (1H, s), 7.45 (1H, s), 7.69 (1H, s) |

TABLE 42-continued

| Ref. No. | Strc | (Solv) ¹H-NMR δ ppm: |
|---|---|---|
| 28 | [structure: 4-methoxy-5-methyl-2-nitrobenzyl cyanide] | (CDCl3) 2.32 (3H, s), 3.93 (3H, s), 4.13 (2H, s), 7.40-7.45 (1H, m), 7.66 (1H, s) |
| 29 | [structure: 5-methyl-6-methoxy-1H-indole] | (DMSO-d6) 2.19 (3H, s), 3.78 (3H, s), 6.20-6.30 (1H, m), 6.85 (1H, s), 7.05-7.15 (1H, m), 7.24 (1H, s), 10.8 (1H, brs.) |
| 30 | [structure: 5-methyl-6-methoxy-1H-indole-3-carbonitrile] | (DMSO-d6) 2.20-2.30 (3H, m), 3.82 (3H, s), 6.98 (1H, s), 7.37 (1H, s), 8.04 (1H, d, J = 2.8 Hz), 11.9 (1H, brs.) |
| 31 | [structure: 1-methoxy-2-methyl-4-nitrobenzene] | (DMSO-d6) 2.98 (3H, s), 3.93 (3H, s), 7.15 (1H, d, J = 8.9 Hz), 8.05-8.20 (2H, m) |
| 32 | [structure: 5-methoxy-4-methyl-2-nitrobenzyl cyanide] | (DMSO-d6) 2.22 (3H, s), 3.95 (3H, s), 4.30 (2H, s), 7.27 (1H, s), 8.09 (1H, s) |
| 33 | [structure: 5-methoxy-6-methyl-1H-indole] | (DMSO-d6) 2.22 (3H, s), 3.76 (3H, s), 6 20-6.40 (1H, m), 6.90-7.25 (3H, m), 10.75 (1H, brs.) |

TABLE 43

| Ref. No. | Strc | (Solv) ¹H-NMR δ ppm: |
|---|---|---|
| 34 | [structure: 5-methoxy-6-methyl-1H-indole-3-carbonitrile] | (DMSO-d6) 2.24 (3H, s), 3.84 (3H, s), 7.03 (1H, s), 7.30 (1H, s), 8.06 (1H, s), 11.92 (1H, brs.) |
| 35 | [structure: 5-benzyloxy-6-chloro-1H-indole] | (CDCl3) 5.17 (2H, s), 6.35-6.55 (1H, m), 7.05-7.65 (8H, m), 8.04 (1H, brs.) |
| 36 | [structure: 5-benzyloxy-6-chloro-1H-indole-3-carbaldehyde] | (CDCl3) 5.24 (2H, s), 7.25-7.65 (6H, m), 7.70-7.85 (1H, m), 7.90-8.05 (1H, m), 8.59 (1H, brs.), 10.02 (1H, s) |

TABLE 43-continued

| Ref. No. | Strc | (Solv) ¹H-NMR δ ppm: |
|---|---|---|
| 37 | | (CDCl3) 5.21 (2H, s), 7.20-7.75 (8H, m), 8.50 (1H, brs.) |
| 38 | | (CDCl3) 2.25-2.60 (3H, m), 5.10-5.45 (2H, m), 5.68 (1H, s), 7.20-770 (6H, m), 7.80-8.10 (1H, m). |
| 39 | | (CDCl3) 2.20-2.55 (3H, m), 6.35-6.55 (1H, m), 6.90-7.50 (3H, m), 8.04 (1H, brs.). |
| 40 | | (CDCl3) 2.30-2.50 (3H, m), 7.00-7.20 (1H, m), 7.70-7.90 (1H, m), 8.05-8.25 (1H, m), 8.64 (1H, brs.), 10.02 (1H, s). |
| 41 | | (CDCl3) 2.30-2.50 (3H, m), 7.00-7.20 (1H, m), 7.45-7.80 (2H, m), 8.51 (1H, brs.). |
| 42 | | (CDCl3) 3.94 (3H, s), 5.19 (2H, s), 6.35-6.50 (1H, m), 6.80-6.95 (1H, m), 7.00-7,20 (2H, m), 7.25-7.55 (5H, m), 7.92 (1H, brs.). |

TABLE 44

| Ref. No. | Strc | (Solv) ¹H-NMR δ ppm: |
|---|---|---|
| 43 | | (CDCl3) 3.74 (3H, s), 5.02 (2H, s), 7.15-7.65 (6H, m), 7.79 (1H, s), 8.25-8.50 (1H, m), 9.86 (1H, s). |

TABLE 44-continued

| Ref. No. | Strc | (Solv) ¹H-NMR δ ppm: |
|---|---|---|
| 44 | | (CDCl3) 3.84 (3H, s), 5.12 (2H, s), 7.00-7.20 (2H, m), 7.25-7.55 (5H, m), 7.90-8.15 (1H, m). |
| 45 | | (DMSO-d6) 3.81 (3H, s), 6.30-6.45 (1H, m), 7.10-7.35 (3H, m), 10.96 (1H, brs.) |
| 46 | | (DMSO-d6) 2.29 (3H, s), 2.35 (3H, s), 3.62 (3H, s), 6.20-6.40 (1H, m), 6.90-7.30 (2H, m), 10.80 (1H, brs.) |
| 47 | | (DMSO-d6) 3.85 (3H, s), 6.40-6.60 (1H, m), 7.25-7.70 (3H, m), 11.30 (1H, brs.) |
| 48 | | (DMSO-d6) 2.95-3.05 (6H, m), 7.26 (1H, d, J = 9.5 Hz), 8.20-8.40 (2H, m) |
| 49 | | (DMSO-d6) 3.00-3.15 (6H, m), 4.36 (2H, s), 7.32 (1H, s), 8.39 (1H, s) |
| 50 | | (DMSO-d6) 2.63 (6H, s), 6.40-6.60 (1H, m), 7.50-7.80 (3H, m), 11.39 (1H, brs) |
| 51 | | (DMSO-d6) 1.25-1.45 (3H, m), 2.67 (6H, s), 4.20-4.45 (2H, m), 6.75-6.90 (1H, m), 7.25-8.25 (7H, m) |

TABLE 45
| Ref. No. | Strc | (Solv) $^1$H-NMR δ ppm: |
|---|---|---|
| 52 | 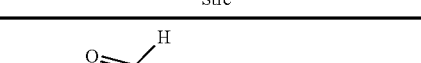 | (DMSO-d6) 1.35 (3H, t, J = 7.1 Hz), 2.70 (6H, s), 4.37 (2H, q, J = 7.1 Hz), 7.79 (1H, s), 7.85-8.30 (4H, m), 8.36 (1H, s), 8.89 (1H, s), 10.09 (1H, s) |
| 53 | 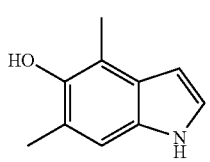 | (DMSO-d6) 2.24 (3H, s), 2.29 (3H, s), 6.15-7.20 (3H, m), 7.40 (1H, s), 10.58 (1H, brs) |
TABLE 46
| Ref. No. | Strc |
|---|---|
| 54 | 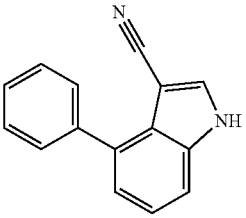 |
| 55 | 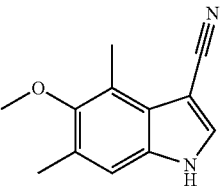 |
| 56 | 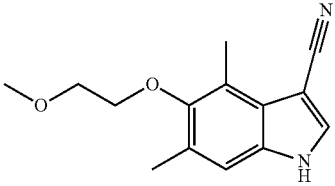 [SMILES: COCCOc1c(C)cc2[nH]cc(C#N)c2c1C] |
| 57 | 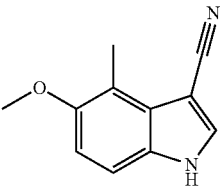 |
TABLE 46-continued
| Ref. No. | Strc |
|---|---|
| 58 | 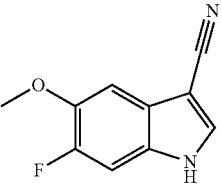 |
| 59 | 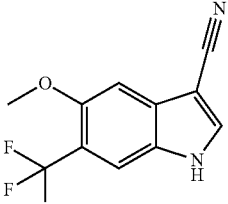 |
| 60 | 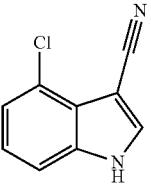 [SMILES: N#Cc1c[nH]c2cccc(Cl)c12] |
| 61 | 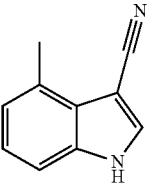 |

TABLE 46-continued
| Ref. No. | Strc |
|---|---|
| 62 | 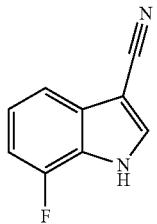 [SMILES: N#Cc1c[nH]c2c(F)cccc12] |
| 63 | 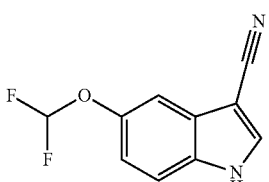 |
TABLE 47
| Ex No. | Strc | (Solv) $^1$H-NMR δ ppm: |
|---|---|---|
| 242 | 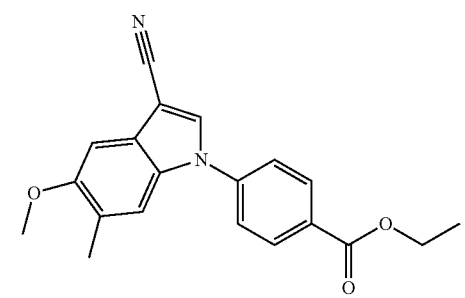 [SMILES: CCOC(=O)c1ccc(-n2cc(C#N)c3cc(OC)c(C)cc32)cc1] | (DMSO-d6) 1.36 (3H, t, J = 7.1 Hz), 2.27 (3H, s), 3.90 (3H, s), 4.36 (2H, q, J = 7.1 Hz), 7.17 (1H, s), 7.52 (1H, s) 7.75-8.25 (4H, m), 8.55 (1H, s) |
| 243 | 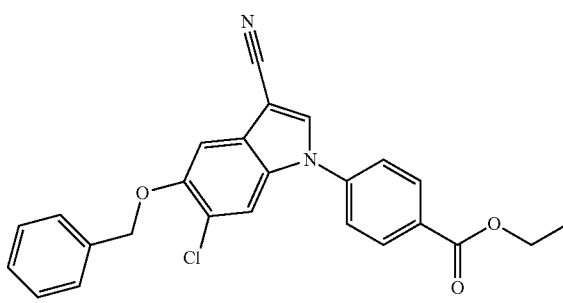 | (CDCl3) 1.44 (3H, t, J = 7.1 Hz), 4.44 (2H, d, J = 7.1 Hz), 5.25 (2H, s), 7.25-7.85 (10H, m), 8.15-8.35 (2H, m) |
| 244 | 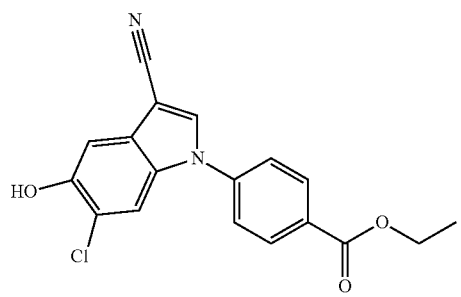 [SMILES: CCOC(=O)c1ccc(-n2cc(C#N)c3cc(O)c(Cl)cc32)cc1] | (CDCl3) 1.44 (3H, t, J = 7.1 Hz), 4.45 (2H, d, J = 7.1 Hz), 5.55 (1H, s), 7.43 (1H, s), 7.45-7.65 (3H, m), 7.80 (1H, s), 8.15-8.35 (2H, m) |
| 245 | 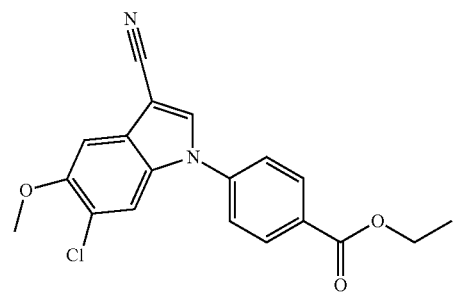 [SMILES: CCOC(=O)c1ccc(-n2cc(C#N)c3cc(OC)c(Cl)cc32)cc1] | (CDCl3) 1.44 (3H, t, J = 7.2 Hz), 4.01 (3H, s), 4.44 (2H, q, J = 7.2 Hz), 7.20-7.35 (1H, m), 7.45-7.65 (3H, m), 7.79 (1H, s), 8.20-8.35 (2H, m) |

TABLE 47-continued

| Ex No. | Strc | (Solv) $^1$H-NMR δ ppm: |
|---|---|---|
| 246 | | (CDCl3) 1.45 (3H, t, J = 7.1 Hz), 4.46 (2H, d, J = 7.1 Hz), 7.45-7.65 (2H, m), 7.57 (1H, s), 7.81 (1H, s), 7.93 (1H, s), 8.20-8.40 (2H, m) |
| 247 | | (CDCl3) 1.44 (3H, t, J = 7.1 Hz), 2.52 (3H, s), 4.45 (2H, q, J = 7.1 Hz), 7.45-7.65 (3H, m), 7.68 (1H, s), 7.79 (1H, s), 8.20-8.35 (2H, m) |
| 248 | | (CDCl3) 1.30-1.60 (3H, m), 2.42 (3H, s), 4.30-4.55 (2H, m), 7.10-7.35 (1H, m), 7.45-7.70 (3H, m), 7.78 (1H, s), 8.15-8.35 (2H, m). |

TABLE 48

| Ex No. | Strc | (Solv) $^1$H-NMR δ ppm: |
|---|---|---|
| 249 | | (CDCl3) 1.45 (3H, t, J = 7.2 Hz), 2.35-2.50 (3H, m), 4.46 (2H, q, J = 7.2 Hz), 7.45-7.65 (2H, m), 8.00-8.15 (1H, m), 8.20 (1H, s), 8.40-8.60 (1H, m), 9.10-9.30 (1H, m). |
| 250 | | (CDCl3) 1.42 (3H, t, J = 7.1 Hz), 2.35-2.45 (3H, m), 3.55 (3H, s), 4.41 (2H, q, J = 7.1 Hz), 5.31 (2H, s), 7.05-7.40 (3H, m), 7.50-7.65 (1H, m), 7.77 (1H, s), 7.90-8.05 (1H, m). |

TABLE 48-continued

| Ex No. | Strc | (Solv) ¹H-NMR δ ppm: |
|---|---|---|
| 251 | | (CDCl3) 1.45 (3H, t, J = 7.1 Hz), 4.00 (3H, s), 4.45 (2H, q, J = 7.1 Hz), 5.15 (2H, s), 6.98 (1H, s), 7.22 (1H, s), 7.25-7.50 (7H, m), 7.66 (1H, s), 8.10-8.30 (2H, m). |
| 252 | | (CDCl3) 1.44 (3H, t, J = 7.2 Hz), 4.02 (3H, s), 4.44 (2H, q, J = 7.2 Hz), 7.12 (1H, s), 7.19 (1H, s), 7.45-7.65 (2H, m), 7.68 (1H, s), 8.15-8.35 (2H, m). |
| 253 | | (CDCl3) 0.50-0.70 (2H, m), 0.85-1.05 (2H, m), 1.44 (3H, t, J = 7.2 Hz), 2.10-2.34 (1H, m), 3.97 (3H, s), 4.44 (2H, q, J = 7.2 Hz), 7.03 (1H, s), 7.17 (1H, s), 7.40-7.65 (2H, m), 7.71 (1H, s), 8.10-8.40 (2H, m). |
| 254 | | (CDCl3) 1.44 (3H, t, J = 7.1 Hz), 2.36 (3H, s), 4.44 (2H, q, J = 7.1 Hz), 7.17 (1H, s), 7.31 (1H, s), 7.45-7.65 (2H, m), 7.72 (1H, s), 8.15-8.35 (2H, m). |

TABLE 49

| Ex No. | Strc | (Solv) $^1$H-NMR δ ppm: |
|---|---|---|
| 255 | | (CDCl3) 1.44 (3H, t, J = 7.1 Hz), 2.37 (3H, s), 2.41 (3H, s), 4.44 (2H, q, J = 7.1 Hz), 7.33 (1H, s), 7.45-7.65 (3H, m), 7.72 (1H, s), 8.15-8.35 (2H, m). |
| 256 | | (DMSO-d6) 1.36 (3H, t, J = 7.1 Hz), 3.96 (3H, s), 4.36 (2H, q, J = 7.1 Hz), 7.35 (4H, m), 8.66 (1H, s) |
| 257 | | (DMSO-d6) 7.10-8.20 (6H, m), 8.59 (1H, s), 10.05 (1H, s), 13.22 (1H, brs). |
| 258 | | (DMSO-d6) 3.20-3.40 (6H, m), 3.60-3.80 (4H, m), 4.20-4.60 (4H, m), 7.35-8.25 (6H, m), 8.66 (1H, s). |

TABLE 50

| Ex No. | Strc |
|---|---|
| 259 | |

TABLE 50-continued

| Ex No. | Strc |
|---|---|
| 260 | |

TABLE 50-continued

| Ex No. | Strc |
|---|---|
| 261 | |
| 262 | |
| 263 | |
| 264 | |
| 265 | |
| 266 | |
| 267 | |
| 268 | |
| 269 | |
| 270 | |

TABLE 51
| Ex No. | Strc |
|---|---|
| 271 | 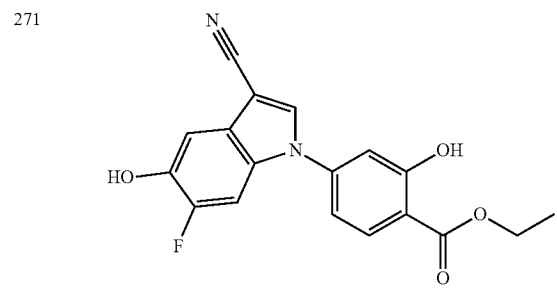 |
| 272 | 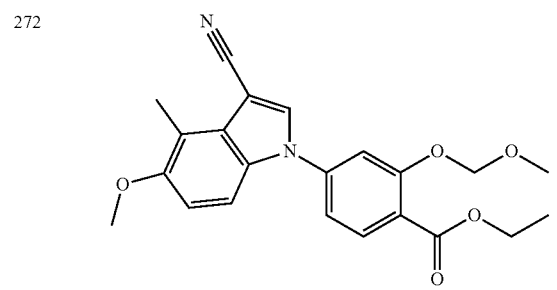 |
| 273 | 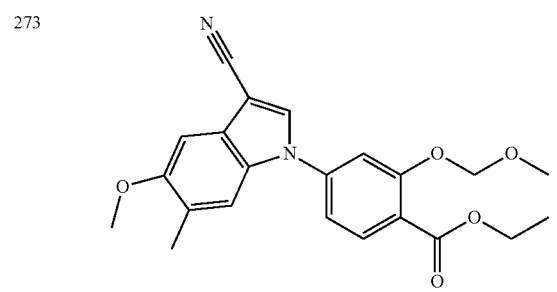 |
| 274 | 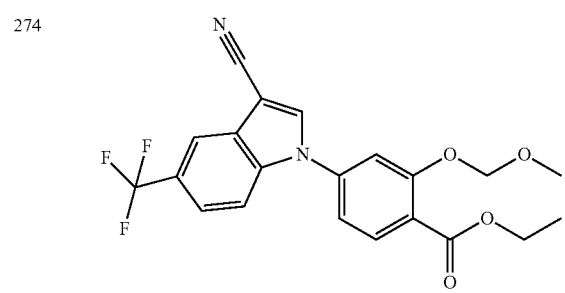 |
| 275 | 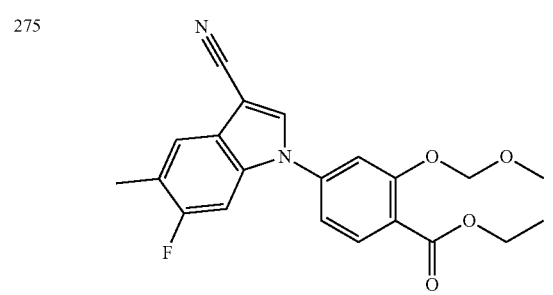 |
TABLE 51-continued
| Ex No. | Strc |
|---|---|
| 276 | 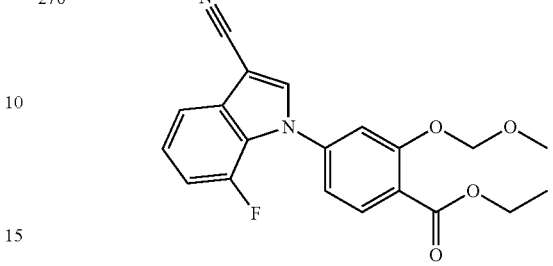 |
| 277 | 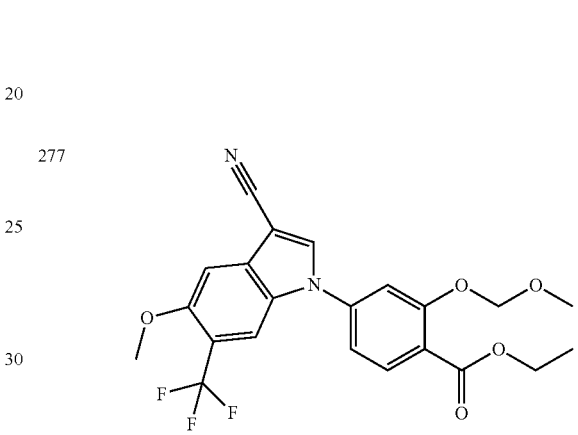 |
| 278 | 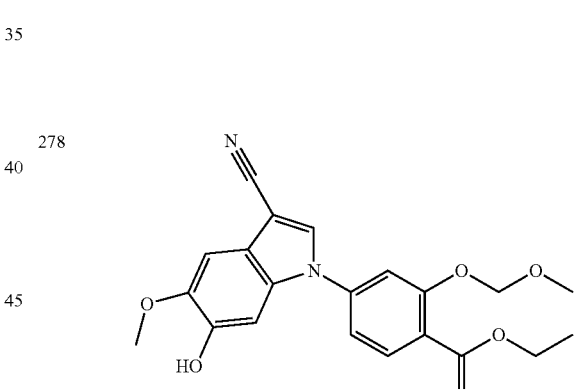 |
| 279 | 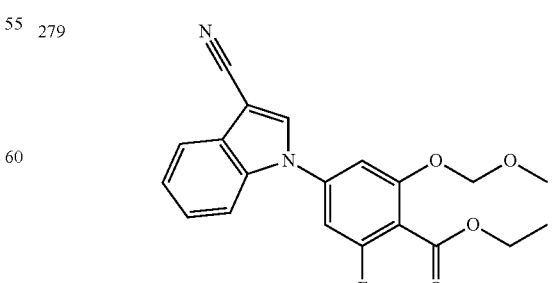 |

TABLE 51-continued

| Ex No. | Strc |
|---|---|
| 280 | (ethyl 4-(3-cyano-5-ethoxy-6-fluoro-1H-indol-1-yl)benzoate) |
| 281 | (ethyl 4-(3-cyano-6-fluoro-5-isopropoxy-1H-indol-1-yl)benzoate) |
| 282 | (isopentyl 4-(3-cyano-6-fluoro-5-(isopentyloxy)-1H-indol-1-yl)benzoate) |

TABLE 52

| Ex No. | Strc |
|---|---|
| 283 | (ethyl 4-(3-cyano-5-(dimethylamino)-6-(trifluoromethyl)-1H-indol-1-yl)benzoate) |

TABLE 53

| Ex No. | Strc | $^1$H-NMR δ ppm: DMSO-d6 |
|---|---|---|
| 284 | (4-(3-cyano-6-methoxy-5-methyl-1H-indol-1-yl)benzoic acid) | 2.28 (3H, s), 3.82 (3H, s), 7.05-7.15 (1H, s), 7.45-7.55 (1H, s), 7.75-7.90 (2H, m), 8.10-8.25 (2H, m), 8.47 (1H, s), 13.19 (1H, brs.) |
| 285 | (4-(3-cyano-5-methoxy-6-methyl-1H-indol-1-yl)benzoic acid) | 2.27 (3H, s), 3.90 (3H, s), 7.10-8.25 (6H, m), 8.53 (1H, s) |

TABLE 53-continued
| Ex No. | Strc | $^1$H-NMR δ ppm: DMSO-d6 |
|---|---|---|
| 286 | 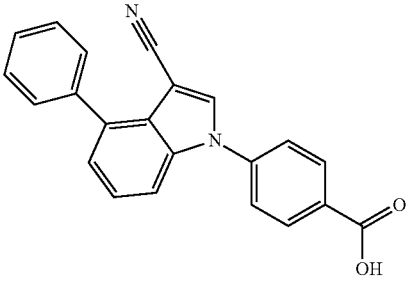 [SMILES: N#Cc1cn(-c2ccc(C(=O)O)cc2)c2cccc(-c3ccccc3)c12] | 7.25-7.35 (1H, m), 7.40-7.60 (7H, m), 7.80-7.90 (2H, m), 8.10-8.25 (2H, m), 8.75 (1H, s), 13.3 (1H, brs.) |
| 287 | 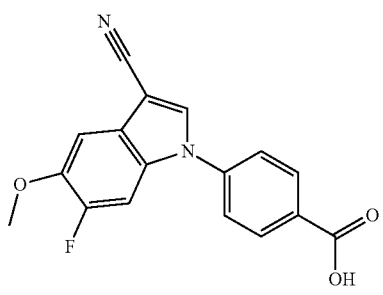 [SMILES: COc1cc2c(C#N)cn(-c3ccc(C(=O)O)cc3)c2cc1F] | 3.96 (3H, s), 7.35-8.20 (6H, m), 8.64 (1H, s), 13.26 (1H, brs.) |
| 288 | 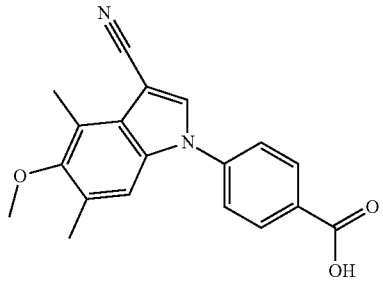 [SMILES: COc1c(C)cc2c(c(C#N)cn2-c2ccc(C(=O)O)cc2)c1C] | 2.33 (3H, s), 2.62 (3H, s), 3.69 (3H, s), 7.35 (1H, s), 7.65-8.20 (4H, m), 8.58 (1H, s), 13.28 (1H, brs.) |
| 289 | 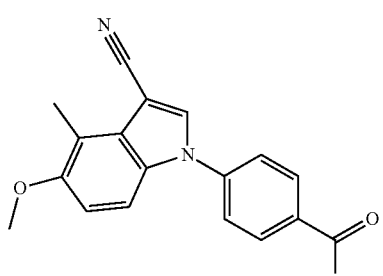 | 2.56 (3H, s), 3.84 (3H, s), 7.14 (1H, d, J = 9.2 Hz), 7.45-7.55 (1H, m), 7.75-7.85 (2H, m), 8.10-8.20 (2H, m), 8.65 (1H, s), 13.24 (1H, brs.) |
| 290 | 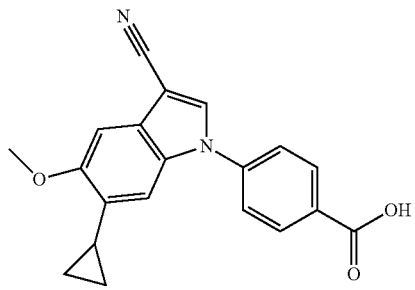 [SMILES: COc1cc2c(C#N)cn(-c3ccc(C(=O)O)cc3)c2cc1C1CC1] | 0.55-0.75 (2H, m), 0.80-1.00 (2H, m), 2.05-2.30 (1H, m), 3.93 (3H, s), 7.09 (1H, s), 7.18 (1H, s), 7.64 (2H, m), 8.05-8.25 (2H, m), 8.52 (1H, s), 13.18 (1H, brs.). |

TABLE 54

| Ex No. | Strc | ¹H-NMR δ ppm: DMSO-d6 |
|---|---|---|
| 291 | | 2.33 (3H, s), 2.62 (3H, s), 3.36 (3H, s), 3.60-3.95 (4H, m), 7.74 (1H, s), 7.76-8.25 (4H, m), 8.57 (1H, s) |
| 292 | | 2.27 (3H, s), 2.56 (3H, s), 6.50-8.50 (7H, m) |
| 293 | | 3.97 (3H, s), 7.40 (1H, s), 7.65-7.95 (3H, m), 8.05-8.25 (2H, m), 8.68 (1H, s), 13.22 (1H, brs.) |
| 294 | | 3.20-3.45 (3H, m), 3.60-3.90, (2H, m), 4.15-4.45 (2H, m), 4.23 (1H, s), 7.65-7.95 (3H, m), 8.05-8.30 (2H, m), 8.68 (1H, s), 13.23 (1H, brs.) |
| 295 | | 2.35-2.60 (3H, m), 7.65-7.95 (4H, m), 8.05-8.25 (2H, m), 8.70 (1H, s), 13.24 (1H, brs.) |

TABLE 54-continued

| Ex No. | Strc | ¹H-NMR δ ppm: DMSO-d6 |
|---|---|---|
| 296 | | 2.24 (3H, s), 7.03 (1H, s), 7.44 (1H, s), 7.60-7.90 (2H, m), 7.95-8.30 (2H, m), 8.46 (1H, s), 9.56 (1H, brs.), 13.20 (1H, brs.). |
| 297 | | 2.34 (3H, s), 2.37 (3H, s), 7.40-7.60 (2H, m), 7.70-7.85 (2H, m), 8.05-8.25 (2H, m), 8.53 (1H, s). |

TABLE 55

| Ex No. | Strc | ¹H-NMR δ ppm: DMSO-d6 |
|---|---|---|
| 298 | | 2.38 (3H, s), 7.30-8.40 (6H, m), 8.66 (1H, s), 13.22 (1H, brs.) |
| 299 | | 7.10-7.65 (3H, m), 7.70-7.90 (3H, m), 8.10-8.25 (2H, m), 8.79 (1H, s), 13.29 (1H, brs.) |
| 300 | | 2.72 (6H, s), 7.75-7.90 (3H, m), 7.98 (1H, s), 8.10-8.25 (2H, m), 8.87 (1H, s) |

TABLE 55-continued

| Ex No. | Strc | ¹H-NMR δ ppm: DMSO-d6 |
|---|---|---|
| 301 | | 1.32 (6H, d, J = 6.0 Hz), 4.80-5.10 (1H, m), 7.55 (1H, s), 7.70-8.30 (5H, m), 8.83 (1H, s), 13.33 (1H, brs.) |
| 302 | | 1.40 (3H, t, J = 7.1 Hz), 4.21 (2H, q, J = 7.1 Hz), 7.30-8.25 (6H, m), 8.65 (1H, s), 13.25 (1H, brs.) |
| 303 | | 1.32 (6H, d, J = 6.1 Hz), 4.60-4.90 (1H, m), 7.30-8.30 (6H, m), 8.66 (1H, s), 13.27 (1H, brs.) |
| 304 | | 0.96 (6H, d, J = 6.7 Hz), 1.50-2.00 (3H, m), 4.10-4.30 (2H, m), 7.30-8.30 (6H, m), 8.65 (1H, s), 13.29 (1H, brs.) |

TABLE 56

| Ex No. | Strc | ¹H-NMR δ ppm: DMSO-d6 |
|---|---|---|
| 305 | | 3.33 (3H, s), 3.65-3.80 (2H, m), 4.20-4.40 (2H, m), 7.35-8.25 (6H, m), 8.66 (1H, s), 13.29 (1H, brs.) |

TABLE 56-continued

| Ex No. | Strc | $^1$H-NMR δ ppm: DMSO-d6 |
|---|---|---|
| 306 | | 3.89 (3H, s), 7.14 (1H, s), 7.80-8.15 (2H, m), 8.35-8.55 (1H, m), 8.79 (1H, s), 8.95-9.15 (1H, m), 9.37 (1H, brs.), 13.48 (1H, brs.). |
| 307 | | 2.39 (3H, s), 7.55-7.80 (1H, m), 7.90-8.10 (1H, m), 8.30-8.60 (2H, m), 8.90-9.25 (2H, m), 13.52 (1H, brs.). |
| 308 | | 3.44 (3H, s), 5.38 (2H, s), 7.26-7.55 (4H, m), 7.65-8.00 (3H, m), 8.68 (1H, s), 12.99 (1H, brs.). |
| 309 | | 7.20-7.30 (2H, m), 7.35-7.50 (2H, m), 7.67 (1H, dd, J = 8.0 Hz, 1.0 Hz), 8.01 (1H, d, J = 8.7 Hz), 8.81 (1H, s) |
| 310 | | 2.72 (3H, s), 7.14 (1H, d, J = 7.2 Hz), 7.20-7.35 (3H, m), 7.52 (1H, d, J = 8.5 Hz), 8.00 (1H, d, J = 8.1 Hz), 8.66 (1H, s) |

TABLE 56-continued

| Ex No. | Strc | ¹H-NMR δ ppm: DMSO-d6 |
|---|---|---|
| 311 | | 3.95 (3H, s), 7.15-8.05 (5H, m), 8.63 (1H, s) |

TABLE 57

| Ex No. | Strc | ¹H-NMR δ ppm: DMSO-d6 |
|---|---|---|
| 312 | | 7.10-7.30 (3H, m), 7.50-8.05 (2H, m), 8.57 (1H, s), 10.06 (1H, s) |
| 313 | | 2.55 (3H, s), 3.84 (3H, s), 7.14 (1H, d, J = 9.0 Hz), 7.18-7.30 (2H, m), 7.45-7.55 (1H, m), 7.95-8.05 (1H, m), 8.63 (1H, s), |
| 314 | | 2.27 (3H, s), 3.90 (3H, s), 7.10-7.25 (3H, m), 7.52 (1H, s), 7.90-8.05 (1H, m), 8.50 (1H, s) |
| 315 | | 7.20-7.40 (2H, m), 7.65-7.80 (1H, m), 7.85-7.95 (1H, m), 8.03 (1H, d, J = 8.6 Hz), 8.05-8.20 (1H, m), 8.88 (1H, s) |

TABLE 57-continued

| Ex No. | Strc | ¹H-NMR δ ppm: DMSO-d6 |
|---|---|---|
| 316 | | 2.38 (3H, s), 7.10-7.35 (2H, m), 7.40-7.75 (2H, m), 7.90-8.20 (1H, m), 8.64 (1H, s). |
| 317 | | 3.87 (3H, s), 6.95-7.35 (4H, m), 7.90-8.10 (1H, m), 8.39 (1H, s), 9.38 (1H, brs.). |
| 318 | | 7.10-7.45 (4H, m), 7.59 (1H, d, J = 7.8 Hz), 7.95 (1H, d, J = 8.2 Hz), 8.63 (1H, s) |

TABLE 58

| Ex No. | Strc | ¹H-NMR δ ppm: DMSO-d6 |
|---|---|---|
| 319 | | 4.00 (3H, s), 7.10-8.10 (5H, m), 8.81 (1H, s) |
| 320 | | 7.10-7.65 (5H, m), 7.77 (1H, d, J = 9.0 Hz), 8.01 (1H, d, J = 8.4 Hz), 8.76 (1H, s), |

TABLE 58-continued

| Ex No. | Strc | ¹H-NMR δ ppm: DMSO-d6 |
|---|---|---|
| 321 | | 7.15-7.30 (1H, m), 7.35-7.50 (3H, m), 7.70-7.85 (2H, m), 8.60-8.65 (1H, m) |
| 322 | | 2.45 (3H, s), 7.20-7.30 (3H, m), 7.52 (1H, s), 7.64 (1H, d, J = 8.0 Hz), 8.01 (1H, d, J = 8.0 Hz), 8.57 (1H, s) |
| 323 | | 1.32 (3H, t, J = 7.3 Hz), 2.24 (3H, s), 3.44 (3H, s), 4.31 (2H, q, J = 7.3 Hz), 5.38 (2H, s), 7.03 (1H, s), 7.30-7.50 (3H, m), 7.86 (1H, d, J = 8.4 Hz), 8.44 (1H, s), 9.56 (1H, s) |
| 324 | | 2.28 (3H, s), 3.70-3.80 (2H, m), 4.15-4.30 (2H, m), 7.10-7.30 (3H, m), 7.53 (1H, s), 7.95-8.05 (1H, m), 8.50 (1H, s) |
| 325 | | 2.24 (3H, s), 7.02 (1H, s), 7.15-7.25 (2H, m), 7.46 (1H, s), 7.98 (1H, d, J = 9.0 Hz), 8.44 (1H, s), 9.56 (1H, s) |

TABLE 59

| Ex No. | Strc | ¹H-NMR δ ppm: DMSO-d6 |
|---|---|---|
| 326 | (structure) | 1.32 (6H, d, J = 5.9 Hz), 2.25 (3H, s), 4.65-4.80 (1H, m), 7.10-8.10 (5H, m), 8.49 (1H, s) |
| 327 | (structure) | 1.25 (3H, t, J = 7.5 Hz), 2.78 (2H, q, J = 7.5 Hz), 7.10-7.40 (3H, m), 7.50-7.75 (2H, m), 7.90-8.10 (1H, m), 8.63 (1H, s) |
| 328 | (structure) | 2.38 (3H, s), 6.70-6.80 (1H, m), 7.01 (1H, d, J = 2.3 Hz), 7.49 (1H, d, J = 10.6 Hz), 7.60-7.80 (1H, m), 7.89 (1H, d, J = 8.5 Hz), 8.58 (1H, s) |

Test Example 1

Xanthine Oxidase Inhibitory Activity (1) Preparation of Test Compounds

Test compounds were dissolved in DMSO (Wako) at 40 mM concentration and then diluted to intended concentrations with phosphate-buffered saline (PBS).

(2) Method for Measurement

Xanthine oxidase (from bovine milk, Sigma) was prepared with phosphate-buffered saline (PBS) at 0.02 units/mL, and then the solution was added to 96 well plates at 50 μL/well. In addition, test compounds diluted with PBS were added at 50 μL/well. Xanthine (Wako) at 200 μM prepared with PBS was added at 100 μL/well, and the reaction was conducted for 10 minutes at room temperature. Absorbance at 290 nm was measured using a microplate reader SpectraMax Plus 384 (Molecular device). The absorbance under a condition without xanthine is 0%, and control without test compounds is 100%. Fifty % inhibitory concentration of a test compound ($IC_{50}$) was calculated (Table 60). Ex. No in the table indicates Example number.

TABLE 60

| Ex. No | $IC_{50}$ (nM) |
|---|---|
| 3 | 6.5 |
| 5 | 33.6 |
| 8 | 41.5 |
| 9 | 12.5 |
| 12 | 7.0 |
| 15 | 15.5 |
| 17 | 12.1 |
| 19 | 96.0 |
| 27 | 14.6 |
| 29 | 43.3 |
| 32 | 91.1 |
| 34 | 48.3 |
| 42 | 175.3 |
| 45 | 72.9 |
| 47 | 58.6 |
| 143 | 24.4 |
| 149 | 38.0 |
| 150 | 20.6 |
| 151 | 22.4 |
| 152 | 15.8 |
| 153 | 12.2 |
| 154 | 19.0 |
| 155 | 111.7 |
| 156 | 11.9 |
| 157 | 14.1 |
| 158 | 9.5 |
| 159 | 14.4 |

TABLE 60-continued

| Ex. No | IC$_{50}$ (nM) |
|---|---|
| 160 | 11.3 |
| 161 | 49.8 |
| 162 | 16.5 |
| 165 | 111.2 |
| 166 | 7.2 |
| 167 | 10.9 |
| 170 | 20.0 |
| 171 | 10.9 |
| 172 | 8.0 |
| 174 | 24.4 |
| 175 | 22.2 |
| 176 | 18.3 |
| 177 | 16.4 |
| 178 | 12.9 |
| 179 | 8.0 |
| 180 | 29.0 |
| 181 | 17.2 |
| 182 | 16.3 |
| 183 | 7.5 |
| 184 | 138.3 |
| 185 | 40.2 |
| 186 | 49.7 |
| 187 | 16.4 |
| 188 | 5.0 |
| 189 | 13.9 |
| 190 | 5.4 |
| 191 | 3.9 |
| 192 | 4.3 |
| 193 | 4.6 |
| 194 | 8.3 |
| 195 | 14.5 |
| 196 | 6.7 |
| 197 | 9.0 |
| 198 | 54.6 |
| 199 | 49.2 |
| 200 | 39.4 |
| 201 | 5.5 |
| 202 | 61.8 |
| 203 | 7.1 |
| 205 | 27.6 |
| 206 | 7.2 |
| 207 | 7.3 |
| 208 | 6.0 |
| 209 | 11.0 |
| 210 | 7.0 |
| 211 | 6.2 |
| 212 | 5.1 |
| 213 | 7.2 |
| 214 | 11.0 |
| 215 | 10.5 |
| 216 | 7.4 |
| 217 | 6.0 |
| 218 | 6.0 |
| 219 | 8.3 |
| 220 | 9.4 |
| 221 | 71.5 |
| 222 | 41.8 |
| 223 | 7.5 |
| 224 | 9.7 |
| 225 | 4.6 |
| 226 | 10.0 |
| 227 | 10.4 |
| 228 | 7.5 |
| 229 | 7.1 |
| 230 | 67.1 |
| 231 | 29.1 |
| 232 | 42.5 |
| 233 | 7.2 |
| 234 | 86.5 |
| 235 | 14.2 |
| 237 | 12.6 |
| 238 | 8.3 |
| 239 | 6.5 |
| 240 | 9.8 |
| 286 | 58 |
| 287 | 16 |
| 288 | 10 |
| 293 | 14 |
| 295 | 9 |
| 298 | 12 |
| 300 | 96 |
| 303 | 10 |
| 307 | 13 |
| 308 | 45 |
| 316 | 10 |
| 318 | 12 |

Test Example 2

Inhibitory Activity of Uric Acid Transport with Brush-Border Membrane Vesicles (BBMV)

Inhibitory activity of uric acid transport of test compounds was performed on the basis of methods described in a reference (Am. J. Physiol. 266 (Renal Fluid Electrolyte Physiol. 35): F797-F805, 1994) with a partial modification.

(1) Preparation of BBMV from Human Kidney Cortex

BBMV from human kidney cortex were purchased from KAC. Renal cortex was dissected from human kidney and cut into small pieces. Then, the cortex was homogenized in 5 volumes of ice-cold isotonic buffer (300 mM mannitol, 5 mM ethylene glycol-bis-(1-aminoethylether)-N,N,N',N'-tetraacetic acid (EGTA), 12 mM tris(hydroxymethyl)aminomethane (Tris).HCl, pH 7.4). After adding 1 M magnesium chloride to a final concentration of 12 mM, and then the suspension was mixed and allowed to stand on ice for 15 minutes. The homogenized solution was centrifuged at 2,500×g for 15 minutes at 4° C., furthermore, the supernatant was centrifuged at 30,000×g for 30 minutes at 4° C. The pellet was resuspended in ice-cold buffer 1 (150 mM mannitol, 2.5 mM EGTA, 6 mM Tris.HCl, pH 7.4). After adding 1 M magnesium chloride to a final concentration of 12 mM, and then the suspension was mixed and allowed to stand on ice for 15 minutes. After centrifugation again at 2,500×g for 15 minutes at 4° C., furthermore, the supernatant was centrifuged at 30,000×g for 30 minutes at 4° C. The pellet was resuspended in ice-cold buffer 2 (100 mM mannitol, 100 mM potassium gluconate, 20 mM 2-[4-(2-hydroxyethyl)-1-piperazinyl]ethanesulfonic acid (Hepes)-Tris, pH 7.4). After centrifugation at 30,000×g for 30 minutes at 4° C., the pellet was resuspended in buffer 2, and then the protein concentration was determined.

(2) Preparation of Test Compounds

Test compounds were dissolved in DMSO (Wako) at 40 mM concentration and then diluted to 2 times higher concentration than intended with Cl⁻ gradient buffer (100 mM mannitol, 100 mM potassium gluconate, 20 mM Hepes-Tris, pH 7.4). Cl⁻ gradient buffer without test compounds was used for control. Furthermore, an equal volume of Cl⁻ gradient buffer containing $^{14}$C-labeled uric acid (Moravek) and probenecid (Wako) was added to test compounds and control, and finally assay buffer including 40 μM uric acid and 5 μM probenecid was prepared. To measure the uptake of $^{14}$C-labeled uric acid through Cl⁻ gradient independent manner, assay buffer was prepared with Cl⁻ equilibrium buffer (100 mM mannitol, 60 mM potassium gluconate, 40 mM potassium chloride, 20 mM Hepes-Tris, pH 7.4) in place of Cl⁻ gradient buffer.

(3) Method for Measurement

BBMV were thawed on ice. After adding 8 mL of intravesicular buffer (100 mM mannitol, 60 mM potassium gluconate, 40 mM potassium chloride, 20 mM Hepes-Tris, pH 7.4) to 200 μL of prepared BBMV (protein concentration: 16 mg/mL), the BBMV were suspended through 25-gauge needle and allowed to equilibrate at room temperature for 60 minutes. After centrifugation at 30,000×g for 30 minutes at 4° C., the pellet was resuspended in 1.2 mL of intravesicular buffer. The suspension was kept on ice until the beginning of the measurement. The uptake of uric acid into BBMV was measured by the rapid-filtration technique. Requirement of BBMV (20 µL/1 reaction) was warmed for 20 minutes at room temperature. The uptake of uric acid was initiated by mixing with 100 µL of assay buffer. After incubation for 20 seconds at room temperature, 3 mL of ice-cold stop solution (300 mM mannitol, 60 mM sodium sulfate, 100 µM probenecid (Wako), 5 mM Tris-$H_2SO_4$, pH 7.4) was added, and then the solutions were filtered rapidly through nitrocellulose filters (0.65 µm pore size, Sartorius) kept under suction. Furthermore, filters were washed twice with 3 mL of stop solution and dissolved in 10 mL of Filter-Count (PerkinElmer), and the radioactivity was counted in a liquid scintillation counter (PerkinElmer). The radioactivity associated with the filters in the absence of BBMV was used as corrections. In addition, percent inhibition of test compounds at 10 µM was calculated according to the formula described below (Table 61). Ex. No, Conc. and inhibition % in the table indicate Example number, concentration of test compounds (µM) and percent inhibiton (%), respectively.

Percent inhibition (%)=[1−(B−C)/(A−C)]×100

A: Radioactivity in control
B: Radioactivity in the case of addition of test compounds
C: Radioactivity in Cl⁻ equilibrium buffer

TABLE 61

| Ex. No | Conc. (µM) | inhibition % |
|---|---|---|
| 237 | 10 | 64 |

Test Example 3

Inhibitory Activity of Uric Acid Transport with Human URAT1 Expressing Cells (1) Preparation of Transiently Human URAT1 Expressing Cells Full length human URAT1 cDNA (NCBI Accession No. NM_144585) was subcloned into expression vector, pcDNA3.1 (Invitrogen). Human URAT1 expression vector was transfected into COS7 cells (RIKEN CELL BANK RCB0539) using Lipofectamine 2000. COS7 cells were cultured in collagen-coated 24 well plates (Asahi Techno Glass) at 2×10⁵/well in D-MEM culture medium (Invitrogen) containing 10% fetal bovine serum (Sanko Junyaku) for 2 hours at 37° C. under the condition of 5% $CO_2$. For 1 well, 2 µL of Lipofectamine 2000 was diluted in 50 µL of OPTI-MEM (Invitrogen) and allowed to stand at room temperature for 7 minutes (hereinafter referred to as Lipo2000-OPTI). For 1 well, 0.8 g of human URAT1 expression vector was diluted in 50 µL of OPTI-MEM (Invitrogen) and combined gently with Lipo2000-OPTI. After standing at room temperature for 25 minutes, the mixture was added to COS7 cells at 100 µL/well. Furthermore, COS7 cells were cultured for 2 days at 37° C. under the condition of 5% $CO_2$ and used for measuring inhibitory activity on the uptake.

(2) Preparation of Test Compounds
Test compounds were dissolved in DMSO (Wako) at 10 mM concentration and then diluted to 2 times higher concentration than intended with pre-treatment buffer (125 mM sodium gluconate, 4.8 mM potassium gluconate, 1.2 mM potassium dihydrogen phosphate, 1.2 mM magnesium sulfate, 1.3 mM calcium gluconate, 5.6 mM glucose, 25 mM Hepes, pH 7.4). Pre-treatment buffer without test compounds was used for control. In addition, an equal volume of pre-treatment buffer containing ¹⁴C-labeled uric acid (Moravek) was added to test compounds and control, and finally assay buffer including 20 µM uric acid was prepared.

(3) Method for Measurement

All tests were performed on hot-plate at 37° C. Pre-treatment buffer and assay buffer were incubated at 37° C. and then used for assays. Medium was removed from plates, and 700 µL of pre-treatment buffer was added, and the cells were pre-incubated for 10 minutes. After repeating same step, pre-treatment buffer was removed, and assay buffer was added at 400 µL/well. The uptake reaction was carried out for 5 minutes. After terminating the reaction, assay buffer was rapidly removed, and the cells were washed twice with addition of ice-cold pre-treatment buffer at 1.2 mL/well. Then, the cells were lysed by addition of 0.2 N sodium hydroxide at 300 µL/well. The lysed solutions were transferred into Picoplate (PerkinElmer), and Microscinti 40 (PerkinElmer) was added at 600 µL/well. After mixing, the radioactivity was counted in a liquid scintillation counter (PerkinElmer). The radioactivity in COS7 cells not transfected with URAT1 expression vector was also counted under the same condition as control. In addition, percent inhibition of test compounds at 10 µM was calculated according to the formula described below (Table 62). In the table Ex. No, Conc. and inhibition % indicate Example number, concentration of test compound (µM) and percent inhibition (%), respectively.

Percent inhibition (%)=[1−(B−C)/(A−C)]×100

A: Radioactivity in control
B: Radioactivity in the case of addition of test compounds
C: Radioactivity in COS7 cells not transfected with URAT1 expression vector

TABLE 62

| Ex. No | Conc. (µM) | inhibition % |
|---|---|---|
| 193 | 10 | 47 |
| 194 | 10 | 64 |

Test Example 4

Serum Hypouricemic Effect (1) Method for Measurement
Test compounds at 3 mg/kg suspended in 0.5% methylcellulose solution were administered orally to overnight fasted male CD (SD) IGS rats (5-week-old, Charls River Japan). At 2 hours after administration, blood was collected under ether anesthesia from abdominal aorta, and serum was separated according to general method. Serum uric acid values were determined by use of uric acid measurement kit (Uric acid C-Test Wako: Wako), and percent decrease in uric acid was calculated according to the formula described below.

Percent decrease in uric acid (%)=(Serum uric acid values in control animals−Serum uric acid values in animals administered test compounds)×100/Serum uric acid values in control animals (2) Results
Compounds of example 3, 188, 191 and 192 have over 60% hypouricemic effect at 2 hours after oral administration. As results described above, it is confirmed that compounds in the present invention have a potent effect reducing serum uric acid.

INDUSTRIAL APPLICABILITY

The (aza)indole derivatives represented by the above general formula (I) of the present invention or prodrugs, or pharmaceutically acceptable salts thereof exert an excellent xanthine oxidase inhibitory activity, and therefore, can exert an inhibitory activity of uric acid production and lower the blood uric acid level. Therefore, the present invention can provide an agent for the prevention or treatment of hyperuricemia, gouty tophus, gouty arthritis, renal disorder associated with hyperuricemia, urinary calculi or the like.

The invention claimed is:

1. 4-(3-Cyano-5,6-difuoro-indol-1-yl)-2-hydroxy-benzoic acid or a pharmaceutically acceptable salt thereof.

2. 4-(3-Cyano-indol-1-yl)-2-hydroxy-benzoic acid or a pharmaceutically acceptable salt thereof.

3. 4-(3-Cyano-5-fluoro-indol-1-yl)-2-hydroxy-benzoic acid or a pharmaceutically acceptable salt thereof.

4. 4-(3-Cyano-6-fluoro-indol-1-yl)-2-hydroxy-benzoic acid or a pharmaceutically acceptable salt thereof.

\* \* \* \* \*